US011807896B2

(12) United States Patent
Rice et al.

(10) Patent No.: US 11,807,896 B2
(45) Date of Patent: Nov. 7, 2023

(54) PHYSICAL LINKAGE PRESERVATION IN DNA STORAGE

(71) Applicant: DOVETAIL GENOMICS, LLC, Scotts Valley, CA (US)

(72) Inventors: Brandon J. Rice, Santa Cruz, CA (US); David Haussler, Santa Cruz, CA (US)

(73) Assignee: Dovetail Genomics, LLC, Scotts Valley, CA (US)

( * ) Notice: Subject to any disclaimer, the term of this patent is extended or adjusted under 35 U.S.C. 154(b) by 304 days.

(21) Appl. No.: 15/561,447

(22) PCT Filed: Mar. 25, 2016

(86) PCT No.: PCT/US2016/024225
§ 371 (c)(1),
(2) Date: Sep. 25, 2017

(87) PCT Pub. No.: WO2016/154540
PCT Pub. Date: Sep. 29, 2016

(65) Prior Publication Data
US 2018/0119203 A1    May 3, 2018

Related U.S. Application Data

(60) Provisional application No. 62/138,882, filed on Mar. 26, 2015.

(51) Int. Cl.
*C12P 19/34*    (2006.01)
*C12Q 1/6806*    (2018.01)
*C12N 15/10*    (2006.01)

(52) U.S. Cl.
CPC .......... *C12Q 1/6806* (2013.01); *C12N 15/10* (2013.01); *C12N 15/1003* (2013.01); *C12N 15/1093* (2013.01)

(58) Field of Classification Search
USPC ......... 435/6.1, 6.11, 6.12, 91.1, 91.2, 91.51; 436/94, 501; 536/23.1, 24.3, 24.33, 25.3
See application file for complete search history.

(56) References Cited

U.S. PATENT DOCUMENTS 3,817,837 A    6/1974 Rubenstein et al.
3,850,752 A    11/1974 Schuurs et al.
(Continued)

FOREIGN PATENT DOCUMENTS

AU    2012222108 A1    7/2013
DE    10149786 A1    7/2003
(Continued)

OTHER PUBLICATIONS

The definition of "N50" from Metagenomics. Printed on Jun. 4, 2020.*
(Continued)

*Primary Examiner* — Frank W Lu
(74) *Attorney, Agent, or Firm* — Wilson Sonsini Goodrich & Rosati

(57) ABSTRACT

Disclosed herein are compositions, systems, kits and methods related to preserving physical linkage information of isolated DNA subject to DNA damage, and identifying a nucleic acid preservative. Physical linkage information and DNA integrity may be preserved by methods relating to reassembly of chromatin onto isolated DNA molecules so as to protect the nucleic acids, preserve physical linkage information, or size select molecules of interest. Nucleic acid compositions produced by methods disclosed herein are preserved so as to be analyzed, for example, by high throughput sequencing methods.

18 Claims, 3 Drawing Sheets

(56) References Cited

U.S. PATENT DOCUMENTS

| | | |
|---|---|---|
| 3,939,350 A | 2/1976 | Kronick et al. |
| 3,996,345 A | 12/1976 | Ullman et al. |
| 4,275,149 A | 6/1981 | Litman et al. |
| 4,277,437 A | 7/1981 | Maggio |
| 4,366,241 A | 12/1982 | Tom et al. |
| 4,988,617 A | 1/1991 | Landegren et al. |
| 5,143,854 A | 9/1992 | Pirrung et al. |
| 5,234,809 A | 8/1993 | Boom et al. |
| 5,242,794 A | 9/1993 | Whiteley et al. |
| 5,348,853 A | 9/1994 | Wang et al. |
| 5,476,930 A | 12/1995 | Letsinger et al. |
| 5,494,810 A | 2/1996 | Barany et al. |
| 5,567,583 A | 10/1996 | Wang et al. |
| 5,571,639 A | 11/1996 | Hubbell et al. |
| 5,593,839 A | 1/1997 | Hubbell et al. |
| 5,705,628 A | 1/1998 | Hawkins |
| 5,780,613 A | 7/1998 | Letsinger et al. |
| 5,786,146 A | 7/1998 | Herman et al. |
| 5,837,832 A | 11/1998 | Chee et al. |
| 5,989,823 A | 11/1999 | Jayasena et al. |
| 5,994,056 A | 11/1999 | Higuchi |
| 6,033,854 A | 3/2000 | Kurnit et al. |
| 6,110,709 A | 8/2000 | Ausubel et al. |
| 6,117,635 A | 9/2000 | Nazarenko et al. |
| 6,171,785 B1 | 1/2001 | Higuchi |
| 6,174,670 B1 | 1/2001 | Wittwer et al. |
| 6,225,109 B1 | 5/2001 | Juncosa et al. |
| 6,287,766 B1 | 9/2001 | Nolan et al. |
| 6,326,145 B1 | 12/2001 | Whitcombe et al. |
| 6,416,950 B1 | 7/2002 | Lohse et al. |
| 6,449,562 B1 | 9/2002 | Chandler et al. |
| 6,582,938 B1 | 6/2003 | Su et al. |
| 6,632,598 B1 | 10/2003 | Zhang et al. |
| 6,787,308 B2 | 9/2004 | Balasubramanian et al. |
| 6,833,246 B2 | 12/2004 | Balasubramanian |
| 6,897,023 B2 | 5/2005 | Fu et al. |
| 6,969,488 B2 | 11/2005 | Bridgham et al. |
| 7,001,724 B1 | 2/2006 | Greenfield |
| 7,361,468 B2 | 4/2008 | Liu et al. |
| 7,414,117 B2 | 8/2008 | Saito et al. |
| 7,425,415 B2 | 9/2008 | Pfeifer et al. |
| 7,709,179 B2 | 5/2010 | Iwashita |
| 7,709,197 B2 | 5/2010 | Drmanac |
| 7,901,891 B2 | 3/2011 | Drmanac |
| 7,985,546 B2 | 7/2011 | Church et al. |
| 8,058,004 B2 | 11/2011 | Oleinikov |
| 8,071,296 B2 | 12/2011 | Ruan et al. |
| 8,076,070 B2 | 12/2011 | Chen et al. |
| 8,153,373 B2 | 4/2012 | De Laat et al. |
| 8,278,112 B2 | 10/2012 | Shokat et al. |
| 8,367,322 B2 | 2/2013 | Barany et al. |
| 8,642,295 B2 | 2/2014 | De Laat et al. |
| 8,673,562 B2 | 3/2014 | Drmanac |
| 8,741,577 B2 | 6/2014 | Graneli et al. |
| 8,841,075 B1 | 9/2014 | Borner et al. |
| 9,411,930 B2 | 8/2016 | Green, Jr. et al. |
| 9,434,985 B2 | 9/2016 | Dekker et al. |
| 9,715,573 B2 | 7/2017 | Putnam |
| 10,529,443 B2 | 1/2020 | Green, Jr. et al. |
| 10,825,553 B2 | 11/2020 | Green, Jr. et al. |
| 10,947,579 B2 | 3/2021 | Troll et al. |
| 2002/0012930 A1 | 1/2002 | Rothberg et al. |
| 2002/0190663 A1 | 12/2002 | Rasmussen |
| 2003/0022207 A1 | 1/2003 | Balasubramanian et al. |
| 2003/0044781 A1 | 3/2003 | Korlach et al. |
| 2003/0064398 A1 | 4/2003 | Barnes |
| 2003/0068629 A1 | 4/2003 | Rothberg et al. |
| 2003/0100102 A1 | 5/2003 | Rothberg et al. |
| 2003/0148344 A1 | 8/2003 | Rothberg et al. |
| 2003/0170689 A1 | 9/2003 | Stamatoyannapoulos et al. |
| 2003/0228627 A1 | 12/2003 | Emerson et al. |
| 2004/0106110 A1 | 6/2004 | Balasubramanian et al. |
| 2004/0197779 A1 | 10/2004 | Apffel |
| 2004/0225004 A1* | 11/2004 | Zeligs .................. A61K 31/405 514/419 |
| 2004/0248161 A1 | 12/2004 | Rothberg et al. |
| 2005/0079510 A1 | 4/2005 | Berka et al. |
| 2005/0100932 A1 | 5/2005 | Lapidus et al. |
| 2005/0124022 A1 | 6/2005 | Srinivasan et al. |
| 2005/0130161 A1 | 6/2005 | Fraser et al. |
| 2005/0260625 A1 | 11/2005 | Wang |
| 2006/0012784 A1 | 1/2006 | Ulmer |
| 2006/0012793 A1 | 1/2006 | Harris |
| 2006/0024678 A1 | 2/2006 | Buzby |
| 2006/0024711 A1 | 2/2006 | Lapidus et al. |
| 2006/0078909 A1 | 4/2006 | Srinivasan et al. |
| 2006/0078937 A1 | 4/2006 | Korlach et al. |
| 2006/0252025 A1 | 11/2006 | Nitta et al. |
| 2006/0252061 A1 | 11/2006 | Zabeau et al. |
| 2007/0172839 A1 | 7/2007 | Smith et al. |
| 2007/0231817 A1 | 10/2007 | De Laat et al. |
| 2007/0277251 A1 | 11/2007 | Wartiovaara et al. |
| 2008/0233101 A1 | 9/2008 | Sauer |
| 2009/0011943 A1 | 1/2009 | Drmanac et al. |
| 2009/0111115 A1 | 4/2009 | Drmanac et al. |
| 2009/0191598 A1 | 7/2009 | Ruan et al. |
| 2009/0202998 A1 | 8/2009 | Schlumpberger et al. |
| 2009/0233291 A1 | 9/2009 | Chen et al. |
| 2009/0269771 A1 | 10/2009 | Schroeder |
| 2009/0298064 A1 | 12/2009 | Batzoglou et al. |
| 2010/0062947 A1 | 3/2010 | De Laat et al. |
| 2010/0081141 A1 | 4/2010 | Chen et al. |
| 2010/0093986 A1 | 4/2010 | Zwick et al. |
| 2010/0130373 A1 | 5/2010 | Dekker et al. |
| 2010/0267571 A1 | 10/2010 | Watanabe et al. |
| 2011/0033854 A1 | 2/2011 | Drmanac et al. |
| 2011/0256593 A1 | 10/2011 | Hsieh et al. |
| 2011/0287947 A1 | 11/2011 | Chen et al. |
| 2011/0300537 A1 | 12/2011 | Slepnev |
| 2011/0306504 A1 | 12/2011 | Xiao et al. |
| 2012/0197533 A1 | 8/2012 | Nazarenko et al. |
| 2012/0302449 A1 | 11/2012 | Dong et al. |
| 2012/0330559 A1 | 12/2012 | Jiang et al. |
| 2013/0005585 A1 | 1/2013 | Anderson et al. |
| 2013/0045872 A1 | 2/2013 | Zhou et al. |
| 2013/0053254 A1 | 2/2013 | Hollander |
| 2013/0096009 A1 | 4/2013 | Dekker et al. |
| 2013/0183672 A1 | 7/2013 | De Laat et al. |
| 2013/0203605 A1 | 8/2013 | Shendure et al. |
| 2013/0259839 A1 | 10/2013 | Aharonov et al. |
| 2013/0310548 A1 | 11/2013 | Park |
| 2014/0031241 A1 | 1/2014 | Nicol et al. |
| 2014/0057799 A1 | 2/2014 | Johnson et al. |
| 2014/0141982 A1 | 5/2014 | Jacobson et al. |
| 2014/0220587 A1 | 8/2014 | Green, Jr. et al. |
| 2015/0316500 A1 | 11/2015 | Dale et al. |
| 2015/0363550 A1 | 12/2015 | Green, Jr. et al. |
| 2016/0289738 A1* | 10/2016 | Grosveld .............. C12Q 1/682 |
| 2016/0305855 A1 | 10/2016 | Richardson et al. |
| 2016/0312213 A1* | 10/2016 | Rokhsar .............. C12Q 1/6883 |
| 2016/0319365 A1 | 11/2016 | Saffroy et al. |
| 2017/0159109 A1 | 6/2017 | Zheng et al. |
| 2017/0276598 A1 | 9/2017 | Ikuyama |
| 2017/0314014 A1 | 11/2017 | Green et al. |
| 2019/0143328 A1 | 5/2019 | Savran et al. |

FOREIGN PATENT DOCUMENTS

| | | |
|---|---|---|
| DE | 10214395 A1 | 10/2003 |
| DE | 10356837 A1 | 6/2005 |
| DE | 102004009704 A1 | 9/2005 |
| DE | 102004025744 A1 | 12/2005 |
| DE | 102004025745 A1 | 12/2005 |
| DE | 102004025746 A1 | 12/2005 |
| DE | 102004025694 A1 | 2/2006 |
| DE | 102004025695 A1 | 2/2006 |
| DE | 102004025696 A1 | 2/2006 |
| EP | 0476014 A1 | 3/1992 |
| EP | 0624059 A1 | 11/1994 |
| EP | 0717113 A2 | 6/1996 |
| EP | 0728520 A1 | 8/1996 |
| EP | 1967582 A1 | 9/2008 |
| EP | 2083090 A1 | 7/2009 |
| EP | 2811022 A1 | 12/2014 |

(56) References Cited

FOREIGN PATENT DOCUMENTS

| | | |
|---|---|---|
| WO | WO-9015070 A1 | 12/1990 |
| WO | WO-9210092 A1 | 6/1992 |
| WO | WO-9309668 A1 | 5/1993 |
| WO | WO-9511995 A1 | 5/1995 |
| WO | WO-9729212 A1 | 8/1997 |
| WO | WO-9841651 A1 | 9/1998 |
| WO | WO-0014281 A2 | 3/2000 |
| WO | WO-02088382 A2 | 11/2002 |
| WO | WO-02103046 A2 | 12/2002 |
| WO | WO-03020968 A2 | 3/2003 |
| WO | WO-03031947 A2 | 4/2003 |
| WO | WO-03042657 A2 | 5/2003 |
| WO | WO-2005001113 A2 | 1/2005 |
| WO | WO-2005005655 A1 | 1/2005 |
| WO | WO-2005005657 A1 | 1/2005 |
| WO | WO-2005044836 A2 | 5/2005 |
| WO | WO-2006040550 A1 | 4/2006 |
| WO | WO-2006097320 A2 | 9/2006 |
| WO | WO-2007093819 A2 | 8/2007 |
| WO | WO-2008024473 A2 | 2/2008 |
| WO | WO-2008127281 A2 | 10/2008 |
| WO | WO-2008143903 A2 | 11/2008 |
| WO | WO-2009053039 A1 | 4/2009 |
| WO | WO-2009147386 A1 | 12/2009 |
| WO | WO-2010011774 A1 | 1/2010 |
| WO | WO-2010036323 A1 | 4/2010 |
| WO | WO-2011056872 A2 | 5/2011 |
| WO | WO-2012005595 A2 | 1/2012 |
| WO | WO-2012028737 A1 | 3/2012 |
| WO | WO-2012045012 A2 | 4/2012 |
| WO | WO-2012047726 A1 | 4/2012 |
| WO | WO-2012054873 A2 | 4/2012 |
| WO | WO-2012106546 A2 | 8/2012 |
| WO | WO-2012142531 A2 | 10/2012 |
| WO | WO-2012142611 A2 | 10/2012 |
| WO | WO-2012150317 A1 | 11/2012 |
| WO | WO-2013078470 A2 | 5/2013 |
| WO | WO-2014012010 A1 | 1/2014 |
| WO | WO-2014047561 A1 | 3/2014 |
| WO | WO-2014121091 A1 | 8/2014 |
| WO | WO-2015075196 A1 | 5/2015 |
| WO | WO-2015089243 A1 | 6/2015 |
| WO | WO-2015123588 A1 | 8/2015 |
| WO | WO-2016019360 A1 | 2/2016 |
| WO | WO-2016044313 A1 | 3/2016 |
| WO | WO-2016061517 A2 | 4/2016 |
| WO | WO-2016164313 A1 | 10/2016 |
| WO | WO-2016207647 A1 | 12/2016 |
| WO | WO-2016207653 A1 | 12/2016 |
| WO | WO-2016207661 A1 | 12/2016 |

OTHER PUBLICATIONS

Wu et al., Stability of Genomic DNA at Various Storage Conditions. Poster given at annual ISBER conference, 2009.*

Adams, et al. The Genome Sequence of *Drosophila melanogaster*. Science Mar. 24, 2000, 287.5461: 2185-2195 DOI: 10.1126/science.287.5461.2185.

Adey, A. et al. In vitro, long-range sequence information for 19 de novo genome assembly via transposase contiguity. Genome Res., 24(12):2041-2049, Dec. 2014.

Alkan, C. et al. Limitations of next-eneration genome sequence assembly. Nat. Methods, 8(1):61-65, Jan. 2011.

Allison 2007 Fundamental Molecular Biology. Wiley-Blackwell, Chapter 8, pp. 1-15.

Amini, S. et al. Haplotype-resolved whole-genome sequencing by contiguity-preserving transposition and combinatorial indexing. Nat. Genet., 46(12):1343-1349, Dec. 2014.

Ausubel, et al., eds. 1993. Current Protocols in Molecular Biology. Part 1: *E. coli*, plasmids, and bacteriophages,pp. 1-15.

Bansal et al., Hapcut: an efficient and accurate algorithm for the haplotype assembly problem, Bioinformatics, 24(16): i153-i159 (Aug. 9, 2008).

Blander, G et al.SIRT1 Shows No Substrate Specificity in Vitro. Journal of biological Chemistry (2005) vol. 280, p. 9780-9785.

Blecher-Gonen, Ronnie et al. High-throughput chromatin immunoprecipitation for genome-wide mapping of in vivo protein-DNA interactions and epigenomic states. Nature Protocols, 8(3):539-554 (Feb. 21, 2013).

Bolger, A.M. et al. Trimmomatic: a flexible trimmer for Illumina sequence data. Bioinformatics, 30(15):2114-2120, Aug. 2014.

Burton, J.N. et al. Chromosome-scale scaffolding of de novo genome assemblies based on chromatin interactions. Nat. Biotechnol., 31(12):1119-1125, Dec. 2013.

Chapman, et al. Meraculous: de novo genome assembly with short paired-end reads. PloS one. 2011, 6.8: e23501.

Zinchenko, A. et al. Compaction of Single-Chain DNA by Histone-Inspired Nanoparticles. Physical Review Letters, 95(22); 228101 (2005).

Constans, A. Scientist. 2003, 17.13: 36.

Cortese, J. Array of options. Scientist. 2000, 14.11: 26.

Cortese, J. The array of today. Scientist. 2000 14.17:25.

De Koning, A.P. et al. Repetitive elements may comprise over two-thirds of the human genome. PLoS Genet., 7(12):e1002384, Dec. 2011.

Dekker et al., A closer look at long-range chromosomal interactions. Trends in Biochemical Science (Jun. 2003) 28(6):277-280.

Dekker et al., Capturing chromosome conformation, Science, 2002, vol. 295, pp. 1306-1311.

Dixon, J. R. et al. Topological domains in mammalian genomes identified by analysis of chromatin interactions. Nature, 485(7398):376-380, May 2012.

Dostie et al., Chromosome Conformation Capture Carbon Copy (5C): a massively parallel solution for mapping interaction between genomic elements, Genome research, 2006, vol. 16, No. 10, pp. 1299-1309.

Dower, et al. Recombinant and synthetic randomized peptide libraries. Ann. Rep. Med. Chem. 1991, 26:271-280.

Drmanac, et al. Human Genome Sequencing Using Unchained Base Reads on Self-Assembling DNA Nanoarrays. Science Jan. 1, 2010, 327.5961: 78-81 DOI:10.1126/science.1181498.

Ekins, R. et al. Microarrays: Their Origins and applications. Trends in Biotechnology, 17(6); 217-218 (Jun. 1999).

Fan et al. A versatile assay for high-throughput gene expression profiling on universal array matrices. Genome Research, 2004, vol. 14 No. 5 pp. 878-885.

Fangman, et al. Activation of replication origins within yeast chromosomes, Annual Review of Cell Biology, 7(1); 375-402 (1991).

Ferraiuolo, M.A. et al. From cells to chromatin: capturing snapshots of genome organization with 5C technology. Methods. Nov. 2012;58(3):255-67. Epub Nov. 5, 2012.

Flot, JF et al. Contact genomics: scaffolding and phasing (meta) genomes using chromosome 3D physical signatures. FEBS Letters 589 (2015) 2966-2974.

Fodor, et al. Light-directed, spatially addressable parallel chemical synthesis. Science. Feb. 15, 1991, 251.4995: 767-773; DOI: 10.1126/science.1990438.

Fullwood, et al. ChIP-Based Methods for the Identification of Long-Range Chromatin Interactions Journal of Cellular Biochemistry, vol. 107, No. 1, pp. 30-39, May 2009.

Fullwood, MJ. et al. Chromatin interaction analysis using paired-end tag sequencing. Jan. 2010. Curr. Prot. in Mol. Biol. Chapter 21; unit 21 .15.1-25. doi: 10.1002/0471142727.mb2115s89.

Fyodorov, et al. Chromatin assembly in vitro with purified recombinant ACF and NAP-1. Methods in enzymology. 2002, 371: 499-515.

Garaj, et al. Graphene as a sub-nanometer trans-electrode membrane. Nature. Sep. 9, 2010, 467.7312: 190-193. doi: 10.1038/nature09379.

GE Healthcare: Instructions 71-7106-00AF Activated Thiol Sepharose 4B (pp. 1-12) (Jul. 2008).

Gilmour, David S., et al. Detecting protein-DNA interactions in vivo: distribution of RNA polymerase on specific bacterial genes. Proceedings of the National Academy of Sciences. (1984) 81(14): 4275-4279.

(56) References Cited

OTHER PUBLICATIONS

Gnerre, S. et al. High-quality draft assemblies of mammalian genomes from massively parallel sequence data. Proc. Natl. Acad. Sci. U.S.A., 108 (4):1513-1518, Jan. 2011.
Goodwin, S. et al. Oxford nanopore sequencing and de novo assembly of a eukaryotic genome. bioRxiv, pp. 1-28 (Jul. 15, 2015).
Green R.E. et al. Three crocodilian genomes reveal ancestral patterns of evolution among archosaurs. Science, 346(6215):1254449 (1-11) (Dec. 12, 2014).
Gwynne, P. et al. Microarray analysis: the next revolution in molecular biology. Science. pp. 1-6 (Aug. 6, 1999).
Haussler, D., et al. Genome 10K: a proposal to obtain whole-genome sequence for 10,000 vertebrate species. J. Hered., 100(6):659-674, 2009.
Heid, C.A. et al. Real time quantitative PCR. Genome Research, 6(10): 986-994 (1996).
Herschleb, J. et al. Pulsed-field gel electrophoresis. Pulsed-field gel electrophoresis. Nature Protocols 2(3):677-84 (Mar. 29, 2007).
International Application No. PCT/US16/57557 International Search Report and Written Opinion dated Mar. 10, 2017.
International Application No. PCT/US17/32466 International Search Report and Written Opinion dated Aug. 22, 2017.
International Application No. PCT/US2014/014184 International Search Report and Written Opinion dated Apr. 23, 2014.
International Application No. PCT/US2015/043327 International Preliminary Report on Patentability dated Feb. 7, 2017.
International Application No. PCT/US2016/018295 International Preliminary Report on Patentability dated Aug. 31, 2017 .
International Application No. PCT/US2016/018295 International Search Report dated Aug. 4, 2016.
International Application No. PCT/US2016/024225 International Preliminary Report on Patentability dated Sep. 26, 2017.
International Application No. PCT/US2016/024225 International Search Report dated Jul. 10, 2016.
Kalhor, R. et al. Genome architectures revealed by tethered chromosome conformation capture and population-based modeling, Nature Biotechnology, 30(1): 90-98 (Jan. 2012).
Kaplan, et al. Nat. Biotechnol. 2013, 31: 1139-1143.
Kaplan, N. et al. High-throughput genome scaffolding from in vivo DNA interaction frequency. Nat. Biotechnol., 31(12):1143-1147 (Dec. 2013).
Kidd, J. M. et al. Mapping and sequencing of structural variation from eight human genomes. Nature, 453(7191):56-64, May 2008.
Kitzman, Jacob O. et al. Haplotype-resolved genome sequencing of a Gujarati Indian individual, Nature Biotechnology, 29(1): 59-63 (Jan. 2011).
Koren, S. et al. Hybrid error correction and de novo assembly of single-molecule sequencing reads. Nature biotechnology, 30(7):693-700, 2012.
Kundu et al. Activator-dependent transcription from chromatin in vitro involving targeted histone acetylation by p300. Molecular cell. 2000, 6.3: 551-561.
Lasken, Roger S. et al. Mechanism of chimera formation during the Multiple Displacement Amplification reaction. BMC biotechnology. 7(19):1-11 (Apr. 12, 2007).
Lee, Ti et al. Chromatin immunoprecipitation and microarray-based analysis of protein location, Nature Protocols 1(2): 729-748 (2006).
Lemieux, B. et al. Overview of DNA chip technology. Molecular Breeding 4: 277-289 (1998).
Levene, M.J. et al., Zero-Mode Waveguides for Single-Molecule Analysis at High Concentrations, Science, 299(5607):682-686 (Jan. 31, 2003).
Lieberman-Aiden, E. et al. Comprehensive mapping of long-range interactions reveals folding principles of the human genome. Science, 326(5950):289-293, Oct. 2009.
Liu, B. et al. COPE: an accurate k-mer-based pair-end reads connection tool to facilitate genome assembly. Bioinformatics, 28(22): 2870-2874 (Oct. 8, 2012).
Lupski, James R. et al. Whole-genome sequencing in a patient with Charcot-Marie-Tooth neuropathy. New England Journal of Medicine, 362(13): 1181-1191 (Apr. 1, 2010).
Lusser, Alexandra et al. Strategies for the reconstitution of chromatin. Nature Methods, 1(1):19-26 (Oct. 2004).
Ma, H. et al. Application of Real-time Polymerase Chain Reaction (RT-PCR), The Journal of American Science, 2 (3):1-15 (Aug. 10, 2006).
Margulies, M. et al. Genome sequencing in open microfabricated high density picolitre reactors. Nature 437(7057):376-380 (Sep. 15, 2005).
Marie-Nelly, H. et al. High-quality genome (re)assembly using chromosomal contact data. Nature Communications 5:5695 (Dec. 17, 2014).
Marshall, A. et al. DNA chips: an array of possibilities. Nature Biotechnology, 16(1): 27-31 (Jan. 1998).
Mary, I. et al. Metaproteomic and metagenomic analyses of defined oceanic microbial populations using microwave cell fixation and flow cytometric sorting. FEMS Microbiol Ecol. 74(1):10-18 (Oct. 2010). E-Pub. Jul. 5, 2010.
Meyer, M. et al. Illumina sequencing library preparation for highly multiplexed target capture and sequencing. Cold Spring Harb Protoc, 2010(6):pdb.prot5448 (Jun. 2010).
Miller et al. A Simple salting out procedure for extracting DNA from human nucleated cells. Nucleic Acids Research vol. 16, No. 3, 1215 (1988).
Morrison, AJ et al. Retinoblastoma Protein Transcriptional Repression through Histone Deacetylation of a Single Nucleosome. Molecular and Cellular biology 22(3);856-865 (Feb. 2002).
Myers, E.W. et al. A Whole-Genome Assembly of Drosohila. Science, 287(5461):2196-2204 (Mar. 24, 2000).
Nazarenko, I.A. et al. A closed tube format for amplification and detection of DNA based on energy transfer. Nucleic acids research, 25(12):2516-2521 (Jun. 15, 1997).
Peng, Z. et al. Generation of long insert pairs using a Cre-LoxP Inverse PCR approach, PLoS One, 7(1): e29437 (2012) E-Pub Jan. 9, 2012.
Peters, B.A. et al. Accurate whole-genome sequencing and haplotyping from 10 to 20 human cells. Nature, 487(7406):190-195 (Jul. 11, 2012).
Putnam, N. H. et al. Supplemental Material—Chromosome-scale shotgun assembly using an in vitro method for long-range likage. Genome Research 26:342-350 (2016). E-Pub Feb. 4, 2016.
Putnam, N.H. et al. Chromosome-scale shotgun assembly using an in vitro method for long-range linkage. arXiv:1502.05331 [q-bio. GN] pp. 1-25. Feb. 18, 2015 (Retrieved from the Internet Oct. 8, 2015).
Putnam, Nicholas H. et al. Chromosome-scale shotgun assembly using an in vitro method for long-range linkage. Genome Research, 26(3):342-350 (Mar. 2016).
Quail, M.A. et al. A tale of three next generation sequencing platforms: comparison of Ion Torrent, Pacific Biosciences and Illumina MiSeq sequencers. BMC Genomics, 13:341 (Jul. 24, 2012).
Rios, J. et al. Identification by whole-genome resequencing of gene defect responsible for severe hypercholesterolemia. Human Molecular Genetics, 19(22): 4313-4318 (Nov. 15, 2010). E-Pub Aug. 18, 2010).
Rozowsky, J. et al. AlleleSeq: analysis of allele-specific expression and binding in a network framework. Mol. Syst. Biol., 7:522; pp. 1-15 (Aug. 2, 2011).
Salzberg, S.L. et al. GAGE: A critical evaluation of genome assemblies and assembly algorithms. Genome Res., 22(3):557-567 (Mar. 2012). E-Pub Jan. 6, 2012.
Sambrook, et al. Mixed Oligonucleotide-primed Amplification of cDNA (MOPAC). Cold Spring Harbor Protocols, pp. 1-30 (2006).
Schena M. (ed.), Microarray Biochip Technology (2000). A bioTechniques Books Publication. Eaton Publishing, pp. 1-44. ISBN-10: 1881299376 ISBN-13: 978-1881299370.
Schena, Mark et al. Genes, genomes, and chips. DNA microarrays: A practical approach. Oxford University Press, pp. 1-18 (1999); ISBN-10: 1881299376 ISBN-13: 978-1881299370.

(56) References Cited

OTHER PUBLICATIONS

Schloss, P.D. et al. A statistical toolbox for metagenomics: assessing functional diversity in microbial communities, BMC Bioinformatics 9(34):1-15 (Jan. 23, 2008).
Schmidt, D. et al. ChIP-seq: using high-throughput sequencing to discover protein-DNA interactions. Methods 48(3): 240-248(Jul. 2009).
Schutze, T. et al. A calibrated diversity assay for nucleic acid libraries using DiStRO—a Diversity Standard of Random Oligonucleotides. Nucleic Acids Research, 38(4):e23 (pp. 1-5) Mar. 2010; epub Dec. 3, 2009.
Schwartz, D.C. et al. Separation of yeast chromosome-sized DNAs by pulsed field gradient gel electrophoresis. Cell 37(1): 67-75 (May 1984).
Selvaraj, S. et al. Whole-genome haplotype reconstruction using proximity-ligation and shotgun sequencing. Nature Biotechnology, 31(12):1111-1118 (Dec. 2013).
Selvaraj, S. et al. Complete haplotype phasing of the MHC and KIR loci with targeted HaploSeq. BMC Genomics 16:900, pp. 1-7 (Nov. 5, 2015).
Shalon, D. et al. A DNA microarray system for analyzing complex DNA samples using two-color fluorescent probe hybridization. Genome research, 6(7): 639-645 (Jul. 1996).
Shedlock, A.M. et al. Phylogenomics of nonavian reptiles and the structure ofthe ancestral amniote genome. Proc. Natl. Acad. Sci. U.S.A., 104(8):2767-2772 (Feb. 20, 2007). E-Pub Feb. 16, 2007.
Sheridan, C. Milestone approval lifts Illumina's NGS from research into clinic. Nature Biotechnology, 32(2):111-112 (Feb. 2014).
Shiio Y., et al. Quantitative proteome analysis using isotope-coded affinity tags and mass spectrometry. Nature Protocols, 1(1): 139-145 (2006).
Sigma Protein A immobilized product sheet (Published Mar. 2001) accessed on Apr. 14, 2016.
Simpson, et al. Efficient de novo assembly of large genomes using compressed data structures. Genome Res. Mar. 2012; 22(3): 549-556. doi: 10.1101/gr.126953.111.
Simpson, J.T. et al. Efficient de novo assembly of large genomes using compressed data structures. Genome Res, 22(3): 549-556 (Mar. 2012). E-Pub Dec. 7, 2011. doi: 10.1101/gr.126953.111.
Solomon, M.J. et al. Formaldehyde-mediated DNA-protein crosslinking: a probe for in vivo chromatin structures. Proceedings of the National Academy of Sciences, 82(19): 6470-6474 (Oct. 1985).
Solomon, M.J. et al. Mapping protein-DNA interactions in vivo with formaldehyde: evidence that histone H4 is retained on a highly transcribed gene. Cell, 53(6):937-947 (Jun. 17, 1988).
Soni, et al. Progress toward ultrafast DNA sequencing using solid-state nanopores. Clin Chem, 53(11):1996-2001 (Nov. 2007). Epub Sep. 21, 2007.
Splinter, E. 3C Technology: Analyzing the Spatial Organization of Genomic Loci In Vivo Methods in Enzymology, 375:493-507 (2004).
Splinter, E. et al. Determining long-range chromatin interactions for selected genomic sites using 4C-seq technology: from fixation to computation. Methods. Nov. 2012;58(3):221-30. (Epub May 17, 2012).
Storek, Michael J. et al. High-resolution footprinting of sequence-specific protein-DNA contacts, Nature Biotechnology, 20(2):183-186 (Feb. 1, 2002).
Tanizawa, H. et al., Mapping of long-range associations throughout the fission yeast genome reveals global genome organization linked to transcriptional regulation. Nucleic Acid Research, 38(22):8164-8177 (Dec. 2010). Epub Oct. 28, 2010.
Teague, B. et al. High-resolution human genome structure by single-molecule analysis. Proceedings of the National Academy of Sciences, 107(24): 10848-10853 (Jun. 15, 2010).
Torjensen, I. Genomes of 100,000 people will be sequenced to create an open access research resource. BMJ, 347:f6690 (Nov. 6, 2013).
Tuzun, E. et al. Fine-scale structural variation ofthe human genome. Nat. Genet., 37(7):727-732 (Jul. 2005). Epub May 15, 2005.
Tyagi, S. et al. Molecular beacons: probes that fluoresce upon hybridization. Nature Biotechnology, 14(3):303-308 (Mar. 1996).
Umbarger, M.A. Chromosome conformation capture assays in bacteria. Methods 58(3):212-220 (Nov. 2012). doi: 10.1016/j.ymeth.2012.06.017. Epub Jul. 6, 2012.
U.S. Appl. No. 14/170,339 Non-Final Office Action dated Oct. 20, 2014.
U.S. Appl. No. 14/170,339 Restriction Requirement dated Mar. 14, 2014.
U.S. Appl. No. 14/764,945 Non-Final Office Action dated Sep. 22, 2017.
U.S. Appl. No. 15/045,818 Non-Final Office Action dated Jan. 30, 2017.
U.S. Appl. No. 15/045,818 Non-final Office Action dated Sep. 1, 2016.
U.S. Appl. No. 15/045,818 Notice of Allowance dated May 19, 2017.
U.S. Appl. No. 15/137,988 Notice of Allowance dated Mar. 15, 2017.
U.S. Appl. No. 15/167,880 Non-Final Office Action dated Jul. 3, 2017.
U.S. Appl. No. 15/167,880 Notice of Allowance dated Oct. 26, 2017.
U.S. Appl. No. 15/649,268 Non-Final Office Action dated Oct. 20, 2017.
Venter, J.C. et al. The sequence of the human genome. Science, 291(5507):1304-1351 (Feb. 16, 2001).
Voskoboynik, A. et al. The genome sequence of the colonial chordate, Botryllus schlosseri. eLife, 2:e00569 (2013). doi: 10.7554/eLife.00569. Epub Jul. 2, 2013.
Weisenfeld N.I., et al. Comprehensive variation discovery in single human genomes. Nat. Genet. 46(12):1350-1355 (Dec. 2014). doi: 10.1038/ng.3121. Epub Oct. 19, 2014.
Whitcombe, D. et al. Detection of PCR Products Using Self-probing Amplicons and Fluorescence. Nature Biotechnology, 17(8):804-807 (Aug. 1999).
Williams, L.J. Paired-end sequencing of Fosmid libraries by Illumina. Genome Res., 22(11):2241-2249 (Nov. 2012). Epub Jul. 16, 2012.
Wing, R.D., et al. An improved method of plant megabase DNA isolation in agarose microbeads suitable for physical mapping and YAC cloning. The Plant Journal, 4(5):893-898 (1993).
Wu, C.C. et al. Long-span, mate-pair scaffolding and other methods for faster next-generation sequencing library creation. Nat. Methods, 9(9; Advertising Feature):i-ii (Sep. 2012).
Wu, T.D. et al. GMAP: a genomic mapping and alignment program for mRNA and EST sequences. Bioinformatics, 21(9):1859-1875, May 1, 2005. Epub Feb. 22, 2005.
Zhou, S. et al. A single molecule scaffold for the maize genome. PLoS Genetics, 5(11): e1000711; pp. 1-14 (Nov. 20, 2009).
Enoiu, Milica et al. Repair of cisplatin-induced DNA interstrand crosslinks by a replication-independent pathway involving transcription-coupled repair and translesion synthesis. Nucleic Acids Research, 40(18):8953-8964 (2012).
European Patent Application No. 17796959 Extended European Search Report dated Oct. 28, 2019.
Extended European Search Report, Application No. 14745949.9 European Patent Office, dated Nov. 21, 2016.
Kuo et al. In Vivo Cross-Linking and Immunoprecipitation for Studying Dynamic Protein: DNA Associations in a Chromatin Environment. Methods 19:425-433 (1999).
Nelson et al. Protocol for the fast chromatin immunoprecipitation (ChIP) method. Nature Protocols 1(1):179-185 (2006).
Oliveira et al. Translocation capture sequencing: A method for high throughput mapping of chromosomal rearrangements. J. of Immunological Methods 375:176-181 (2012).
Orlando. Mapping chromosomal proteins in vivo by formaldehydecrosslinked-chromatin immunoprecipitation. TIBS 25:99-104 (2000).
Park. ChIP-seq: advantages and challenges of a maturing technology. Nature Reviews Genetics vol. 10, pp. 669-680 (2009).
Thavarajah et al. Chemical and physical basics of routine formaldehyde fixation. J. of Maxxillo facial Pathology 16(3):400-405 (2012).

(56) References Cited

OTHER PUBLICATIONS

Troll et al. Structural Variation Detection by Proximity Ligation from Formalin-Fixed, Paraffin-Embedded Tumor Tissue. J Mol Diagn. 21(3):375-383 (2019).
U.S. Appl. No. 16/053,610 Office Action dated May 1, 2019.
Constans. Beyond Sanger: Toward the $1,000 Genome—The Scientist—Magazine of the Life Sciences. The Scientist. Jun. 30, 2003; 17(13):36.
Delpech et al., DNA extraction assays from formalin fixed tissues: Paternity testing from a 3-week-old embryo. International Congress Series 1261:471-472 (2004).
Han et al., Trypsin and Reduction Method to Prepare DNA from FormalinFixed and Paraffin Embedded Samples for Methylation Analysis. Histopathology 54(6): 773-775 (2009).
Jansen, et al. Nucleosome Positioning in *Saccharomyces cerevisiae*. Microbiology and Molecular Biology Reviews, Jun. 2011, pp. 301-320.
Lin et al., High-quality genomic DNA extraction from formalin-fixed and paraffin-embedded samples deparaffinized using mineral oil. Anal Biochem 395(2):265-267 (2009).
PCT/US2014/014184 International Preliminary Reporton Patentability dated Aug. 13, 2015.
PCT/US2014/014184 International Search Report dated Apr. 23, 2014.
Rodriguez et al., DNA extraction from formalin fixed franciscana tissues. Latin American Journal of Aquatic Mammals 1(1):123-128 (2000).
U.S. Appl. No. 16/128,297 Non-Final Office Action dated Nov. 18, 2020.
U.S. Appl. No. 16/053,610 Non-Final Office Action dated May 12, 2020.
Ahlfen et al., Determinants of RNA Quality from FFPE Samples. PLOS One 12: e1261 (2007).
Bennike et al., Comparing the proteome of snap frozen, RNAlater preserved, and formalin-fixed paraffin-embedded human tissue samples. EuPA Open Proteomics 1-: 9-18 (2016).
Bhudevi et al., Detection of bovine viral diarrhea virus in formalin fixed paraffin embedded tissue sections by real time RT-PCR (Taqman). J. of Virological Methods 109: 25-30 (2003).
Bresters et al., The duration of fixation influences the yield of HCV cDNA-PCR products from FFPE liver tissue. J. of Virological Methods 489: 267-272 (1994).
Cronin et al., Measurement of Gene Expression in Archival Paraffin-Embedded Tissues. Am J. of Pathology 164(1): 35-42 (2004).
Fang et al., Mapping of long-range chromatin interactions by proximity ligation-assisted ChIP-seq. Letter to the Editor—Cell Research 26: 1345-1348 (2016).
Karmakar et al., Organocatalytic Removal of Formaldehyde Adducts from RNA and DNA Bases. Nature Chemistry 7(9): 752-758 (2015).
Kawashima et al., Efficient extraction of proteins from FFPE tissues concentration of tris(hydroxymethyl)aminomethane. Clinical Proteomics 11(4): 2-6 (2014).
Macabeo-Ong et al., Effect of Duration of Fixation on Quantitative Reverse Transcription PCR Analyses. Modern Pathology 15(9): 979-987 (2001).
Masuda et al., Analysis of chemical modification of RNA from formalin-fixed samples and optimization of molecular biology applications for such samples. Nucleic Acids Research 27(22): 4436-4443(1999).
Nickerson et al., The nuclear matrix revealed by eluting chromatin from cross-linked nucleus. Proc. Natl. Acad. Sci 94: 4446-4450 (1997).
Potluri et al., Genomic DNA extraction methods using FFPE tissue. Analytical Biochemistry 486: 17-23 (2015).
Sato et al., Comparison of the DNA Extraction Methods for PCR Amplification from FFPE Tissues. Diagnostic Molecular Pathology 10(4): 265-271 (2001).
Srinivasan et al., Effect of fixatives and tissue processing on the content and integrity of nucleic acids. Am. J. of Pathology 161(16): 1961 (2002).
Thavarajah et al., Chemical and physical basics of routine formaldehyde fixation. J. of Oral and Maxillofac Pathology 16(3): 400-405 (2012).
U.S. Appl. No. 16/053,610 Non-Final Office Action dated Dec. 20, 2018.
Van Beers et al., A multiplex PCR predictor for aCGH success of FFPE samples. Br. J. of Cancer 94: 333-337 (2006).
Werner et al., Effect of Formalin Tissue Fixation and Processing on Immunohistochemistry. Am J. of Surgical Pathology 24(7): 1016-1019 (2000).
Bradnam, K.R. et al. Assemblathon 2: evaluating de novo methods of genome assembly in three vertebrate species. Gigascience, 2(1):10, 2013.
Cai et al., "SATB1 packages densely looped transcriptionally active chromatin for coordinated expression of cytokine genes," Nature Genetics, 2006, vol. 38, No. 11, pp. 1278-1288.
Grunenwald et al., "Rapid, high-throughput library preparation for next-generation sequencing" 2010 Nature Methods, vol. 7. iii-iv.
Hesselberth, Jay R. et al. Global mapping of protein-DNA interactions in vivo by digital genomic footprinting, Nature Methods 6(4): 283-289 (Apr. 2009).
International Human Genome Sequencing Consortium. Finishing the euchromatic sequence of the human genome. Nature, 431(7011):931-945, Oct. 2004.
International Preliminary Report on Patentability and Written Opinion, PCT/US2014/069642, dated Jun. 23, 2016.
Kotoulas, S. et al. The chipping forecast. Special supplement to Nature Genetics vol. 21; pp. 1-6 (1999).
Maniatis, et al. Molecular Cloning: A Laboratory Manual, Cold Spring Harbor, N.Y., pp. 280-281 (1982).
Schena, M. et al. PCR applications: protocols for functional genomics. Chapter 28: Parallel analysis with biological chips. Eds. Michael A. Innis, David H. Gelfand, John J. Sninsky. Academic Press. ISBN: 0-12-372185-7. pp. 445-456 (1999).
Sewards, Richard, Combined Search and Examination Report under Sections 17 & 18(3), Great Britain PatentApplication No. GB1520448.0, dated May 31, 2016.
Syed, F. et al. Optimized library preparation method for next-generation sequencing. Application Note Abstract, Nature Methods 6:i-ii (Oct. 2009).

\* cited by examiner

PHYSICAL LINKAGE PRESERVATION IN DNA STORAGE

RELATED APPLICATIONS

This application is a 371 U.S. National Phase Application of PCT/US2016/024225, filed Mar. 25, 2016, which is hereby incorporated by reference in its entirety, and which claims the benefit of U.S. Provisional Application Ser. No. 62/138,882, filed Mar. 26, 2015, which is hereby incorporated by reference in its entirety.

BACKGROUND

A critical component in making use of DNA is preserving the integrity of DNA information of isolated DNA subject to a DNA damaging agent. Although DNA is a relatively stable molecule, the integrity of DNA is subject to environmental factors and particularly time. The presence of nuclease contamination, hydrolysis, oxidation, chemical, physical and mechanical damages represent some of the major threats to DNA preservation. The mechanical, environmental and physical factors encountered by DNA during transportation frequently leave them in fragments and potentially lose long-range information, which are critical for genomic analysis. Existing methods for preserving DNA information mostly delay the decay of DNA but provide little protection to DNA damage over time, especially when fragmentation occurs. As such, it remains challenging to effectively preserve DNA in an easy and economic fashion.

SUMMARY

Disclosed herein are methods, compositions, and kits related to preserving and/or storing nucleic acid molecules, such as nucleic acid molecules in DNA complexes or chromatin aggregates, such as reconstituted chromatin. In particular, methods, compositions, systems and kits relate to storage or recovery of nucleic acid samples such that nucleic acid physical linkage information is preserved.

A persisting challenge of nucleic acid preservation and/or storage is to maintain the quality (e.g. long-range information) and quantity (e.g. recovery yield after storage) of nucleic acids over a long time. The present disclosure provides methods, compositions and kits for preserving physical linkage information of isolated DNA subject to a DNA damage, and identifying a nucleic acid preservative.

Provided herein are methods of preserving physical linkage information in an isolated nucleic acid sample subjected to degradation. Embodiments of the methods comprise the steps of: contacting the nucleic acid sample to a population of nucleic acid binding moieties to form at least one nucleic acid complex; subjecting the sample to degradation; and sequencing the nucleic acid sample; wherein the sample is protected from degradation such that physical linkage information is preserved. Following are a number of aspects of the herein disclosed methods which can be incorporated independently or in any combination thereof. The population of nucleic acid binding moieties comprises polypeptides. The population of nucleic acid binding moieties comprises nucleic acid binding proteins. The population of nucleic acid binding moieties comprises histones. The population of nucleic acid binding moieties comprises nanoparticles. Contacting the nucleic acid sample to a population of nucleic acid binding moieties comprises reconstituting chromatin on the nucleic acid sample. The at least one nucleic acid complex comprises a single nucleic acid molecule prior to subjecting the sample to degradation. The nucleic acid sample is contacted to a crosslinking agent following contacting to the population of nucleic acid binding moieties. The crosslinking agent comprises formaldehyde. The degradation introduces at least one double-strand break into the sample. The degradation comprises nonenzymatic degradation. The degradation comprises sequence-independent nonenzymatic degradation. The degradation comprises oxidation. The degradation comprises UV radiation. The degradation comprises hydrolysis. The degradation comprises uncooled incubation. The degradation comprises incubation at room temperature. The degradation comprises enzymatic degradation. The degradation comprises sequence-independent enzymatic degradation. Analyzing comprises probing using a first probe able to anneal to a first DNA segment and a second probe able to anneal to a second DNA segment. Analyzing comprises amplifying a fragment of the isolated nucleic acid sample. Analyzing comprises binding a fragment of the isolated nucleic acid sample to an array. Analyzing comprises cloning a fragment of the isolated nucleic acid sample into a host cell. Analyzing comprises sequencing at least a portion of the isolated nucleic acid sample. Sequencing the sample comprises enzymatic cleavage to expose internal segment ends for labeling. The labeling comprises tagging internal segment ends. The tagging comprises attaching oligos such that exposed ends of a DNA complex are commonly tagged, and such that different complexes are differentially tagged relative to one another. The labeling comprises ligating a first exposed end of a nucleic acid in a complex to a second exposed end of the nucleic acid in the complex. Sequencing the sample comprises labeling internal segment ends. The labeling comprises tagging internal segment ends. The tagging comprises attaching oligos such that exposed ends of a DNA complex are commonly tagged, and such that different complexes are differentially tagged relative to one another. The labeling comprises ligating a first exposed end of a nucleic acid in a complex to a second exposed end of the nucleic acid in the complex. Sequencing the sample comprises contacting the population of nucleic acid binding moieties to a protease. The protease comprises proteinase K. The protection comprises an increase in nucleic acid fragment size N50 of at least 2× relative to an unprotected sample subjected to the degradation. The protection comprises an increase in nucleic acid fragment size N50 of at least 5× relative to an unprotected sample subjected to the degradation. The protection comprises an increase in nucleic acid fragment size N50 of at least 50× relative to an unprotected sample subjected to the degradation. The protection comprises an increase in assembled contig sequence N50 of at least 2× relative to an unprotected sample subjected to the degradation. The protection comprises an increase in assembled contig sequence N50 of at least 5× relative to an unprotected sample subjected to the degradation. The protection comprises an increase in assembled contig sequence N50 of at least 50× relative to an unprotected sample subjected to the degradation. The protection comprises an increase in assembled scaffold sequence N50 of at least 2× relative to an unprotected sample subjected to the degradation. The protection comprises an increase in assembled scaffold sequence N50 of at least 5× relative to an unprotected sample subjected to the degradation. The protection comprises an increase in assembled scaffold sequence N50 of at least 50× relative to an unprotected sample subjected to the degradation. The preceding aspects are separable from one another in various aspects of the disclosure herein, and are in some cases not mutually exclusive. Rather, they are incorporated individually or in any combination thereof into the disclosure herein.

Provided herein are methods for preserving physical linkage information of isolated DNA. In some embodiments, the methods comprise the steps of: a) contacting the isolated DNA to a DNA binding agent to form at least one DNA complex comprising a single DNA molecule and at least one DNA binding agent, b) contacting the DNA complex to a cross-linking agent, c) subjecting the DNA complex to degradation, d) cleaving the single DNA molecule into a first segment having a first exposed DNA end and a second segment having a second exposed DNA end, e) adding label information to the first exposed DNA end and the second exposed DNA end, such that label information identifies the first segment and the second segment as arising from the single DNA molecule, and f) analyzing at least a portion of the labeled first segment and the labeled second segment, such that label information relevant to physical linkage information is obtained, such that sequencing reads comprising the labeling information are obtained. Following are a number of aspects of the herein disclosed methods which can be incorporated separately, independently or in any combination thereof. Analyzing comprises sequencing. Sequencing is performed at least 6 months after contacting the DNA complex to the cross-linking agent, and wherein the DNA complex is subjected to DNA damage prior to sequencing. The non-complexed DNA molecules are removed prior to sequencing. The DNA damage results from contact to an enzyme. The enzyme is a restriction endonuclease. The DNA damage results from contact to a nonenzymatic agent. The DNA damage results from a DNA damaging agent comprising hydrolysis, oxidation, damage from enzymes, fragmentation, degradation, decay, mechanical forces, ultraviolet light and/or shearing. The DNA damage results from degradation over time. The non-enzymatic DNA damaging results from storage of the DNA complex. The storage comprises room-temperature storage. The storage comprises cold storage, such as storage at 4° C. The storage comprises freezing, such as storage at −20° C. or −80° C. The storage comprises cryopreservation. The DNA binding agent is a protein. The protein is a nuclear protein. The nuclear protein is a histone. The DNA binding agent is a nanoparticle. The methods comprise discarding DNA not bound to a DNA binding agent prior to adding label information. Analyzing comprises sequencing. Sequencing comprises sequencing at least a portion of the labeled first segment and the labeled second segment, such that sequencing reads comprising the labeling information are obtained. Analyzing comprises probing using a first probe able to anneal to a first DNA segment and a second probe able to anneal to a second DNA segment. Analyzing comprises binding to an array. Analyzing comprises amplification of a larger fragment. Analyzing comprises cloning into a plasmid or library. The methods comprise sequencing a first junction formed by the first exposed DNA end and the label information and sequencing a second junction formed by the second exposed DNA end and the label information. Methods comprise sequencing a portion of a first labeled fragment and a portion of a second labeled fragment. The methods comprise discarding DNA not bound in a DNA complex prior to sequencing the first junction. The methods comprise assigning the first segment and the second segment to a common phase or common molecule. The label information comprises oligonucleotide sequence information that is common to the DNA complex. The label information added to the first exposed DNA end comprises sequence of the single DNA molecule that is distal to the first segment. The label information added to the second exposed DNA end comprises sequence of the single DNA molecule that is distal to the second segment. Analyzing is performed at least 12 months after contacting the DNA complex to the cross-linking agent. Analyzing is performed at least 24 months after contacting the DNA complex to the cross-linking agent. The preceding aspects are not mutually exclusive and can be incorporated individually or in any combination thereof.

Provided herein are methods of identifying a nucleic acid preservative comprising the steps of: a) separating a nucleic acid sample into a first portion and a second portion; b) contacting the first portion and the second portion to a DNA binding agent having a first binding agent parameter set; c) contacting the first portion and the second portion to a crosslinking agent having a first crosslinking parameter set; d) contacting the first portion to a DNA degrading agent; e) contacting the first portion and the second portion to dsDNA cleaving agent to generate a first exposed end and a second exposed end in each portion; f) labeling exposed ends of the first portion and the second portion; g) sequencing labeled exposed ends of the first portion and the second portion to generate a first portion sequence assembly and a second portion sequence assembly; h) evaluating relative quality of the first portion sequence assembly and the second portion sequence assembly; i) changing at least one of the first binding agent parameter set and the first crosslinking parameter set; j) repeating steps a) through h), replacing at least one of the first binding agent parameter set and the first crosslinking parameter set with a second binding agent parameter set and a second crosslinking parameter set; and k) selecting the parameter set yielding a greater relative quality of a sequence assembly. Following are a number of aspects of the herein disclosed methods which can be incorporated independently or in any combination thereof. The DNA binding agent is a protein. The protein is a nuclear protein. The nuclear protein is a histone. The DNA binding agent is a nanoparticle. The DNA degrading agent is an enzyme. The enzyme is a restriction endonuclease. The DNA degrading agent is a nonenzymatic agent. The DNA degrading agent is a DNA damaging agent selected from the list consisting of hydrolysis, oxidation, damage from enzymes, fragmentation, degradation, decay, mechanical forces, ultraviolet light, and/or shearing. The DNA degrading agent comprises degradation over time. The methods comprise discarding DNA not bound to a DNA binding agent prior to adding label information. The methods comprise sequencing a first junction formed by the first exposed DNA end and the label information and sequencing a second junction formed by the second exposed DNA end and the label information. The methods comprise discarding DNA not bound in a DNA complex prior to sequencing the first junction. The methods comprise assigning the first segment and the second segment to a common phase or common molecule. The label information comprises oligonucleotide sequence information that is common to the DNA complex. The label information added to the first exposed DNA end comprises sequence of the single DNA molecule that is distal to the first segment. The label information added to the second exposed DNA end comprises sequence of the single DNA molecule that is distal to the second segment. The label information is added at least 12 months after contacting the DNA complex to the cross-linking agent. The label information is added at least 24 months after contacting the DNA complex to the cross-linking agent. The preceding aspects are not mutually exclusive and can be incorporated individually or in any combination thereof.

Provided herein are methods of isolating a phase-informative or physical linkage-informative fraction of a fragmented nucleic acid sample, comprising the steps of: contacting the sample to a population of nucleic acid binding moieties to form at least one nucleic acid complex, wherein the nucleic acid binding moieties bind to nucleic acid fragments over a phase-informative or physical linkage-informative length; removing unbound nucleic acid fragments; and sequencing a portion of said nucleic acid fragments over a phase-informative or physical linkage-informative length. Following are a number of aspects of the herein disclosed methods which can be incorporated independently or in any combination thereof. Sequencing a portion of said at least one nucleic acid complex comprises: cleaving at least one phase-informative or physical linkage-informative fragment to form a first segment and a second segment, labeling an end of said first fragment and labeling an end of said second fragment such that said labeling conveys physical linkage information, sequencing across a first fragment labeled end and a second fragment labeled end, and assigning sequence reads having common labeling physical linkage information to a common phase or common molecule of a sequence assembly. The fragmented nucleic acid sample is age-degraded. The age-degraded sample is stored for at least 1 year prior to said sequencing. The fragmented nucleic acid sample is temperature-degraded. The temperature-degraded sample is held at room-temperature for at least 3 days. The fragmented nucleic acid sample is chemically degraded. The sample is chemically degraded by a reagent having endonuclease activity. The sample is chemically degraded by a reagent that catalyzes phosphodiester backbone breakage. The fragmented nucleic acid sample is degraded by contact to UV radiation. The preceding aspects are not mutually exclusive and can be incorporated individually or in any combination thereof.

Provided herein are methods of preserving physical linkage information in a nucleic acid sample likely to undergo double-strand breakage comprising the steps of: cleaving the nucleic acid sample so as to expose at least one internal double-strand end; labeling the at least one internal double-strand end so as to preserve physical linkage information; and subjecting the nucleic acid sample to conditions likely to comprise double-strand breakage. Following are a number of aspects of the herein disclosed methods which can be incorporated independently or in any combination thereof. Cleaving the nucleic acid so as to expose at least one internal double strand end comprises: contacting the nucleic acid sample to a plurality of DNA binding moieties such that an individual nucleic acid of said sample comprising a first segment and a second segment is bound such that the first segment and the second segment are held together independent of their common phosphodiester backbone; and cleaving the individual nucleic acid between the first segment and the second segment. Labeling the at least one internal double-strand end so as to preserve physical linkage information comprises ligating a first nonadjacent exposed end of the individual nucleic acid to the first segment, and ligating a second nonadjacent exposed end of the individual nucleic acid end to the second segment. Labeling the at least one internal double-strand end so as to preserve physical linkage information comprises attaching oligonucleotides having a common sequence to the first segment and the second segment. The likely double-strand breakage comprises age-degradation. The likely double-strand breakage comprises age-degradation for at least 1 year prior to said sequencing. The likely double-strand breakage comprises temperature-degradation. The likely double-strand breakage comprises temperature-degradation at room-temperature for at least 3 days. The likely double-strand breakage comprises chemical degradation. The likely double-strand breakage comprises chemical degradation by a reagent having endonuclease activity. The likely double-strand breakage comprises chemical degradation by a reagent that catalyzes phosphodiester backbone breakage. The likely double-strand breakage comprises degradation by contact to UV radiation. The preceding aspects are not mutually exclusive and can be incorporated individually or in any combination thereof.

Provided herein are methods of preserving physical linkage information in a nucleic acid sample likely to undergo double-strand breakage comprising the steps of: contacting the nucleic acid sample to a plurality of DNA binding moieties such that an individual nucleic acid of said sample comprising a first segment and a second segment is bound such that the first segment and the second segment are held together independent of their common phosphodiester backbone; and subjecting the nucleic acid sample to conditions likely to comprise double-strand breakage. Following are a number of aspects of the herein disclosed methods which can be incorporated independently or in any combination thereof. The methods comprise sequencing the nucleic acid sample. Sequencing the nucleic acid sample comprises: cleaving the individual nucleic acid between the first segment and the second segment to expose at least one internal double-strand end, and labeling the at least one internal double-strand end so as to preserve physical linkage information. Labeling the at least one internal double-strand end so as to preserve physical linkage information comprises ligating a first nonadjacent exposed end of the individual nucleic acid to the first segment, and ligating a second nonadjacent exposed end of the individual nucleic acid end to the second segment. Labeling the at least one internal double-strand end so as to preserve physical linkage information comprises attaching oligonucleotides having a common sequence to the first segment and the second segment. The likely double-strand breakage comprises age-degradation. The likely double-strand breakage comprises age-degradation for at least 1 year prior to said sequencing. The likely double-strand breakage comprises temperature-degradation. The likely double-strand breakage comprises temperature-degradation at room-temperature for at least 3 days. The likely double-strand breakage comprises chemical degradation. The likely double-strand breakage comprises chemical degradation by a reagent having endonuclease activity. The likely double-strand breakage comprises chemical degradation by a reagent that catalyzes phosphodiester backbone breakage. The likely double-strand breakage comprises degradation by contact to UV radiation. The preceding aspects are not mutually exclusive and can be incorporated individually or in any combination thereof.

Provided herein are kits for preserving physical linkage information of isolated DNA comprising reagents for DNA extraction, at least one DNA binding agent, and at least one DNA cross-linker, wherein the kit reagents do not require refrigeration. Following are a number of aspects of the herein disclosed kits which can be incorporated independently or in any combination thereof. The DNA extraction reagents are for high molecular weight DNA extraction. The DNA binding agent is a protein. The protein is a nuclear protein. The nuclear protein is a histone. The DNA binding agent is a nanoparticle. The DNA cross-linker is formaldehyde. The reagents are stable at room temperature for a least 1 month. The reagents are stable at room temperature for at least 6 months. The reagents are stable at room temperature for at least 12 months. The preceding aspects are not mutually exclusive and can be incorporated individually or in any combination thereof.

Provided herein are methods of identifying a nucleic acid preservative comprising the steps of: a) contacting a nucleic acid sample to a DNA binding agent having a first binding agent parameter set; b) contacting the nucleic acid sample to a crosslinking agent having a first crosslinking parameter set; c) contacting the nucleic acid sample to a DNA degrading agent; d) contacting the nucleic acid sample to dsDNA cleaving agent to generate a first exposed end and a second exposed end; e) labeling exposed ends of the nucleic acid sample; f) sequencing labeled exposed ends of the nucleic acid sample to generate a the nucleic acid sample sequence assembly; g) evaluating relative quality of the nucleic acid sample sequence assembly; h) changing at least one of the first binding agent parameter set and the first crosslinking parameter set; i) repeating steps a) through h), replacing at least one of the first binding agent parameter set and the first crosslinking parameter set with a second binding agent parameter set and a second crosslinking parameter set; and j) selecting the parameter set yielding a greater relative quality of a sequence assembly. Following are a number of aspects of the herein disclosed methods which can be incorporated independently or in any combination thereof. The DNA binding agent is a protein. The protein is a nuclear protein. The nuclear protein is a histone. The DNA binding agent is a nanoparticle. The DNA degrading agent is an enzyme. The enzyme is a restriction endonuclease. The DNA degrading agent is a nonenzymatic agent. The DNA degrading agent is a DNA damaging agent comprising: hydrolysis, oxidation, damage from enzymes, fragmentation, degradation, decay, mechanical forces, ultraviolet light, and/or shearing. The DNA degrading agent comprises degradation over time. The methods comprise discarding DNA not bound to a DNA binding agent prior to adding label information. The methods comprise sequencing a first junction formed by the first exposed DNA end and the label information and sequencing a second junction formed by the second exposed DNA end and the label information. The methods comprise discarding DNA not bound in a DNA complex prior to sequencing the first junction. The methods comprise assigning the first segment and the second segment to a common phase or common molecule. The label information comprises oligonucleotide sequence information that is common to the DNA complex. The label information added to the first exposed DNA end comprises sequence of the single DNA molecule that is distal to the first segment. The label information added to the second exposed DNA end comprises sequence of the single DNA molecule that is distal to the second segment. The label information is added at least 12 months after contacting the DNA complex to the cross-linking agent. The label information is added at least 24 months after contacting the DNA complex to the cross-linking agent.

Provided herein are methods of isolating a size-threshold selected fraction of a fragmented nucleic acid sample. Some such methods comprise the steps of contacting the sample to a population of nucleic acid binding moieties to form at least one nucleic acid complex, wherein the nucleic acid binding moieties bind to nucleic acid fragments over a threshold size; removing unbound nucleic acid fragments; and analyzing a portion of said nucleic acid fragments over a size-threshold. Various aspects of these methods optionally comprise in some cases one or more of the elements recited below, alone or in combination. Analyzing comprises probing using a first probe able to anneal to a first DNA segment and a second probe able to anneal to a second DNA segment. Analyzing comprises binding to an array. Analyzing comprises amplification of a larger fragment. Analyzing comprises cloning into a plasmid or library. Analyzing a portion of said at least one nucleic acid complex comprises cleaving at least one size-selected fragment to form a first segment and a second segment, tagging an end of said first fragment and tagging an end of said second fragment such that said tagging conveys physical linkage information, sequencing across a first fragment tagged end and a second fragment tagged end, and assigning sequence reads having common tagging physical linkage information to a common phase or common molecule of a sequence assembly.

Variously, the threshold size is at least 140 bp. The threshold size is at least 200 bp. The threshold size is at least 500 bp. The threshold size is at least 1000 bp. The threshold size is a minimum size necessary for a nucleic acid to bind to a nucleosome. The fragmented nucleic acid sample is age-degraded. The age-degraded sample is stored for at least 1 year prior to said sequencing. The fragmented nucleic acid sample is temperature-degraded. The temperature-degraded sample is held at room-temperature for at least 3 days. The fragmented nucleic acid sample is chemically degraded. The fragmented nucleic acid sample is chemically degraded by a reagent having endonuclease activity. The fragmented nucleic acid sample is chemically degraded by a reagent that catalyzes phosphodiester backbone breakage. The fragmented nucleic acid sample is degraded by contact to UV radiation. Elements recited above and elsewhere herein are separably and in combination descriptive of aspects of the methods described herein.

Disclosed herein are methods of preserving physical linkage information of isolated DNA subject to a DNA damaging agent. Some such methods comprise contacting the isolated DNA to a DNA binding agent to form at least one DNA complex comprising a single DNA molecule and at least one DNA binding agent, contacting the DNA complex to a cross-linking agent, subjecting the DNA complex to a DNA cleaving agent to cleave the single DNA molecule into a first segment having a first exposed DNA end and a second segment having a second exposed DNA end, adding tag information to the first exposed DNA end and the second exposed DNA end, such that tag information identifies the first segment and the second segment as arising from the single DNA molecule, and sequencing at least a portion of the tagged first segment and the tagged second segment, such that sequencing reads comprising the tagging information are obtained, wherein the sequencing is performed at least 6 months after contacting the DNA complex to the cross-linking agent, and wherein the DNA complex is subjected to DNA damage such as sequence-independent DNA damage prior to sequencing. Often, the DNA damage comprises nonspecific DNA damage and is independent of or in addition to DNA manipulation pursuant to preparing a nucleic acid sample for sequencing through library formation. In some examples, the DNA damage results from contact to an enzyme. In some aspects, the enzyme is a restriction endonuclease. More often, the DNA damage results from contact to a nonenzymatic agent. In some aspects, the DNA damage results from a DNA damaging agent comprising: hydrolysis, oxidation, damage from enzymes, fragmentation, degradation, decay, mechanical forces, ultraviolet light, and/or shearing. In some aspects, the DNA damage results from degradation over time. In some aspects, the non-enzymatic DNA damaging results from storage of the DNA complex. In some aspects, the storage comprises room-temperature storage. In some aspects, the DNA complex is stored for at least 1 week, at least 1 month, at least 6 months, or at least 1 year. In many cases, the nucleic acids are considered to be 'subjected to degradation' when the N50 value for nucleic acid fragment lengths of the sample is substantially reduced. Substantial reduction in N50 is in some cases a reduction to no more than 0.5, 0.5, 0.4, 0.3, 0.2. 0.1, 0.05, 0.01, 0.005, 0.001, 0.0005, 0.0001, one ten-thousandth, one hundred thousandth, one millionth or less than one millionth of the N50 of the fragments in the starting sample.

In some aspects, the DNA binding agent is a protein. In some aspects, the protein is a nuclear protein. In some aspects, the nuclear protein is a histone. In some aspects, the histone protein comprises H2 histone, an H3 histone and an H4 histone. In some aspects, the DNA binding agent is a type I topoisomerase or a type II topoisomerase. In some aspects, the DNA binding agent is a non-polypeptide. In some aspects, the DNA binding agent is a nanoparticle. In some aspects, the nanoparticle is magnetic. In some aspects, the nanoparticle is positively charged. In some aspects, the comprises a platinum-based nanoparticle, a magnetic-based nanoparticle, a positively charged nanoparticle, an amine-coated nanoparticle, a gold-containing nanoparticle, a silver-containing nanoparticle, a DNA intercalator and any derivatives thereof, a copper-containing nanoparticle, and combinations thereof. In some aspects, the method comprising discarding DNA not bound to a DNA binding agent prior to adding tag information. In some aspects, unbound nucleic acids are discarded prior to sequencing the nucleic acid sample. In some aspects, at least 95% of nucleic acids greater than 200 bp in length are retained. In some aspects, at least 95% of nucleic acids less than 200 bp in length are discarded. In some aspects, at least 95% of nucleic acids greater than 1000 bp in length are retained. In some aspects, at least 95% of nucleic acids greater than 1000 bp in length are discarded. In some aspects, the unbound nucleic acids are separated and discarded by methods selected from the group consisting of exonuclease digestion, antibody precipitation, washing, eluting through a purification column and eluting through a magnetic column. In some aspects, the sequencing comprises targeted sequencing of a locus or whole-sample sequencing. In some aspects, the sequencing comprises attaching tags to internal regions of nucleic acids reconstituted chromatin. In some aspects, the tags are oligomeric tags. In some aspects, the tags are selected from a cluster-specific molecular tag or a barcode. In some aspects, the tags are generated by cleaving the nucleic acids in the reconstituted chromatin, labeling cleavage sites, and religating at least one cleavage site, so as to generate a labeled cleavage site comprising ligated ends that were not previously attached at the marked site. In some aspects, the labeling cleavage sites comprises adding a biotin agent to the cleavage sites. In some aspects, the method comprising sequencing a first junction formed by the first exposed DNA end and the tag information and sequencing a second junction formed by the second exposed DNA end and the tag information. In some aspects, the method comprising discarding DNA not bound in a DNA complex prior to sequencing the first junction. In some aspects, the method comprising assigning the first segment and the second segment to a common phase. In some aspects, the method comprising assigning the first segment and the second segment to a common molecule. In some aspects, the tag information comprises oligonucleotide sequence information that is common to the DNA complex. In some aspects, the tag information added to the first exposed DNA end comprises sequence of the single DNA molecule that is distal to the first segment. In some aspects, the tag information added to the second exposed DNA end comprises sequence of the single DNA molecule that is distal to the second segment. In some aspects, the tag information is added at least 12 months after contacting the DNA complex to the cross-linking agent. In some aspects, the tag information is added at least 24 months after contacting the DNA complex to the cross-linking agent. In some aspects, the tag information is added at least 1 year, 2 years, 3 years, 4 years, 5 years, 6 years, 7 years, 8 years, 9 year, 10 years, 100 years, 1000 years, or more, after contacting the DNA complex to the cross-linking agent. In some aspects, the cross-linking agent is selected from the group consisting of formaldehyde, psoralen, UV light, mitomycin C, nitrogen mustard, melphalan, 1,3-butadiene diepoxide, cis diaminedichloroplatinum(II), and cyclophosphamide.

Some embodiments of these methods relate to identifying a nucleic acid preservative comprising the steps of separating a nucleic acid sample into a first portion and a second portion; contacting the first portion and the second portion to a DNA binding agent having a first binding agent parameter set; contacting the first portion and the second portion to a crosslinking agent having a first crosslinking parameter set; contacting the first portion to a DNA degrading agent; contacting the first portion and the second portion to dsDNA cleaving agent; tagging exposed ends of the first portion and the second portion; sequencing tagged exposed ends of the first portion and the second portion to generate a first portion sequence assembly and a second portion sequence assembly; evaluating relative quality of the first portion sequence assembly and the second portion sequence assembly; changing at least one of the first binding agent parameter set and the first crosslinking parameter set; repeating steps a) through h), replacing at least one of the first binding agent parameter set and the first crosslinking parameter set with a second binding agent parameter set and a second crosslinking parameter set; and selecting the parameter set yielding a greater relative quality of a sequence assembly. In some aspects, the DNA binding agent is a protein. In some aspects, the protein is a nuclear protein. In some aspects, the nuclear protein is a histone. In some aspects, the histone protein comprises H2 histone, an H3 histone and an H4 histone. In some aspects, the DNA binding agent is a type I topoisomerase or a type II topoisomerase. In some aspects, the DNA binding agent is a non-polypeptide. In some aspects, the DNA binding agent is a nanoparticle. In some aspects, the nanoparticle is positively charged. In some aspects, the nanoparticle is magnetic. In some aspects, the nanoparticle is selected from the group consisting of a platinum-based nanoparticle, a magnetic-based nanoparticle, a positively charged nanoparticle, an amine-coated nanoparticle, a gold-containing nanoparticle, a silver-containing nanoparticle, a DNA intercalator and any derivatives thereof, a copper-containing nanoparticle, and combinations thereof. In some aspects, the DNA degrading agent is an enzyme. In some aspects, the enzyme is a restriction endonuclease. In some aspects, the DNA degrading agent is a nonenzymatic agent. In some aspects, the DNA degrading agent is a DNA damaging agent comprising: hydrolysis, oxidation, damage from enzymes, fragmentation, degradation, decay, mechanical forces, ultraviolet light, and/or shearing. In some aspects, the DNA degrading agent comprises degradation over time. In some aspects, the DNA degradation is at least 1 year, 2 years, 3 years, 4 years, 5 years, 6 years, 7 years, 8 years, 9 year, 10 years, 100 years, 1000 years, or more. In some aspects, the method comprising discarding DNA not bound to a DNA binding agent prior to adding tag information. In some aspects, the method comprising sequencing a first junction formed by the first exposed DNA end and the tag information and sequencing a second junction formed by the second exposed DNA end and the tag information. In some aspects, the method comprising discarding DNA not bound in a DNA complex prior to sequencing the first junction. In some aspects, unbound nucleic acids are discarded prior to sequencing the nucleic acid sample. In some aspects, at least 95% of nucleic acids greater than 200 bp in length are retained. In some aspects, at least 95% of nucleic acids less than 200 bp in length are discarded. In some aspects, at least 95% of nucleic acids greater than 1000 bp in length are retained. In some aspects, at least 95% of nucleic acids greater than 1000 bp in length are discarded. In some aspects, the unbound nucleic acids are separated and discarded by methods selected from the group consisting of exonuclease digestion, antibody precipitation, washing, eluting through a purification column and eluting through a magnetic column. In some aspects, the sequencing comprises targeted sequencing of a locus or whole-sample sequencing. In some aspects, the sequencing comprises attaching tags to internal regions of nucleic acids reconstituted chromatin. In some aspects, the tags are oligomeric tags. In some aspects, the tags are selected from a cluster-specific molecular tag or a barcode. In some aspects, the tags are generated by cleaving the nucleic acids in the reconstituted chromatin, labeling cleavage sites, and religating at least one cleavage site, so as to generate a labeled cleavage site comprising ligated ends that were not previously attached at the marked site. In some aspects, the labeling cleavage sites comprises adding a biotin agent to the cleavage sites. In some aspects, the method comprising assigning the first segment and the second segment to a common phase. In some aspects, the method comprising assigning the first segment and the second segment to a common molecule. In some aspects, the tag information comprises oligonucleotide sequence information that is common to the DNA complex. In some aspects, the tag information added to the first exposed DNA end comprises sequence of the single DNA molecule that is distal to the first segment. In some aspects, the tag information added to the second exposed DNA end comprises sequence of the single DNA molecule that is distal to the second segment. In some aspects, the tag information is added at least 12 months after contacting the DNA complex to the cross-linking agent. In some aspects, the tag information is added at least 24 months after contacting the DNA complex to the cross-linking agent. In some aspects, the tag information is added at least 1 year, 2 years, 3 years, 4 years, 5 years, 6 years, 7 years, 8 years, 9 year, 10 years, 100 years, 1000 years, or more, after contacting the DNA complex to the cross-linking agent. In some aspects, the cross-linking agent is selected from the group consisting of formaldehyde, psoralen, UV light, mitomycin C, nitrogen mustard, melphalan, 1,3-butadiene diepoxide, cis diaminedichloroplatinum(II), and cyclophosphamide. In some aspects, the preservative is selected from formaldehyde, psoralean, mitomycin C, nitrogen mustard, melphalan, 1,3-butadiene diepoxide, cis diaminedichloroplatinum (II), and cyclophosphamide.

Descriptions of embodiments summarized herein are understood to recite elements of at least some but not all embodiments disclosed herein. Accordingly, an element recited herein is understood to relate to some claims recited or supported by the present disclosure, but is not to be imputed to claims that do not recite such element.

INCORPORATION BY REFERENCE

U.S. Patent Application Number PCT/US2015/043327, filed Jul. 31, 2015, which published Feb. 4, 2016 as International Application Publication Number WO 2016/019360, is hereby incorporated by reference in its entirety. International Publication No. WO2014/121,091, published Aug. 7, 2014 is hereby incorporated by reference in its entirety. International Publication No. WO2015/689,243, published Jun. 18, 2015 is hereby incorporated by reference in its entirety.

BRIEF DESCRIPTION OF THE DRAWINGS

FIG. 1A indicates a first step where one begins with pure, high molecular weight DNA. FIG. 1B depicts reconstitution of chromatin in vitro. Circles indicate histones FIG. 1C depicts reconstituted chromatin crosslinked using formaldehyde. Thin lines represent crosslinks. This stage is the stable end product of CMDS. FIG. 1D indicates that physical linkage information is preserved even after fragmentation through double strand breakage has occurred, because the physical linkage information of the original fragment is maintained through crosslinks. FIG. 1E-1G depicts an approach for the retrieval of long-range information. FIG. 1E depicts that the complex is cut with a restriction enzyme (e.g. MboI) and blunt-ends are generated using biotinylated nucleotide (green circles). FIG. 1F illustrates the ligation of blunt ends in dilute solution. Ligation events are indicated with asterisks. FIG. 1G illustrates the reversal of crosslinks, end-repair to remove end biotins, pulldown using streptavidin-coated beads to enrich for ligation junctions, and performing of standard library prep, paired-end sequence.

DETAILED DESCRIPTION

Figure 1:
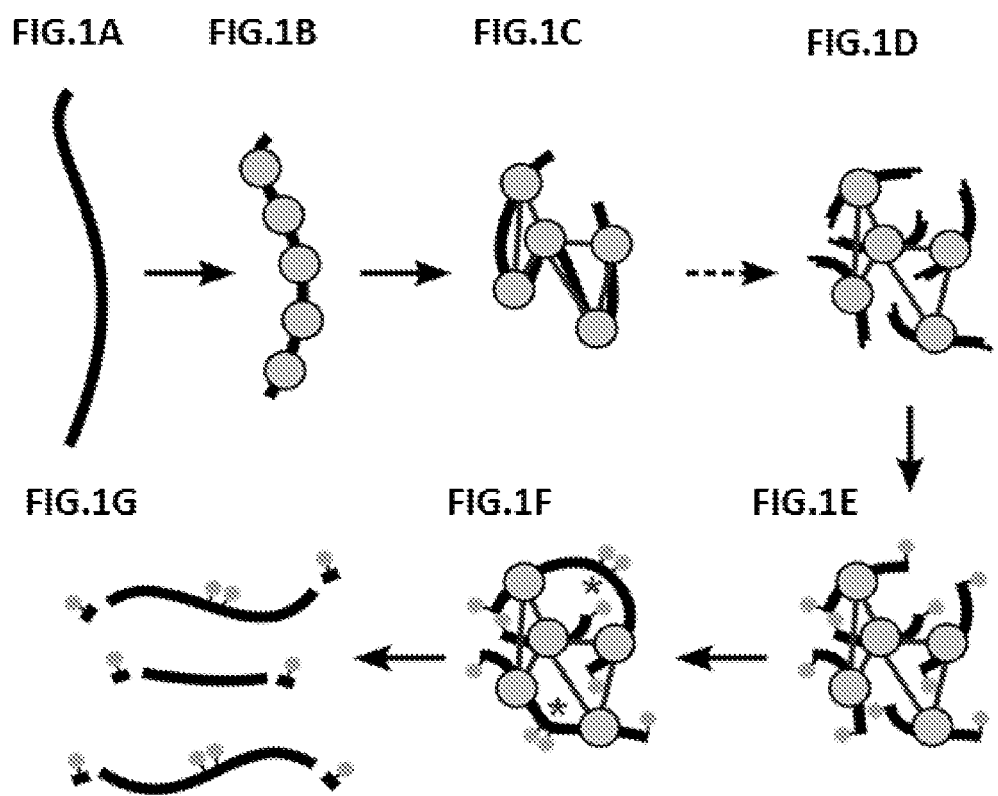
FIG. 1A-1G illustrate an exemplary crosslink-mediated DNA stabilization (CMDS) process and the retrieval of long-range information from CMDS substrates.

Though a remarkably stable molecule, DNA is subject to degradation and fragmentation by agents such as chemicals, radiation, or physical forces. These effects are potentiated by many factors but particularly time (e.g. long-term storage), physical forces from agitation (e.g. rough handling during transportation), heat, humidity, and exposure to sunlight or to other radiation during package screening or transportation.

Often, double strand breaks occur during DNA storage, causing loss of physical linkage information. Loss of physical linkage information is particularly detrimental, because it precludes a sequence assembler from determining whether, in a diploid organism sample, mutations that map to a common locus are in fact in the same allele or are present on two separate homologous alleles positioned on different strands of the diploid genome. As genome information is used for personalized medicine or for more medicinal or therapeutic purposes, assigning physical linkage information to assembled contig sequence is of increasing importance.

These challenges to the integrity of DNA are problematic as genomics technologies improve along with expansion of programs for worldwide, prolonged, historical, or large-scale studies of genomes. Such studies are imperative to understand the genomes of current human populations and individuals and their impacts on human health, as well as to preserve present genomes for future studies with ever more powerful techniques. The latter concern also overlaps with forensic interests, which seek to bank DNA samples indefinitely for later analysis and identification.

A number of downstream analyses can be used to obtain physical linkage information from a sample, and are thus harmed or complicated by loss of such information in a sample. Nucleic acid samples are often intended as templates for amplification of large fragments, for example via polymerase chain reaction ("PCR") using primers known to anneal adjacent to a region of interest. PCR relies upon the presence of a template from which one generates multiple amplicon nucleic acid molecules. Amplification relies upon two annealing sites (or an annealing site and the reverse complement of a second annealing site) being physically linked to one another on a single molecule. Accordingly, loss of physical linkage between primer annealing sites complicates analyses comprising PCR amplification.

Similarly, cloning a fragment into a cellular host so that it may be replicated, amplified, expressed or manipulated transgenically, is greatly facilitated by having a single molecule as a starting material. Loss of physical linkage for a fragment (that is, cleavage of that fragment) complicates cloning and necessitates multiple additional steps in fragment assembly.

Alternately, some analyses approaches require the preservation of physical proximity but do not require that a first segment and a second segment of a nucleic acid remain physically linked by their phosphodiester backbone. For example, one may assay for co-localization of probes to a first nucleic acid segment and a second nucleic acid segment so as to determine whether they exist on a common molecule in an un-degraded sample. Preservation of physical linkage facilitates this analysis, but is not necessary for such analysis. Assembling the molecule into a reconstituted chromatin complex such that the first segment and the segment are bound independent of their common phosphodiester backbone, for example similarly facilitates such an analysis. Even in the event of cleavage of their common phosphodiester backbone, physical proximity information for the first segment and the second segment is preserved such that probing the complex with a first and a second probe will indicate whether the first fragment and the second fragment exist on a common molecule in the original sample.

Sequencing is another analysis that benefits from preservation of physical linkage information but does not require preservation of physical linkage, or even of physical proximity. Preservation of physical linkage facilitates sequencing, but so do other methods disclosed herein and known to one of skill in the art. Preservation of physical proximity, for example, facilitates sequencing because fragments held in proximity are readily end labeled so as to convey physical linkage information. Exposed internal ends are labeled using oligonucleotide tags that allow adjacent fragment sequence to be mapped to a common molecule. Alternately or in combination, exposed ends are ligated to one another at random, so as to generate read pairs wherein sequence on either side of a marked ligation event is mapped to a common molecule. Even in the absence of physical proximity, sequence analysis is facilitated if a nucleic acid sample is treated so as to add physical proximity markers prior to loss of the physical proximity information. That is, assembly of reconstituted chromatin on a nucleic acid molecule, exposure of internal double-strand ends and labeling of these exposed ends via cross-ligation or via tagging using common oligonucleotides, if performed prior to subjecting the sample to degradation that may jeopardize or cause loss of physical linkage among segments of a molecule.

It is for all of these reasons that simple, affordable technologies for the long-term preservation of physical linkage information encoded by DNA has become a critical necessity for the field. The methods disclosed herein are useful in many fields including, by way of non-limiting example, forensics, agriculture, environmental studies, renewable energy, epidemiology or disease outbreak response, and species preservation.

Among the various classes of DNA damage, fragmentation is the most problematic. The loss of contiguity affects researchers' ability to assemble and compare genomes, phase variation, and characterize large structural variants, all of which are analyses of increasing interest in genomics and particularly in clinical genomics.

The preservation of contiguity is of importance to modern clinical genomics and studies of human populations in part because it offers stability in transport. Only rarely in such studies are samples collected near to the area where they will be sequenced. More often, and increasingly so as large-scale studies become more prevalent, samples are collected from diverse locations and shipped to a distant central analysis facility. The mechanical, environmental, and energetic forces encountered by DNA on these journeys frequently leave them in pieces, robbing the investigators of valuable long-range information. Better preservation of such samples in transit will enable more powerful, informative, and comprehensive genomics research.

Existing methods for the stabilization of DNA for storage or transit are often either costly and effective (e.g. liquid nitrogen) or affordable but imperfect (e.g. FTA cards). These methods only slow the decay of the DNA they protect but, crucially, do little to preserve the information content when a sample is subjected to degradation such as that which leads to double strand breaks. Long-range contiguity information is vital for many important avenues of genomic study including de novo assembly, phasing, and structural variant analysis. Consequently, it is critical that DNA integrity or the long-range information be preserved.

Described herein are methods, compositions, systems and kits for preserving physical linkage information of isolated DNA. Methods, compositions, systems and kits herein act such that physical linkage information for a given molecule is preserved in the event that the molecule is cleaved, for example due to nonenzymatic nucleic acid degradation such as may occur during long term storage or during storage or shipment without refrigeration. Through the benefits of the disclosure herein, if a nucleic acid sample is subject to a DNA damaging agent, the physical linkage information of the sample is preserved. Preservation of physical linkage information is accomplished physically, by protecting the physical molecules from degradation or by reducing the extend of physical breakage. Alternately or in combination, the disclosure herein provides for protection such that even when double strand breaks are introduced into a nucleic acid subject to degradation such that a first segment and a second segment of a common DNA molecule are no longer physically linked to one another, the physical linkage information is partially, largely or completely preserved.

In some such embodiments, a sample subject to chromatin reassembly or otherwise protected through a method, composition or kit disclosed herein is protected from physical linkage information loss such that the N50 of a set of contigs and/or scaffolds generated by sequencing the protected sample is greater than the N50 of a comparable unprotected sample. The N50 of contigs and/or scaffolds generated by sequencing the protected sample is in some cases 2×, 3×, 4×, 5×, 6×, 7×, 8×, 9×, 10×, 15×, 20×, 25×, 30×, 35×, 40×, 45×, 50×, 100×, 500×, 1000× or greater than 1000× improved relative to an unprotected sample. Alternately or in combination, some embodiments provide for the protection of a sample such that a sample subject to chromatin reassembly or otherwise protected through a method, composition or kit disclosed herein is protected from physical linkage information loss such that the N50 of a set of nucleic acid molecules in the sample is greater than the N50 of a comparable unprotected sample. The N50 of nucleic acid molecules protected is in some cases 2×, 3×, 4×, 5×, 6×, 7×, 8×, 9×, 10×, 15×, 20×, 25×, 30×, 35×, 40×, 45×, 50×, 100×, 500×, 1000× or greater than 1000× improved relative to an unprotected sample. An unprotected sample is concurrently subjected to the damaging treatment in some cases, or alternately is a reference sample or reference contig and/or scaffold assembly dataset predicted or determined from prior efforts.

Embodiments relate to methods, compositions, systems and kits for preserving DNA physical linkage information by binding a nucleic acid molecule in a complex, such as literal reconstituted chromatin of exogenously provided histones onto individual chromatin, or reconstituted chromatin more broadly defined as a nucleic acid provided with a population of binding moieties such as polypeptides or even non polypeptide moieties such as nanoparticles or other nucleic acid binding agents. Some embodiments comprise contacting the complex to a crosslinking agent so as to stabilize at least one nucleic acid-protein complex or other reconstituted chromatin complex such that a first segment and a second segment of a nucleic acid molecule are held together independent of their common phosphodiester backbone, such that the complex preserves physical linkage information that may otherwise resulted from double-strand breaks. Alternately or in combination, DNA complexes are formed without the addition of a cross-linking agent, using nuclear or otherwise DNA-binding proteins, or non-polypeptide DNA binding agent such as nanoparticles.

Some disclosed methods, compositions, systems and kits relate to preserving DNA information integrity and storing DNA over time. Physical linkage information is preserved in various embodiments by physically preventing strand breakage, by preventing the loss of physical linkage information that otherwise accompanies strand breakage, by labeling nucleic acid molecules such that physical linkage information is preserved despite breakage, or by a combination of these approaches.

Loss of physical linkage information and/or physical linkage information is avoided or reduced by physically preventing or reducing nucleic acid breakage. Loss of phase information and/or physical linkage information is avoided or reduced by holding a first segment and a second segment in physical proximity independent of their phosphodiester backbone. Alternately or in combination, loss of phase information and/or physical linkage information is avoided or reduced by labeling a first segment and a second segment using a common or reciprocally complementary tag such that, upon loss of physical proximity information and loss of a common phosphodiester backbone tether, sequencing tag information that is affixed to a first segment and a second segment is sufficient to identify the two segments as sharing a common phase or common molecule in the original, un-degraded sample. Additionally or alternatively, labeling is achieved by ligation of a first segment to a second segment, wherein the second segment is non-adjacent to the first segment, though they are physically linked on the same original DNA molecule.

Nucleic acid degradation arises from a number of diverse sources. Contemplated herein is protection from DNA degradation of a number of types, in particular DNA degradation that results in the introduction of double-strand breaks such as those that result in loss of physical linkage between a first segment and a second segment on an original common molecule in a nucleic acid sample. Of particular significance is nonenzymatic DNA degradation, such as that which occurs over time to stored nucleic acid samples, or that occurs to samples stored at room temperature. Nonenzymatic nucleic acid degradation includes UV radiation, oxidation, hydrolysis, physical stress such as shearing or tangling, or nucleophilic attach by a free 3' hydroxyl group onto an internal bond of a nucleic acid molecule such that the molecule is cleaved or a lariat formed. Also contemplated herein is nucleic acid damage resulting from enzymatic activity, such as nonspecific endonuclease activity, topoisomerase activity involving single strand nicking or double-strand breakage, restriction endonuclease activity, transposase activity, DNA mismatch repair or base excision, or other enzymatic activity that results in nucleic acid damage such as loss of phase information and/or loss of physical linkage information. Enzymatic degradation is exogenous in some cases, such as that which results from incomplete nucleic acid isolation, or initial isolation in a nonsterile environment such as that which may be encountered during collection 'in the field' such as a remote location or a location which, due for example to an epidemic or other burden on scientific resources, where sterile conditions are not easily or regularly obtained.

Some embodiments herein relate to assembling chromatin in vitro onto partially or totally isolated nucleic acids, such as nucleic acids collected at a field site removed from standard laboratory equipment, such that physical linkage information relating a first segment of a nucleic acid molecule to a second segment of the nucleic acid molecule is not lost in the event that a double strand break occurs between the first nucleic acid molecule and the second nucleic acid molecule. The reassembled chromatin comprises in some cases nucleic acid binding proteins provided from another source. Alternately, in some cases an incompletely isolated nucleic acid sample, such as a nucleic acid sample treated so as to disrupt its native chromatin configuration, to inactivate native nuclease activity, or to disrupt native chromatin and to inactivate native nuclease activity, is contacted to a crosslinking agent so as to stabilize nucleic acids in the sample.

A sample is then subjected to conditions likely to result in enzymatic or nonenzymatic nucleic acid degradation. Nonenzymatic nucleic acid degradation is encountered, for example, during room-temperature storage of samples away from laboratory facilities, or during 'over land' shipment of samples to a facility for further analysis. Conditions are also likely to be encountered during long term storage, such as storage for at least 1, 2, 3, 4, 5, 6, 7, 8, 9, 10, 11, 12 months, or more than 12 months, or 1, 2, 3, 4, 5, or more than 5 year. In some cases a sample is subject to degradation conditions during long term shipping at a temperature of at least 25° C., 30° C., 35° C., 40° C., or greater than 40° C.

Some disclosed methods, compositions, systems and kits relate to storing DNA at room temperature over time, such that physical linkage information is preserved even if nucleic acid double strand breaks are introduced or encountered during storage, for example due to nonenzymatic nucleic acid degradation. Alternately or in combination, some disclosed methods comprise assembling nucleic acids into complexes such that they are not exposed to nucleic acid degrading conditions.

In some aspects, the disclosed methods, compositions, systems and kits are used to identify DNA damage agents over time. Exemplary DNA damaging agents may include but are not limited to hydrolysis, oxidation, damage from enzymes, fragmentation, degradation, decay, mechanical forces, ultraviolet light, and shearing.

Double strand breaks often occur during DNA storage over time. As a result, phasing information of DNA molecule is often difficult to obtain since variants cannot be confidently associated with haplotypes over long-distances. Further, nucleic acid segments separated by long repetitive regions cannot be linked or assembled into a common scaffold. These challenges are only amplified by double strand break introduction resulting from long term storage, room temperature storage, enzymatic or nonenzymatic degradation, or contamination during or after isolation with a composition having a nuclease activity.

Sample degradation significantly affects de novo assembly. The disclosure addresses these problems simultaneously in some embodiments by preventing DNA damage through double strand breaks over time and optionally additionally by reducing the impact on phase determination of double-strand breakage. The preserved high DNA integrity enables methods for generating extremely long-range read pair data (XLRPs) that span genomic distances on the order of hundreds of kilobases, and up to megabases with the appropriate input DNA.

Such data is invaluable for overcoming the substantial barriers presented by loss of physical linkage information by the loss of physical linkage information due to double strand breaks, DNA fragmentation, and large repetitive regions in genomes, including centromeres; enabling cost-effective de novo assembly; and producing re-sequencing data of sufficient integrity and accuracy for genomic analysis and personalized medicine.

The disclosure herein addresses these problems by preventing the loss of phase and/or physical linkage information, or alternately by preserving phase and/or physical linkage information independent of double strand breakage, such that physical linkage information is preserved even upon double strand breakage. Physical linkage information is preserved physically, through binding a first segment and a second segment of a nucleic acid molecule such that they are held together independent of their common phosphodiester backbone. Alternately or in combination, physical linkage information is preserved through the tagging or reciprocal labelling of a first segment and a second segment of a common nucleic acid molecule such that, in the event of introduction of a double strand break between the segments, tag or other label information obtained through sequencing the first segment and adjacent sequence and the second segment and adjacent sequence is sufficient to map the first segment and the second segment to a common phase of a common nucleic acid molecule. Tagging is alternatively achieved through ligating a first segment to a second segment, wherein the second segment is non-adjacent to the first segment, though they are physically linked on the same original DNA molecule.

Of significant importance is the use of reconstituted chromatin in forming associations among very distant, but molecularly-linked, segments of DNA. The disclosure enables distant segments to be brought together and physically bound to one another independent of their common phosphodiester backbone, thereby physically connecting previously distant portions of a common DNA molecule. As a consequence, breakage of double-strand linkages between these disparate nucleic acid segments does not result in loss of phase and/or physical linkage information. Preferably, care is taken such that chromatin reconstitution occurs under conditions that minimize or prevent the inclusion of more than one nucleic acid molecule per individual reconstituted chromatin unit. Subsequent processing allows for the sequence of the associated segments to be ascertained, yielding read pairs whose separation on the genome extends up to the full length of the input DNA molecules.

Physical Linkage Preservation Through Chromatin Reassembly

Disclosed herein are methods, compositions, systems and kits for preserving DNA and maintaining physical linkage information over time despite challenge with DNA damaging agents. DNA damaging agents include hydrolysis, oxidation, enzymatic degradation, fragmentation, mechanical shearing, ultraviolet light, and degradation and decay over time. In some embodiments, DNA is assembled in vitro with DNA-binding agents to generate reconstituted chromatin. DNA binding agents include, for example, DNA-binding proteins, nanoparticles, DNA-binding beads, and beads coated with DNA-binding substances, polymers, synthetic DNA-binding molecules, and other affinity molecules. In some cases SPRI beads are used in 'chromatin' reconstitution. In many cases the bound DNA sample is referred to as reconstituted chromatin, either in the strict sense of reconstitution of native chromatin constituents onto isolated DNA, or as herein, more broadly to refer to reconstitution of a nucleic acid into a heterogeneous complex such that a first segment and a second segment are held together independent of their common phosphodiester backbone.

To further preserve the DNA sample, the reconstituted chromatin, for example, is contacted to a cross-linking agent. Cross-linking occurs through contact with a cross-linking agent such as formaldehyde, though many other cross-linking agents are recited herein or are well known in the field. Often, after cross-linking, the DNA complex is subjected to DNA damage due to suboptimal shipping or storage conditions. When DNA complexes are shipped from remote locations, they are in some cases exposed to high temperatures not conducive to nucleic acid integrity, or to long periods of time at room temperature. During the shipping process, many samples are exposed to X-ray scanning or increased UV-exposure. Even when stored at an optimal temperature, DNA degradation occurs over time, often due to contaminating nucleases, oxidizing metals, oxidation, hydrolysis, or other enzymatic or nonenzymatic DNA damaging agents. In most of these examples, DNA damage leads to double strand breaks in the phosphodiester backbone of the DNA molecules. As DNA damage breaks the phosphodiester bond of a DNA molecule, the DNA molecule is still linked within the cross-linked reconstituted chromatin complex. Therefore, physical linkage information is maintained despite DNA damage. Often, after the DNA complex, such as the reconstituted chromatin, has been cross-linked, tagging information is added to further preserve phase and/or physical linkage information in the event that DNA damage causes degradation to the cross-linked complex. Disclosed herein and incorporated herein are methods for adding such tagging information. In many cases, exposed internal ends are generated by intentionally contacting the cross-linked complex with a DNA-cleaving agent. DNA cleaving agents include, but are not limited to, restriction enzymes, topoisomerases, non-specific endonucleases, DNA repair enzymes, RNA-guided nucleases, and alternate enzymes. The exposed internal ends are then tagged using known methods in the art or by the methods described below. Tagging information allows one to map tagged segments to a common phase of a common molecule of origin. Thus, despite degradation, tagged nucleic acids retain their physical linkage information as to segments adjacent to the tag.

A sample protected through a method, composition, system or kit herein results in a higher quality sequence assembly upon the removal of the reconstituted chromatin and sequencing of the sample. In some cases, the physical molecules of the sample are protected from degradation such as nonenzymatic degradation or enzymatic degradation to which they are subjected. This protection manifests itself in a larger N50 of the physical molecules observed, by sequencing or by other approach such as visualization via size separation on an electrophoresis gel, for example. An N50 of the molecules of a protected sample is increased relative to a control sample by in some cases 2×, 3×, 4×, 5×, 6×, 7×, 8×, 9×, 10×, 20×, 50×, 100×, 200×, 500×, 1000×, 2000×, 5000×, 10,000×, 100,000×, or more than 100,000×. A control sample is in some cases an aliquot of the nucleic acid sample to be sequenced that is taken prior to chromatin reconstitution but otherwise subjected to the same or a comparable treatment regimen. In alternate embodiments, a control sample is a sample previously subjected to the same or a comparable treatment regimen without chromatin reconstitution. In some embodiments, a control sample is a sample of known N50 from experience using a sample collection, storage or transport regimen.

In some cases, phase information and/or physical linkage is preserved despite physical molecules of a reconstituted chromatin complex undergoing degradation such as by double strand breakage. Physical linkage information is preserved such that a first segment and a second segment of a common molecule of the sample are held in proximity by the reconstituted chromatin such that they are assigned to a common phase or common molecule, for example by being similarly tagged or by being ligated to one another subsequent to double strand cleavage due to degradation or in sample preparation. In these cases, an N50 of the contigs and/or scaffolds obtained from sequencing the protected sample is increased relative to the N50 of contigs and/or scaffolds obtained from a control sample. The molecules themselves may be subject to degradation resulting in a decrease in physical linkage, but the physical linkage information is at least in part preserved. The extent of preservation relative to a control sample's sequenced contig and/or scaffold N50 is an increase of in some cases 2×, 3×, 4×, 5×, 6×, 7×, 8×, 9×, 10×, 20×, 50×, 100×, 200×, 500×, 1000×, 2000×, 5000×, 10,000×, 100,000×, or more than 100,000×. A control sample is in some cases an aliquot of the nucleic acid sample to be sequenced that is taken prior to chromatin reconstitution but otherwise subjected to the same or a comparable treatment regimen. In alternate embodiments, a control sample is a sample previously subjected to the same or a comparable treatment regimen without chromatin reconstitution. In some embodiments, a control sample is a sample of known N50 from experience using a sample collection, storage or transport regimen.

The various types of preservation above are not mutually exclusive. That is, reconstitution of chromatin on a nucleic acid sample prior to subjecting the sample to a nucleic acid degradation environment such as nonenzymatic or enzymatic degradation in some cases results in both a preservation of physical molecules such that an N50 measure of the physical molecules is increased and an additional preservation of physical linkage information such that an N50 measure of the assembled contigs and/or scaffolds is improved despite phosphodiester backbone cleavage between segments during enzymatic or nonenzymatic cleavage. That is, preservation of physical molecules and preservation of physical linkage information among molecules subjected to degradation are not mutually exclusive benefits of the methods, systems, compositions or kits disclosed herein.

N50 improvements are determined in some cases by comparison to a control sample or N50 value. In some cases the control is defined strictly, that is by aliquotting a portion of an initial sample, and subjecting it to a treatment comparable to that of the preserved sample but changing a single parameter of the treatment regimen, such as assembly of reconstituted chromatin. Alternately, in some cases the 'control' is more broadly defined, such that a control value or control N50 distribution is that previously experimentally observed to result from a particular treatment regimen. For example, if a treatment regimen is known or expected to yield sample information having an N50 of the resultant contigs and/or scaffolds of a particular low value or range of low values, then a control need not be generated in the individual practice of a method as disclosed herein. Exclusion of a control in sample preparation may in some cases result in more efficient use of reagents, in particular when a large number of samples are collected, transported and sequenced. Alternately, in some cases a control aliquot is regularly taken for each sample.

Following chromatin reconstitution around a nucleic acid sample and subjecting to nucleic acid degradation, the chromatin assembly is reversed and the nucleic acids are optionally subjected to further analysis. Chromatin assembly is reversed by any of a number of approaches known to one of skill in the art, for example treatment of the sample using a protease such as proteinase K. In some cases, samples are processed, for example to tag exposed ends of cleaved nucleic acids, prior to removal of reconstituted chromatin, for example so as to preserve physical linkage information.

Samples are then available to be assayed directly for nucleic acid size, via size selection or size visualization on an electrophoresis gel or other approach. Alternately, samples are subjected to a sequencing regimen so as to determine the sequence and phase of the nucleic acid source material.

Sequencing is achieved by any number of approaches available to one of skill in the art. In some cases samples are shotgun sequenced and then subjected to additional methods such as those disclosed herein or elsewhere to assign physical linkage information to shotgun sequence reads or assembled shotgun contigs and/or scaffolds. Alternately, samples are subjected to a long read sequence approach, alone or in combination with an approach to assign physical linkage information to the resultant long range sequence reads or contigs and/or scaffolds.

Physical Linkage-Preserving Nucleic Acid Labeling

Also disclosed herein are methods, compositions, systems and kits for the labeling of a nucleic acid sample such that nucleic acid segments of a common phase or common molecule are commonly labeled prior to sample degradation, such that sample degradation does not result in loss of label-associated physical linkage information for a labeled segment.

Samples are labeled as described below and elsewhere herein. Briefly, a partially or totally isolated nucleic acid sample is assembled into reconstituted chromatin such that some, the majority, substantially all or all of the nucleic acid molecules are assembled into reconstituted chromatin complexes having a single nucleic acid fragment per complex. Reconstituted chromatin is assembled by addition of polypeptides such as nucleic acid binding proteins, histones, nuclear proteins or other suitable proteins that bind nucleic acids and are amenable to crosslinking. Alternately, reconstituted chromatin is assembled using nanoparticles or other nonpolypeptide moieties such as spermine or spermidine.

Assembled complexes are beneficially constituted such that a first segment and a second segment of a common phase of a nucleic acid molecule are bound such that they are held together independent of their common phosphodiester backbone. Complexes are optionally crosslinked.

Exposed nucleic acid loops of a complex are cleaved such that internal double strand ends are exposed. Cleavage preferably comprises contacting to a sequence specific restriction endonuclease, although other cleavage and tagging approaches are contemplated, such as contacting to a tagmentation enzyme or to a tag-loaded transposase. Exposed ends are labeled, for example using a tag that commonly or uniquely tags the exposed ends of a complex relative to other complexes. That is, preferably, exposed ends of a complex are commonly tagged for a given complex, and distinct complexes are distinctly tagged. In some cases two complexes share a common tag or a single complex receives more than one species of tag. Provided that these events are relatively rare, physical linkage information is still readily derived from tagged complexes in these situations.

Alternately, exposed ends are tagged or labelled by randomly cross-ligating to one another within a complex, such that an exposed end of a first segment is labeled with sequence of a second segment in phase with it in the original molecule but randomly positioned relative to the first fragment.

Labeled nucleic acids are optionally removed from their reconstituted chromatin environment, for example using proteinase K treatment.

Labeled nucleic acids are then subjected to degradation. Sequence independent double-strand breaks are introduced, but physical linkage information that is marked by fragment border tags or by fragment borders being ligated to adjacent fragments is not lost during degradation. Accordingly, upon sequencing of a degraded, labeled sample, fragments are often found to be comparable in size to an unlabeled sample, but contig N50 is substantially larger due to the preservation of physical linkage information associated with fragment-adjacent label sequence. In some cases contig length is 2×, 5×, 10×, 50×, 100×, 500×, 1000× or greater than 1000× improved relative to an unlabeled control sample. Similarly, upon sequencing of a degraded, labeled sample, fragments are often found to be comparable in size to an unlabeled sample, but scaffold N50 is substantially larger due to the preservation of physical linkage information associated with fragment-adjacent label sequence. In some cases scaffold length is 2×, 5×, 10×, 50×, 100×, 500×, 1000× or greater than 1000× improved relative to an unlabeled control sample.

Phase-Relevant Nucleic Acid Size Selection

Also disclosed herein are methods, compositions, systems and kits for the selective recovery of phase-relevant nucleic acid fragments from a sample, such as a degraded sample. These methods, compositions, systems and kits involve the selective binding of phase-relevant nucleic acids prior to sequencing, such that smaller fragments, less likely to retain physical linkage information, are excluded from downstream analysis.

In such cases, a degraded sample is received and subjected to chromatin reconstitution using a non-nucleic acid moiety that selectively binds nucleic acid fragments above a size threshold. For example, chromatin is in some cases reconstituted using nucleosomes or histone aggregates that do not bind to nucleic acid fragments having a length of less than or nucleosome perimeter, or approximately 140 bases or 200 bases. Alternate reconstituted chromatin constituents are contemplated having lower or greater binding length thresholds. Complexes are optionally crosslinked as disclosed herein. Complexes are washed such that unbound nucleic acid fragments are not retained. Wash conditions are alternate selected such that complexes below a desired molecular weight are not retained. As reconstituted chromatin often has a molecular weight that is proportional to the length of the bound nucleic acid, selective exclusion of lower-weight complexes removes shorter fragments from downstream analysis.

Retained complexes are sequenced using any number of approaches known to one of skill in the art. In some cases complexes are shotgun sequenced, long-read sequenced or otherwise subjected to sequence determination. Complexes are in some cases subjected to controlled endonuclease treatment to generate exposed internal ends and then labeled and sequenced as disclosed herein.

That is, assembled complexes are beneficially constituted such that a first segment and a second segment of a common phase of a nucleic acid molecule are bound such that they are held together independent of their common phosphodiester backbone. Complexes are optionally crosslinked.

Exposed nucleic acid loops of a complex are cleaved such that internal double strand ends are exposed. Cleavage preferably comprises contacting to a sequence specific restriction endonuclease, although other cleavage and tagging approaches are contemplated, such as contacting to a tagmentation enzyme or to a tag-loaded transposase. Exposed ends are labeled, for example using a tag that commonly or uniquely tags the exposed ends of a complex relative to other complexes. That is, preferably, exposed ends of a complex are commonly tagged for a given complex, and distinct complexes are distinctly tagged. In some cases two complexes share a common tag or a single complex receives more than one species of tag. Provided that these events are relatively rare, physical linkage information is still readily derived from tagged complexes in these situations.

Alternately, exposed ends are labelled or tagged by randomly cross-ligating to one another within a complex, such that an exposed end of a first segment is labeled with sequence of a second segment in phase with it in the original molecule but randomly positioned relative to the first fragment.

Labeled nucleic acid fragments are then sequenced and contigs and/or scaffolds are assembled. It is observed that contigs and/or scaffolds generated through the size-selection approaches disclosed herein, alone or in combination with the phase-preserving approaches disclosed herein or known in the art such as those elsewhere incorporated by reference herein, result in sequences that assemble into contigs and/or scaffolds having N50 values comparable to those of control samples undergoing no size selection. However, the comparable N50 contig and/or scaffold sizes are obtained using substantially less sequence time, reagents and computational capacity. For example, a contig assembly is generated having an N50 value comparable to a control sample while comprising no more than 50%, 40%, 30%, 25%, 20%, 15%, 10%, 5%, 4%, 3%, 2%, 1%, 0.5%, 0.1%, 0.05%, 0.01% or less than 0.01% of the raw sequence information of the unenriched sample. Similarly, in some cases a scaffold assembly is generated having an N50 value comparable to a control sample while comprising no more than 50%, 40%, 30%, 25%, 20%, 15%, 10%, 5%, 4%, 3%, 2%, 1%, 0.5%, 0.1%, 0.05%, 0.01% or less than 0.01% of the raw sequence information of the unenriched sample.

Physical Linkage Preservation and Sequencing Approaches

Physical linkage information is obtained through any number of approaches known to one of skill in the art. For example, reconstituted chromatin is optionally subjected to controlled cleavage separate from the degradation to which it is subjected, so that regular exposed ends amenable to downstream analysis are generated. Exposed ends are optionally attached to tagged oligonucleotides which identify the tagged exposed ends as originating from the same DNA molecule. This attachment often occurs through ligation or polymerase extension. In some cases the tagged oligonucleotides are barcoded to identify molecules originating from a common DNA molecule and/or biotinylated for downstream isolation.

Exposed ends optionally are partially filled, for example with dNTPs or labeled dNTPs, in to prevent religation. Oligonucleotides, such as punctuation oligonucleotides, with ends compatible with the partially filled-in sticky ends are added to the chromatin sample along with a DNA ligase. In some instances, the punctuation oligonucleotides are dephosphorylated in order to avoid contatemerization of the oligonucleotides. Alternatively, oligonucleotide tags are added through transposase activity. In these cases, transposase bound to two punctuation oligonucleotides is added to the cross-linked DNA complex. The transposase cleaves exposed DNA segments and inserts the two punctuation oligonucleotides into the DNA. In some cases, the transposase-bound oligonucleotides are linked. In other cases, the transposase-bound oligonucleotides are unlinked. When the oligonucleotides are unlinked, the insertion results in two free DNA ends, each terminated by one of the two punctuation oligonucleotides. Many times, DNA ligase is added to the sample to ligate blunt DNA ends together, resulting in a rearrangement of DNA segments, though physical linkage information is maintained since the DNA molecule is bound to the chromatin proteins throughout this process.

In yet other examples, exposed ends are filled-in with labeled dNPTs, such as an alpha-thio-dGTP and a biotinylated dCTP to generate blunt ends. In many of these examples, the cross-linked DNA complex is biotinylated prior to exposure of the internal DNA ends. After filling in the exposed ends, the blunt ends are often ligated to generate paired-ends. Though, other methods of attaching the paired ends are envisioned such as polymerase extension transposase activity.

Tagging information is be added to the cross-linked DNA complex as disclosed herein or by other tagging methods well known in the art. Tagging information is ideally added prior to exposure to DNA damage, however in many circumstances it is necessary to add tagging information after DNA damage has occurred. In the latter cases, it is often preferred to remove non-complexed DNA prior to adding tagging information. Non-complexed DNA is removed by washing, differential centrifugation, gel-electrophoresis, chromatography, other traditional methods, or any combination thereof. In some cases, non-complex DNA is removed from samples prior to DNA damage occurring.

Disclosed herein are methods for isolating and enriching phase-informative or physical linkage-informative fragments of DNA. Long DNA molecules are needed to determine physical linkage information. Following DNA extraction, DNA molecules of different sizes are included in the DNA sample. Furthermore, DNA damage as discussed herein causes further fragmentation of the DNA sample and the DNA damage will accumulate over time. Therefore, DNA samples stored in non-optimal conditions for long period of time will be heaving degraded. In many of the methods disclosed herein, to isolate or enrich for phase-informative or physical linkage-informative DNA fragments, the DNA sample is assembled in vitro into reconstituted chromatin as disclosed herein. Only the DNA molecules long enough to wrap about the DNA binding agent are incorporated into the chromatin complex. In many instances, after reconstitution, the sample is washed to remove non-complexed DNA molecules, leaving only the reconstituted chromatin complexes. The complexed DNA molecules which contain important phasing information are protected against further degradation by DNA damaging agents. Alternatively, the enriched complexed DNA molecules can be directly sequenced to generate physical linkage information. In some examples, prior to sequencing, the enriched DNA complex is processed in order to add tagging information. For example, the DNA sample has tagging information added through any of the methods disclosed herein. Additionally or alternatively, tagging information is added such that the sample is compatible for sequencing with PacBio, Illumina, OxfordNanopore, or other well-known sequencing technologies.

Disclosed herein are methods for identifying DNA preserving agents and conditions. In many examples, isolated DNA is assembled in vitro into reconstituted chromatin and cross-linked as disclosed herein. The sample is then treated with a DNA damage agent and then processed to add tagging information as disclosed herein. After sequencing, the relative quality of the sample is evaluated to determine how much damage was caused by the DNA damage agent. In some case, the experiment is repeated while changing one of the parameters of the reconstitution or cross-linking steps. Sequencing results are compared to determine if the alterations in the second experiment increased or decreased the preservation of the DNA sample. In cases where the preservation is increased, a new DNA preservation agent is identified. In any of these cases, a portion of the DNA sample that is not exposed to DNA damage can be processed and sequenced in parallel as a control.

Disclosed herein are kits for preserving and storing DNA samples such that physical linkage information is maintained following DNA damage. In some examples, the kit includes reagents necessary for DNA extraction, DNA binding, and cross-linking. DNA extraction reagents in some cases include reagents for extraction of high molecular weight DNA. In many cases, the DNA binding reagents include reagents necessary to bind DNA to a solid surface as disclosed herein, for example, it includes the reagents necessary to generate reconstituted chromatin in vitro. In many cases, the cross-linking agent is formaldehyde or another well-known cross-linking agent. In preferred examples, all of the reagents of the disclosed kit are stable without refrigeration for at least 1 week, 1 month, 6 months, 1 year, or for longer than 1 year. In some examples, the kits further include other reagents to protect against DNA damage, such as metal chelators or anti-oxidants as non-limiting examples, though other additional protective agents are envisioned and would be easily recognized by one of skill in the art.

The methods, compositions and kits disclosed herein provide effective and inexpensive means for storing DNA and preserving DNA integrity over time. DNA molecules stored and shipped using methods, compositions, and kits disclosed herein are stable at room temperature. The stored DNA molecules are transported at room temperature, and are resistant to DNA damage through chemical-, mechanical-, and enzymatic-insults. As a result, phasing information and haplotype information are preserved, which is of advantage for de novo genome assembly, or assembly of contigs of a genome, or assembly of scaffolds of a genome. In general, the methods disclosed herein reconstitute chromatin in vitro from naked DNA in some cases using synthetic histones, and then reversibly crosslink the chromatin to provide exceptionally durable storage of high molecular weight DNA. The resulting artificial chromatin is shipped and stored with minimal breakage. Upon receipt of the artificial chromatin, the cross-linking may be reversed and histones removed as needed to recover the naked DNA. Furthermore, the methods uniquely preserve contiguity in spite of DNA fragmentation because chromatin assembly and crosslinking stabilizes a DNA molecule such that any fragmentation of DNA keeps the fragmented ends in close proximity to one another. Crosslinked chromatin can be later processed to retrieve contiguity information that can then be used to reconstruct the original, HMW fragments, using a recently developed pair-end sequencing library methodology (Putnam, et al., 2015 "Chromosome-scale shotgun assembly using an in vitro method for long-range linkage." Available online at the website //arxiv.org/abs/1502.05331, the contents of which are hereby incorporated by reference in its entirety.)

Disclosed herein are methods, compositions and kits of crosslinking in vitro assembled chromatin, which have the potential to produce a cost-effective DNA preservation product that mitigates DNA fragmentation and other damage while preserving contiguity information in spite of fragmentation. The method may comprise 1) extracting high molecular weight (HMW) DNA from a sample, 2) reconstituting the extracted DNA as in vitro chromatin, and 3) fixing reconstituted chromatin with a crosslinking agent such as formaldehyde (FIG. 1A-1G).

Research interests affected by the loss of DNA contiguity include the ability to assemble and compare genomes, determining phase variation, characterizing large structural variants, resolving paralogs and regions of the genome rich in repeated DNA, and deconvoluting metagenomic mixtures. Because there are many domains that are impacted by DNA integrity, simple, affordable technologies for the long-term preservation of the information encoded by DNA have become a critical necessity for the field.

Methods disclosed herein produce fragments of genomic DNA up to megabase scale. Long DNA fragments may be generated to confirm the ability of the present methods to generate read pairs spanning the longest fragments offered by those extractions. In some cases, DNA fragments beyond 150 kb in length may be extracted and used to generate XLRP libraries.

Methods disclosed herein utilize data analysis that allows for rapid and inexpensive de novo assembly of genomes from one or more subjects. Some methods disclosed herein produce high quality assemblies with far less data than previously required. The methods disclosed herein may be used in a variety of applications, including haplotype phasing and metagenomics analysis. The disclosure provides methods that generate chromosome-level phasing using a long-distance read pair approach. For example, some methods disclosed herein phase 90% or more of the heterozygous single nucleotide polymorphisms (SNPs) in a sample for that individual to an accuracy of at least 99% or greater. This accuracy is on par with phasing produced by substantially more costly and laborious methods.

In various examples, the disclosure provides methods to determine haplotype phasing comprising a step of identifying one or more sites of heterozygosity in the plurality of read pairs, wherein phasing data for allelic variants may be determined by identifying read pairs that comprise a pair of heterozygous sites. In various cases, the disclosure provides methods for high-throughput bacterial genome assembly, comprising a step of generating a plurality of read pairs by probing the physical layout of a plurality of microbial chromosomes using a modified Hi-C based method, comprising the modified steps of: collecting microbes from an environment; adding a fixative agent, such as formaldehyde, so as to form cross-links within each microbial cell, and wherein read pairs mapping to different contigs indicate which contigs are from the same species. In some examples, the disclosed provides methods for generating labeled polynucleotides from a plurality of DNA molecules. Methods, compositions, and kits for generating read pairs, labeling polynucleotides, assembling genomes, and determining phasing information disclosed herein, such as, but not limited to those found in Patent Publication Number WO2014/121091 A1, and PCT Patent Application Number PCT/US2015/043327, which published as International Publication No. WO2016/019360, both of which are hereby incorporated by reference in their entirety.

In particular embodiments, the methods of the disclosure are easily applied to any type of fragmented double stranded DNA including but not limited to, for example, free DNA isolated from plasma, serum, and/or urine; apoptotic DNA from cells and/or tissues; DNA fragmented enzymatically in vitro (for example, by DNase I and/or restriction endonuclease); and/or DNA fragmented by mechanical forces (hydro-shear, sonication, nebulization, etc.).

In various examples, nucleic acid obtained from biological samples are fragmented to produce suitable fragments for analysis. Template nucleic acids are fragmented or sheared to desired length in some cases, using a variety of mechanical, chemical and/or enzymatic methods. For example, DNA is randomly sheared via sonication, e.g. Covaris method, brief exposure to a DNase, or using a mixture of one or more restriction enzymes, or a transposase or nicking enzyme. In further examples, RNA is fragmented by brief exposure to an RNase, heat plus magnesium, or by shearing. The RNA in some cases is converted to cDNA. If fragmentation is employed, the RNA is often converted to cDNA before or after fragmentation. In some examples, nucleic acid from a biological sample is fragmented by sonication. In other cases, nucleic acid is fragmented by a hydroshear instrument. Generally, individual nucleic acid template molecules are from about 2 kb to about 1 Mb. In various instances, nucleic acids may be about 6 kb to about 10 kb fragments. Nucleic acid molecules may be single-stranded, double-stranded, or double-stranded with single-stranded regions (for example, stem- and loop-structures).

Disclosed herein are methods wherein cross-linked DNA complexes are subjected to a size selection step. Size selection of the nucleic acids is performed, for example, to cross-linked DNA complexes below or above a certain size. Size selection is affected by the frequency of cross-links and/or by the fragmentation method, for example, by choosing a frequent or rare cutter restriction enzyme. At times, a composition is prepared comprising cross-linking a DNA complex in the range of about 1 kb to 5 Mb, about 5 kb to 5 Mb, about 5 kb to 2 Mb, about 10 kb to 2 Mb, about 10 kb to 1 Mb, about 20 kb to 1 Mb about 20 kb to 500 kb, about 50 kb to 500 kb, about 50 kb to 200 kb, about 60 kb to 200 kb, about 60 kb to 150 kb, about 80 kb to 150 kb, about 80 kb to 120 kb, or about 100 kb to 120 kb, or any range bounded by any of these values (e.g. about 150 kb to 1 Mb).

In some methods disclosed herein, sample polynucleotides are fragmented into a population of fragmented DNA molecules of one or more specific size range (s). In various examples, fragments are generated from at least about 1, about 2, about 5, about 10, about 20, about 50, about 100, about 200, about 500, about 1000, about 2000, about 5000, about 10,000, about 20,000, about 50,000, about 100,000, about 200,000, about 500,000, about 1,000,000, about 2,000,000, about 5,000,000, about 10,000,000, or more genome-equivalents of starting DNA. Fragmentation is accomplished by methods known in the art, including chemical, enzymatic, and mechanical fragmentation. In some cases, the fragments have an average length from about 10 to about 10,000, about 20,000, about 30,000, about 40,000, about 50,000, about 60,000, about 70,000, about 80,000, about 90,000, about 100,000, about 150,000, about 200,000, about 300,000, about 400,000, about 500,000, about 600,000, about 700,000, about 800,000, about 900,000, about 1,000,000, about 2,000,000, about 5,000,000, about 10,000,000, or more nucleotides. Sometimes the fragments have an average length from about 1 kb to about 10 Mb. Additionally or alternatively the fragments have an average length from about 1 kb to 5 Mb, about 5 kb to 5 Mb, about 5 kb to 2 Mb, about 10 kb to 2 Mb, about 10 kb to 1 Mb, about 20 kb to 1 Mb about 20 kb to 500 kb, about 50 kb to 500 kb, about 50 kb to 200 kb, about 60 kb to 200 kb, about 60 kb to 150 kb, about 80 kb to 150 kb, about 80 kb to 120 kb, or about 100 kb to 120 kb, or any range bounded by any of these values (e.g. about 60 to 120 kb). In some cases, the fragments have an average length less than about 10 Mb, less than about 5 Mb, less than about 1 Mb, less than about 500 kb, less than about 200 kb, less than about 100 kb, or less than about 50 kb. The fragments may have an average length more than about 5 kb, more than about 10 kb, more than about 50 kb, more than about 100 kb, more than about 200 kb, more than about 500 kb, more than about 1 Mb, more than about 5 Mb, or more than about 10 Mb. In many cases, fragmentation is accomplished mechanically comprising subjection sample DNA molecules to acoustic sonication. Alternatively the fragmentation comprises treating the sample DNA molecules with one or more enzymes under conditions suitable for the one or more enzymes to generate double-stranded nucleic acid breaks. Examples of enzymes useful in the generation of DNA fragments include sequence specific and non-sequence specific nucleases. Non-limiting examples of nucleases include DNase I, Fragmentase, restriction endonucleases, variants thereof, and combinations thereof. For example, digestion with DNase I induces random double-stranded breaks in DNA in the absence of Mg++ and in the presence of Mn++. Additionally or alternatively, fragmentation comprises treating the sample DNA molecules with one or more restriction endonucleases. In some cases, fragmentation produces fragments having 5' overhangs, 3' overhangs, blunt ends, or a combination thereof. In other cases, such as when fragmentation comprises the use of one or more restriction endonucleases, cleavage of sample DNA molecules leaves overhangs having a predictable sequence. In some cases, the method includes the step of size selecting the fragments via standard methods such as column purification or isolation from an agarose gel.

Often, the 5' and/or 3' end nucleotide sequences of fragmented DNA are not modified prior to ligation. For example, fragmentation by a restriction endonuclease is used to leave a predictable overhang, followed by ligation with a nucleic acid end comprising an overhang complementary to the predictable overhang on a DNA fragment. In other examples, cleavage by an enzyme that leaves a predictable blunt end is followed by ligation of blunt-ended DNA fragments to nucleic acids, such as adapters, oligonucleotides, or polynucleotides, comprising a blunt end. In some cases, the fragmented DNA molecules are blunt-end polished (or "end repaired") to produce DNA fragments having blunt ends, prior to being joined to adapters. The blunt-end polishing step is accomplished, for example, by incubation with a suitable enzyme, such as a DNA polymerase that has both 3' to 5' exonuclease activity and 5' to 3' polymerase activity, for example T4 polymerase. Often, end repair is followed by an addition of 1, 2, 3, 4, 5, 6, 7, 8, 9, 10, 11, 12, 13, 14, 15, 16, 17, 18, 19, 20 or more nucleotides, such as one or more adenine, one or more thymine, one or more guanine, or one or more cytosine, to produce an overhang. For example, the end pair is followed by an addition of 1, 2, 3, 4, 5, or 6 nucleotides. In some cases, DNA fragments having an overhang is joined to one or more nucleic acids, such as oligonucleotides, adapter oligonucleotides, punctuation oligonucleotides, or polynucleotides, having a complementary overhang, such as in a ligation reaction. For example, a single adenine is added to the 3' ends of end repaired DNA fragments using a template independent polymerase, followed by ligation to one or more adapters each having a thymine at a 3' end. In some embodiments, nucleic acids, such as oligonucleotides or polynucleotides are joined to blunt end double-stranded DNA molecules which have been modified by extension of the 3' end with one or more nucleotides followed by 5' phosphorylation. In some cases, extension of the 3' end is performed with a polymerase such as, Klenow polymerase or any of the suitable polymerases provided herein, or by use of a terminal deoxynucleotide transferase, in the presence of one or more dNTPs in a suitable buffer that can contain magnesium. In some examples, target polynucleotides having blunt ends are joined to one or more adapters comprising a blunt end. Phosphorylation of 5' ends of DNA fragment molecules is performed for example with T4 polynucleotide kinase in a suitable buffer containing ATP and magnesium. The fragmented DNA molecules are optionally treated to dephosphorylate 5' ends or 3' ends, for example, by using enzymes known in the art, such as phosphatases.

The terms "connecting", "joining" and "ligation" as used herein, with respect to two polynucleotides, such as an adapter oligonucleotide and a target polynucleotide, refers to the covalent attachment of two separate DNA segments to produce a single larger polynucleotide with a contiguous backbone. Methods for joining two DNA segments are known in the art, and include without limitation, enzymatic and non-enzymatic (e.g. chemical) methods. Examples of ligation reactions that are non-enzymatic include the non-enzymatic ligation techniques described in U.S. Pat. No. 5,780,613 issued Jul. 14, 1998, and U.S. Pat. No. 5,476,930 issued Dec. 19, 1995, which are herein incorporated by reference in their entirety. In some examples, an adapter oligonucleotide is joined to a target polynucleotide by a ligase, for example a DNA ligase or RNA ligase. Multiple ligases, each having characterized reaction conditions, are known in the art, and include, without limitation NAD⁺-dependent ligases including tRNA ligase, Taq DNA ligase, *Thermus filiformis* DNA ligase, *Escherichia coli* DNA ligase, Tth DNA ligase, *Thermus scotoductus* DNA ligase (I and II), thermostable ligase, Ampligase thermostable DNA ligase, VanC-type ligase, 9° N DNA Ligase, Tsp DNA ligase, and novel ligases discovered by bioprospecting; ATP-dependent ligases including T4 RNA ligase, T4 DNA ligase, T3 DNA ligase, T7 DNA ligase, Pfu DNA ligase, DNA ligase 1, DNA ligase III, DNA ligase IV, and novel ligases discovered by bioprospecting; and wild-type, mutant isoforms, and genetically engineered variants thereof.

Alternatively "ligation" is achieved by synthesizing a new molecule that comprises the segments to be attached to one another attached into a single molecule.

In some methods disclosed herein, ligation is between DNA segments having hybridizable sequences, such as complementary overhangs. Alternatively, ligation is between two blunt ends. Generally, a 5' phosphate is utilized in a ligation reaction. In these cases, the 5' phosphate is provided by the target polynucleotide, the adapter oligonucleotide, or both. 5' phosphates can be added to or removed from DNA segments to be joined, as needed. Methods for the addition or removal of 5' phosphates are known in the art, and include without limitation enzymatic and chemical processes. Enzymes useful in the addition and/or removal of 5' phosphates include kinases, phosphatases, and polymerases. In some examples, both of the two ends joined in a ligation reaction (e.g. an adapter end and a target polynucleotide end) provide a 5' phosphate, such that two covalent linkages are made in joining the two ends. In other examples, only one of the two ends joined in a ligation reaction (e.g. only one of an adapter end and a target polynucleotide end) provides a 5' phosphate, such that only one covalent linkage is made in joining the two ends.

An adaptor oligonucleotide is joined to only one strand at one or both ends of a target polynucleotide. Alternatively, both strands at one or both ends of a target polynucleotide are joined to an adapter oligonucleotide. In some cases, 3' phosphates are removed prior to ligation. Additionally or alternatively, an adapter oligonucleotide is added to both ends of a target polynucleotide, wherein one or both strands at each end are joined to one or more adapter oligonucleotides. When both strands at both ends are joined to an adapter oligonucleotide, joining is followed in some examples by a cleavage reaction that leaves a 5' overhang that can serve as a template for the extension of the corresponding 3' end, which 3' end may or may not include one or more nucleotides derived from the adapter oligonucleotide. Sometimes, a target polynucleotide is joined to a first adapter oligonucleotide on one end and a second adapter oligonucleotide on the other end. Alternatively, two ends of a target polynucleotide are joined to the opposite ends of a single adapter oligonucleotide. In some cases, the target polynucleotide and the adapter oligonucleotide to which it is joined comprise blunt ends. In many examples, separate ligation reactions are carried out for each sample, using a different first adapter oligonucleotide comprising at least one barcode sequence for each sample, such that no barcode sequence is joined to the target polynucleotides of more than one sample. A DNA segment or a target polynucleotide that has an adapter oligonucleotide joined to it is considered "tagged" by the joined adapter.

The ligation reaction is performed at a DNA segment or target polynucleotide concentration of about 0.1 ng/μl, about 0.2 ng/μl, about 0.3 ng/μl, about 0.4 ng/μl, about 0.5 ng/μl, about 0.6 ng/μl, about 0.7 ng/μl, about 0.8 ng/μl, about 0.9 ng/μl, about 1.0 ng/μl, about 1.2 ng/μl, about 1.4 ng/μl, about 1.6 ng/μl, about 1.8 ng/μl, about 2.0 ng/μl, about 2.5 ng/μl, about 3.0 ng/μl, about 3.5 ng/μl, about 4.0 ng/μl, about 4.5 ng/μl, about 5.0 ng/μl, about 6.0 ng/μl, about 7.0 ng/μl, about 8.0 ng/μl, about 9.0 ng/μl, about 10 ng/μl, about 15 ng/μl, about 20 ng/μl, about 30 ng/μl, about 40 ng/μl, about 50 ng/μl, about 60 ng/μl, about 70 ng/μl, about 80 ng/μl, about 90 ng/μl, about 100 ng/μl, about 150 ng/μl, about 200 ng/μl, about 300 ng/μl, about 400 ng/μl, about 500 ng/μl, about 600 ng/μl, about 800 ng/μl, about 1000 ng/μl, or a higher concentration. For example, the ligation is performed at a DNA segment or target polynucleotide concentration of about 100 ng/μl, about 150 ng/μl, about 200 ng/μl, about 300 ng/μl, about 400 ng/μl, or about 500 ng/μl.

In some cases, the ligation reaction is performed at a DNA segment or target polynucleotide concentration of about 0.1 to 1000 ng/μl, about 1 to 1000 ng/μl, about 1 to 800 ng/μl, about 10 to 800 ng/μl, about 10 to 600 ng/μl, about 100 to 600 ng/μl, or about 100 to 500 ng/μl.

In many cases, the ligation reaction is performed for more than about 5 minutes, about 10 minutes, about 20 minutes, about 30 minutes, about 40 minutes, about 50 minutes, about 60 minutes, about 90 minutes, about 2 hours, about 3 hours, about 4 hours, about 5 hours, about 6 hours, about 8 hours, about 10 hours, about 12 hours, about 18 hours, about 24 hours, about 36 hours, about 48 hours, or about 96 hours. In other cases, the ligation reaction can be performed for less than about 5 minutes, about 10 minutes, about 20 minutes, about 30 minutes, about 40 minutes, about 50 minutes, about 60 minutes, about 90 minutes, about 2 hours, about 3 hours, about 4 hours, about 5 hours, about 6 hours, about 8 hours, about 10 hours, about 12 hours, about 18 hours, about 24 hours, about 36 hours, about 48 hours, about 96 hours, or a greater length of time. For example, the ligation reaction is performed for about 30 minutes to about 90 minutes. In some instances, joining of an adapter to a target polynucleotide produces a joined product polynucleotide having a 3' overhang comprising a nucleotide sequence derived from the adapter.

In some examples, after joining at least one adapter oligonucleotide to a target polynucleotide, the 3' end of one or more target polynucleotides is extended using the one or more joined adapter oligonucleotides as template. For example, an adapter comprising two hybridized oligonucleotides that is joined to only the 5' end of a target polynucleotide allows for the extension of the unjoined 3' end of the target using the joined strand of the adapter as template, concurrently with or following displacement of the unjoined strand. Both strands of an adapter comprising two hybridized oligonucleotides are joined to a target polynucleotide such that the joined product has a 5' overhang, and the complementary 3' end can be extended using the 5' overhang as template. As a further example, a hairpin adapter oligonucleotide is joined to the 5' end of a target polynucleotide. In some examples, the 3' end of the target polynucleotide that is extended comprises one or more nucleotides from an adapter oligonucleotide. For target polynucleotides to which adapters are joined on both ends, extension is, in some examples, carried out for both 3' ends of a double-stranded target polynucleotide having 5' overhangs. This 3' end extension, or "fill-in" reaction, generates a complementary sequence, or "complement," to the adapter oligonucleotide template that is hybridized to the template, thus filling in the 5' overhang to produce a double-stranded sequence region. Where both ends of a double-stranded target polynucleotide have 5' overhangs that are filled in by extension of the complementary strands' 3' ends, the product is completely double-stranded. In many examples, extension is carried out by any suitable polymerase known in the art, such as a DNA polymerase, many of which are commercially available. DNA polymerases can comprise DNA-dependent DNA polymerase activity, RNA-dependent DNA polymerase activity, or DNA-dependent and RNA-dependent DNA polymerase activity. DNA polymerases are thermostable or non-thermostable. Examples of DNA polymerases include, but are not limited to, Taq polymerase, Tth polymerase, Tli polymerase, Pfu polymerase, Pfutubo polymerase, Pyrobest polymerase, Pwo polymerase, KOD polymerase, Bst polymerase, Sac polymerase, Sso polymerase, Poc polymerase, Pab polymerase, Mth polymerase, Pho polymerase, ES4 polymerase, VENT polymerase, DEEPVENT polymerase, EX-Taq polymerase, LA-Taq polymerase, Expand polymerases, Platinum Taq polymerases, Hi-Fi polymerase, Tbr polymerase, Tfl polymerase, Tru polymerase, Tac polymerase, Tne polymerase, Tma polymerase, Tih polymerase, Tfi polymerase, Klenow fragment, and variants, modified products and derivatives thereof 3' end extension can be performed before or after pooling of target polynucleotides from independent samples.

The present disclosure provides methods for generating labeled polynucleotides from a first DNA molecule comprising a first sequence segment and a second sequence segment. In some cases, the present disclosure provides methods for preserving these labeled polynucleotides. For example, the method comprises: a. crosslinking the first sequence segment and the second sequence segment outside of a cell; b. adding the first sequence segment and the second sequence segment to a first resolved locus comprising a plurality of binding probes; and c. generating a first labeled polynucleotide comprising a first label and a first complement sequence, and a second labeled polynucleotide comprising a second label and a second complement sequence.

The present disclosure provides methods for labeling DNA segments. In some cases, the method comprises: a. crosslinking a first DNA molecule to yield a DNA complex; b. severing the DNA complex to form a plurality of sequence segments comprising a first sequence segment and a second sequence segment, wherein the first sequence segment comprises a first segment end and the second sequence segment comprises a second segment end; and c. attaching a first label to the first segment end and a second label to the second segment end.

In some examples, the first DNA molecule is severed by any known method in the art, including but not limited to the chemical, enzymatic, and mechanical fragmentation methods disclosed in the present application. For example, the first DNA molecule is severed using a restriction enzyme. Alternatively, the first DNA molecule is severed by ultraviolet irradiation. The first segment end and the second segment end often comprise blunt ends. Other times, the first segment end and the second segment end comprise overhang sequences. In some cases, the overhang sequences are filled in to generate blunt ends (e.g. using a DNA polymerase). In some of these cases, the overhangs are filled in by modified nucleotides, such as sulfated or biotinylated nucleotides. In other cases, the overhang sequences are cut with an exonuclease to generate blunt ends.

In some cases, the first DNA molecule is contacted to a cross-linking agent within a cell. Alternatively, the first DNA molecule is part of chromatin obtained from whole cell or nuclear extracts. In preferred examples, the first DNA molecule contacted to a cross-linking agent outside of a cell. For example, the first DNA molecule is isolated and contacted to a cross-linking agent in vitro. The cross-linking is performed using photo-irradiation methods (e.g. UV irradiation) or chemical agents (e.g. formaldehyde) as non-limiting examples.

In some examples, the first DNA molecule is contacted to a plurality of association molecules prior to cross-linking. In many cases, the association molecules comprise amino acids. In some of these cases, the association molecules comprise peptides, proteins or, amino acids. In certain examples, the association molecules comprise peptides or proteins such as DNA binding proteins. Exemplary DNA binding proteins include native chromatin constituents such as histone, for example Histones 2A, 2B, 3A, 3B, 4A, or 4B. In some examples, the binding proteins comprise transcription factors. Non-protein organic molecules are also compatible with the disclosure herein, such as protamine, spermine, spermidine or other positively charged molecules. In further cases, the association molecules are from a different source than the first DNA molecule. In some cases, the first DNA molecule is from a first human subject, whereas the association molecules are from a second human subject. In other examples, the first DNA molecule is from a mammal (e.g. human), whereas the association molecules are from another eukaryotic organism. In further examples, the first DNA molecule is from a eubacterium or an archaean organism, whereas the association molecules are from a eukaryotic organism.

Additionally or alternatively, the association molecules comprise nanoparticles, such as nanoparticles having a positively charged surface. A number of nanoparticle compositions are compatible with the disclosure herein. In some cases, the nanoparticle is a platinum-based nanoparticle. In certain cases, the platinum-based nanoparticle is selected from the group consisting of cisplatin, oxaliplatin, and transplatin. In other examples, the nanoparticle is a DNA intercalator, or any derivatives thereof. In further examples, the nanoparticle is a bisintercalator, or any derivatives thereof. In further cases, the nanoparticle is a bisintercalator, or any derivatives thereof. In some cases, the DNA intercalator is a bis-intercalator. In further cases, the bis-intercalator is bisacridine. In some embodiments the nanoparticles comprise silica, such as silica coated with a positive coating so as to bind negatively charged nucleic acids. In further examples, the nanoparticles are magnetic or paramagnetic, which may facilitate the isolation of the cross-linked sequence segments. In some cases, the nanoparticles are coated with amine groups, and/or amine-containing molecules. In certain cases, the DNA and the nanoparticles aggregate and condense. In further cases, the nanoparticle-bound DNA is induced to aggregate in a fashion that mimics the ordered arrays of biological nucleosomes (e.g. chromatin). In some cases, the association molecules are from a different source than the first DNA molecule. In some cases, the first DNA molecule is obtained from a first human subject, whereas the association molecules are from a second human subject. In other examples, the first DNA molecule is from a mammal (e.g. human), whereas the association molecules are from another eukaryotic organism. In further examples, the first DNA molecule is obtained from a plant cell, another non-mammalian eukaryote, a eubacterium or an archaeal cell, whereas the association molecules are from a eukaryotic organism.

In some examples, nanoparticles are used to generate read pairs from a single DNA molecule for assembling a contig, scaffold or a genome as described in PCT Patent Application Number PCT/US2015/043327, which published as International Publication No. WO2016/019360, and which is hereby incorporated by reference in its entirety. In general, single DNA molecule is cross-contacted to a plurality of nanoparticles in vitro or in vivo, and the complex is then cross-linked. A plurality of contigs and/or scaffolds of the single DNA molecule are assembled using the read pairs, wherein at least 1% of the read pairs spans a distance of at least 10 kb, at least 20 kb, at least 30 kb, at least 50 kb, or more on the single DNA molecule, and wherein the haplotype phasing is performed at greater than 70% accuracy. In certain cases, at least 10% of the read pairs span a distance of at least 50 kb on the single DNA molecule. In further cases, at least 1% of the read pairs span a distance of at least 100 kb on the single DNA molecule. In various cases, the haplotype phasing is performed at greater than 90% accuracy. In some cases, the crosslinking is reversible. In certain cases, the crosslinking is reversed using heat. In other cases, the crosslinking is reversed using a chemical agent such as thiourea.

A number of factors are varied to influence the extent and form of condensation including the concentration of nanoparticles in solution, the ratio of nanoparticles to DNA, and the size of nanoparticles used. In some cases, the nanoparticles are added to the DNA at a concentration greater than about 1 ng/ml, 2 ng/ml, 3 ng/ml, 4 ng/ml, 5 ng/ml, 6 ng/ml, 7 ng/ml, 8 ng/ml, 9 ng/ml, 10 ng/ml, 15 ng/ml, 20 ng/ml, 25 ng/ml, 30 ng/ml, 40 ng/ml, 50 ng/ml, 60 ng/ml, 70 ng/ml, 80 ng/ml, 90 ng/ml, 100 ng/ml, 120 ng/ml, 140 ng/ml, 160 ng/ml, 180 ng/ml, 200 ng/ml, 250 ng/ml, 300 ng/ml, 400 ng/ml, 500 ng/ml, 600 ng/ml, 700 ng/ml, 800 ng/ml, 900 ng/ml, 1 µg/ml, 2 µg/ml, 3 µg/ml, 4 µg/ml, 5 µg/ml, 6 µg/ml, 7 µg/ml, 8 µg/ml, 9 µg/ml, 10 µg/ml, 15 µg/ml, 20 µg/ml, 25 µg/ml, 30 µg/ml, 40 µg/ml, 50 µg/ml, 60 µg/ml, 70 µg/ml, 80 µg/ml, 90 µg/ml, 100 µg/ml, 120 µg/ml, 140 µg/ml, 160 µg/ml, 180 µg/ml, 200 µg/ml, 250 µg/ml, 300 µg/ml, 400 µg/ml, 500 µg/ml, 600 µg/ml, 700 µg/ml, 800 µg/ml, 900 µg/ml, 1 mg/ml, 2 mg/ml, 3 mg/ml, 4 mg/ml, 5 mg/ml, 6 mg/ml, 7 mg/ml, 8 mg/ml, 9 mg/ml, 10 mg/ml, 15 mg/ml, 20 mg/ml, 25 mg/ml, 30 mg/ml, 40 mg/ml, 50 mg/ml, 60 mg/ml, 70 mg/ml, 80 mg/ml, 90 mg/ml, 100 mg/ml, or a greater concentration. In some cases, the nanoparticles are added to the DNA at a concentration less than about 1 ng/ml, 2 ng/ml, 3 ng/ml, 4 ng/ml, 5 ng/ml, 6 ng/ml, 7 ng/ml, 8 ng/ml, 9 ng/ml, 10 ng/ml, 15 ng/ml, 20 ng/ml, 25 ng/ml, 30 ng/ml, 40 ng/ml, 50 ng/ml, 60 ng/ml, 70 ng/ml, 80 ng/ml, 90 ng/ml, 100 ng/ml, 120 ng/ml, 140 ng/ml, 160 ng/ml, 180 ng/ml, 200 ng/ml, 250 ng/ml, 300 ng/ml, 400 ng/ml, 500 ng/ml, 600 ng/ml, 700 ng/ml, 800 ng/ml, 900 ng/ml, 1 µg/ml, 2 µg/ml, 3 µg/ml, 4 µg/ml, 5 µg/ml, 6 µg/ml, 7 µg/ml, 8 µg/ml, 9 µg/ml, 10 µg/ml, 15 µg/ml, 20 µg/ml, 25 µg/ml, 30 µg/ml, 40 µg/ml, 50 µg/ml, 60 µg/ml, 70 µg/ml, 80 µg/ml, 90 µg/ml, 100 µg/ml, 120 µg/ml, 140 µg/ml, 160 µg/ml, 180 µg/ml, 200 µg/ml, 250 µg/ml, 300 µg/ml, 400 µg/ml, 500 µg/ml, 600 µg/ml, 700 µg/ml, 800 µg/ml, 900 µg/ml, 1 mg/ml, 2 mg/ml, 3 mg/ml, 4 mg/ml, 5 mg/ml, 6 mg/ml, 7 mg/ml, 8 mg/ml, 9 mg/ml, 10 mg/ml, 15 mg/ml, 20 mg/ml, 25 mg/ml, 30 mg/ml, 40 mg/ml, 50 mg/ml, 60 mg/ml, 70 mg/ml, 80 mg/ml, 90 mg/ml, 100 mg/ml, or a greater concentration. In some cases, the nanoparticles are added to the DNA at a weight-to-weight (w/w) ratio greater than about 1:10000, 1:5000, 1:2000, 1:1000, 1:500, 1:200, 1:100, 1:50, 1:20, 1:10, 1:5, 1:2, 1:1, 2:1, 5:1, 10:1, 20:1, 50:1, 100:1, 200:1, 500:1, 1000:1, 2000:1, 5000:1, or 10000:1. In some cases, the nanoparticles are added to the DNA at a weight-to-weight (w/w) ratio less than about 1:10000, 1:5000, 1:2000, 1:1000, 1:500, 1:200, 1:100, 1:50, 1:20, 1:10, 1:5, 1:2, 1:1, 2:1, 5:1, 10:1, 20:1, 50:1, 100:1, 200:1, 500:1, 1000:1, 2000:1, 5000:1, or 10000:1. In some cases, the nanoparticles have a diameter greater than about 1 nm 1 nm, 2 nm, 3 nm, 4 nm, 5 nm, 6 nm, 7 nm, 8 nm, 9 nm, 10 nm, 15 nm, 20 nm, 25 nm, 30 nm, 40 nm, 50 nm, 60 nm, 70 nm, 80 nm, 90 nm, 100 nm, 120 nm, 140 nm, 160 nm, 180 nm, 200 nm, 250 nm, 300 nm, 400 nm, 500 nm, 600 nm, 700 nm, 800 nm, 900 nm, 1 µm, 2 µm, 3 µm, 4 µm, 5 µm, 6 µm, 7 µm, 8 µm, 9 µm, 10 µm, 15 µm, 20 µm, 25 µm, 30 µm, 40 µm, 50 µm, 60 µm, 70 µm, 80 µm, 90 µm, or 100 µm. In some cases, the nanoparticles have a diameter less than about 1 nm 1 nm, 2 nm, 3 nm, 4 nm, 5 nm, 6 nm, 7 nm, 8 nm, 9 nm, 10 nm, 15 nm, 20 nm, 25 nm, 30 nm, 40 nm, 50 nm, 60 nm, 70 nm, 80 nm, 90 nm, 100 nm, 120 nm, 140 nm, 160 nm, 180 nm, 200 nm, 250 nm, 300 nm, 400 nm, 500 nm, 600 nm, 700 nm, 800 nm, 900 nm, 1 µm, 2 µm, 3 µm, 4 µm, 5 µm, 6 µm, 7 µm, 8 µm, 9 µm, 10 µm, 15 µm, 20 µm, 25 µm, 30 µm, 40 µm, 50 µm, 60 µm, 70 µm, 80 µm, 90 µm, or 100 µm.

Furthermore, in some cases, the nanoparticles are immobilized on solid substrates (e.g. beads, slides, or tube walls) by applying magnetic fields (in the case of paramagnetic nanoparticles) or by covalent attachment (e.g. by cross-linking to poly-lysine coated substrate). Immobilization of the nanoparticles improves the ligation efficiency thereby increasing the number of desired products (signal) relative to undesired (noise).

In various cases, the methods disclosed herein are used to produce read-sets comprising reads that are separated by large distances. The upper limit of this distance may be improved by the ability to collect DNA samples of large size. In some cases, the reads are separated by up to 50 kb, 60 kb, 70 kb, 80 kb, 90 kb, 100 kb, 125 kb, 150 kb, 175 kb, 200 kb, 225 kb, 250 kb, 300 kb, 400 kb, 500 kb, 600 kb, 700 kb, 800 kb, 900 kb, 1 Mb, 1.5 Mb, 2 Mb, 2.5 Mb, 3 Mb, 4 Mb, 5 Mb or more in genomic distance. In some cases, the reads are separated by up to 500 kb in genomic distance. In other cases, the reads are separated by up to 2 Mb in genomic distance. The methods disclosed herein can integrate and build upon standard techniques in molecular biology, and are further well-suited for increases in efficiency, specificity, and genomic coverage. In some cases, the read-sets are generated in less than about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 60, or 90 days. In some cases, the read-sets are generated in less than about 14 days. In further cases, the read-sets are generated in less about 10 days. In some cases, the methods of the present disclosure provide greater than about 5%, about 10%, about 15%, about 20%, about 30%, about 40%, about 50%, about 60%, about 70%, about 80%, about 90%, about 95%, about 99%, or about 100% of the read pairs with at least about 50%, about 60%, about 70%, about 80%, about 90%, about 95%, about 99%, or about 100% accuracy in correctly ordering and/or orientating the plurality of contigs and/or scaffolds. In some cases, the methods provide about 90 to 100% accuracy in correctly ordering and/or orientating the plurality of contigs and/or scaffolds.

In some embodiments, nanoparticles are cross-linked to the DNA fragment in an in vitro complex, and wherein the in vitro complex is immobilized on a solid support. In other aspects, the present disclosure provides a composition comprising a DNA fragment, a plurality of nanoparticles, and a DNA-binding molecule, wherein the DNA-binding molecule is bound to a predetermined sequence of the DNA fragment, and wherein the nanoparticles are cross-linked to the DNA fragment. In some cases, the DNA-binding molecule is a nucleic acid that can hybridize to the predetermined sequence. In some cases, the nucleic acid is RNA. In other cases, the nucleic acid is DNA. In further cases, the DNA-binding molecule is a small molecule. In some cases, the DNA-binding molecule is protein histone. In some cases, the nanoparticle is any nanoparticles described herein. In some embodiments, the small molecule binds to the predetermined sequence with a binding affinity less than 100 µM. In further embodiments, small molecule binds to the predetermined sequence with a binding affinity less than 1 µM. In certain cases, the nucleic acid is immobilized to a surface or a solid support.

In some cases, the method also comprises ligating a barcoded aggregate to the DNA complex. In some cases, the barcoded aggregate comprises a plurality of barcoded polynucleotides and a plurality of aggregate molecules. In further examples, the barcoded polynucleotides are generated using Rolling Circle Amplification (RCA). In some cases, each of the barcoded polynucleotides in the barcoded aggregate comprises an identical barcode. In further cases, the barcoded polynucleotides in the barcoded aggregate are identical. In some cases, the barcoded polynucleotides are ligated to the first sequence segment and the second sequence segment. In further cases, the first sequence segment and the second sequence segment are amplified using the barcoded polynucleotides as templates. In some cases, the barcoded polynucleotides comprise the first and the second label, which can comprise an identical barcode. In some cases, the aggregate molecules comprise amino acids. In further cases, the aggregate molecules comprise peptides or proteins (e.g. histones). In other cases, the aggregate molecules comprise nanoparticles. The nanoparticles can be any nanoparticles as described herein. In some cases, a sequencing adaptor is further linked to the first sequence segment and/or the second sequence segment. In some cases, the sequence information of the first sequence segment and the second sequence segment is obtained by a sequencing method. The sequencing method can be any known sequencing method in the art, including but not limited to the sequencing technologies disclosed in the present application. Using the sequence information, in some cases, the first sequence segment and the second sequence segment are associated to one another. In some cases, the first sequence segment and the second sequence segment comprise a same label and are binned into a read-set. In some cases, the sequence information is also used to assemble a plurality of contigs and/or scaffolds. In certain cases, the sequence information is used to assemble the first DNA molecule. In further cases, the sequence information is used to assemble a genome. In some cases, the genome is assembled by aligning reads to a reference genome, or by de novo assembly. In some cases, methods that produce fragments of genomic DNA up to megabase scale are used with the methods disclosed herein. Long DNA fragments can be generated to confirm the ability of the present methods to generate read pairs spanning the longest fragments offered by those extractions. In some cases, DNA fragments beyond 150 kb in length are extracted and used to generate XLRP libraries.

In some embodiments, sequence tag information is used to map sequence reads to a single nucleic acid molecule from which they originated. In some embodiments, this information is independent of distance information within a single nucleic acid molecule. In some cases, the nucleic acid molecule is obtained from a population of incompletely fragmented or sheared genomic DNA, which is sheared such that overlapping nucleic acid fragments are obtained. Upon sequencing the reads which correspond to each individual overlapping nucleic acid molecule, one may assemble larger 'read position contig' information to infer phase or physical linkage information across distances beyond single sheared nucleic acid size.

The intrachromosomal interactions can be used to correlate chromosomal connectivity. Similarly, the nucleic acid fragment mapping data can be used to correlate chromosomal connectivity. Further, the intrachromosomal data can aid genomic assembly. In some cases, the chromatin is reconstructed in vitro. This can be advantageous because chromatin—particularly histones, the major protein component of chromatin—is important for DNA fixation. In some cases, chromatin forms a stable complex with DNA to capture the spatial and sequence information, which is analyzed to aid genomic assembly. Chromatin is highly non-specific in terms of sequence and can be generally assemble uniformly across the genome. In some cases, the genomes of species that do not use chromatin are assembled on a reconstructed chromatin and thereby extend the horizon for the disclosure to all domains of life.

In some cases, cross-links are created between genome regions that are in close physical proximity. Crosslinking of proteins (e.g. histones) to the DNA molecule (e.g. genomic DNA), within chromatin is accomplished according to a suitable method described in further detail elsewhere herein or otherwise known in the art. In some cases, two or more nucleotide sequences are cross-linked via proteins bound to one or more nucleotide sequences. One approach is to expose the chromatin to ultraviolet irradiation (Gilmour et al., Proc. Nat'l. Acad. Sci. USA 81:4275-4279, 1984). Crosslinking of polynucleotide segments may also be performed utilizing other approaches, such as chemical or physical (e.g. optical) crosslinking. Suitable chemical cross-linking agents include, but are not limited to, formaldehyde and psoralen (Solomon et al., Proc. Natl. Acad. Sci. USA 82:6470-6474, 1985; Solomon et al., Cell 53:937-947, 1988). For example, cross-linking can be performed by adding a solution comprising about 2% formaldehyde to a mixture comprising the DNA molecule and chromatin proteins. Other cases of agents that are used to cross-link DNA include, but are not limited to, UV light, mitomycin C, nitrogen mustard, melphalan, 1,3-butadiene diepoxide, cis diaminedichloroplatinum(II) and cyclophosphamide. In further cases, the cross-linking agent forms cross-links that bridge relatively short distances—such as about 2 Å—thereby selecting intimate interactions that can be reversed.

In some cases, the DNA molecule is immunoprecipitated prior to or after crosslinking. In some cases, the DNA molecule is fragmented into two or more sequence segments. In further cases, sequence segments are contacted with a binding partner, such as an antibody that specifically recognizes and binds to acetylated histones, e.g., H3. Cases of such antibodies include, but are not limited to, Anti Acetylated Histone H3, available from Upstate Biotechnology, Lake Placid, N.Y. In some cases, the polynucleotides from the immunoprecipitate are subsequently collected from the immunoprecipitate. In some cases, prior to fragmenting the polynucleotide, the acetylated histones are cross-linked to adjacent polynucleotide sequences. In further cases, the mixture is then treated to fractionate polynucleotides in the mixture. Fractionation techniques are known in the art and include, for example, shearing techniques to generate smaller genomic fragments. Fragmentation can be accomplished using established methods for fragmenting chromatin, including, for example, sonication, shearing, contacting with enzymes or other chemicals having nonspecific endonuclease activity and/or the use of restriction enzymes. In some cases, the restriction enzyme has a restriction recognition site of 1, 2, 3, 4, 5, 6, 7, 8, or more than 8 bases long. Examples of restriction enzymes include, but are not limited to, AatII, Acc65I, AccII, AciI, AclI, AcuI, AfeI, AflII, AflIII, AgeI, AhdI, AleI, AluI, AlwI, AlwNI, ApaI, ApaLI, ApeKI, ApoI, AscI, AseI, AsiSI, AvaI, AvaII, AvrII, BaeGI, BaeI, BamHI, BanI, BanII, BbsI, BbvCI, BbvI, BccI, BceAI, BcgI, BciVI, BclI, BfaI, BfuAI, BfuCI, BglI, BglII, BlpI, BmgBI, BmrI, BmtI, BpmI, Bpu10I, BpuEI, BsaAI, BsaBI, BsaHI, BsaI, BsaJI, BsaWI, BsaXI, BscRI, BscYI, BsgI, BsiEI, BsiHKAI, BsiWI, BslI, BsmAI, BsmbI, BsmFI, BsmI, BsoBI, Bsp1286I, BspCNI, BspDI, BspEI, BspHI, BspMI, BspQI, BsrBI, BsrDI, BsrFI, BsrGI, BsrI, BssHII, BssKI, BssSI, BstAPI, BstBI, BstEII, BstNI, BstUI, BstXI, BstYI, BstZ17I, Bsu36I, BtgI, BtgZI, BtsCI, BtsI, Cac8I, ClaI, CspCI, CviAII, CviKI-1, CviQI, DdcI, DpnI, DpnII, DraI, DraIII, DrdI, EacI, EagI, EarI, EciI, Eco53kI, EcoNI, EcoO109I, EcoP15I, EcoRI, EcoRV, FatI, FauI, Fnu4HI, FokI, FseI, FspI, HaeII, HaeIII, HgaI, HhaI, HincII, HindIII, HinfI, HinPII, HpaI, HpaII, HphI, Hpy166II, Hpy188I, Hpy188III, Hpy99I, HpyAV, HpyCH4III, HpyCH4IV, HpyCH4V, KasI, KpnI, MboI, MboII, MfeI, MluI, MlyI, MmeI, MnlI, MscI, MseI, MslI, MspA1I, MspI, MwoI, NaeI, NarI, Nb.BbvCI, Nb.BsmI, Nb.BsrDI, Nb.BtsI, NciI, NcoI, NdeI, NgoMIV, NheI, NlaIII, NlaIV, NmeAIII, NotI, NruI, NsiI, NspI, Nt.AlwI, Nt.BbvCI, Nt.BsmAI, Nt.BspQI, Nt.B-stNBI, Nt.CviPII, PacI, PaeR7I, PciI, PflFI, PflMI, PhoI, PleI, PmeI, PmlI, PpuMI, PshAI, PsiI, PspGI, PspOMI, PspXI, PstI, PvuI, PvuII, RsaI, RsrII, SacI, SacII, SalI, SapI, Sau3AI, Sau96I, SbfI, ScaI, ScrFI, SexAI, SfaNI, SfcI, SfiI, SfoI, SgrAI, SmaI, SmlI, SnaBI, SpeI, SphI, SspI, StuI, StyD4I, StyI, SwaI, T, Taqαl, TfiI, TliI, TseI, Tsp45I, Tsp509I, TspMI, TspRI, Tth111I, XbaI, XcmI, XhoI, XmaI, XmnI, and ZraI. The resulting sequence segments can vary in size. The resulting sequence segments may also comprise a single-stranded overhand at the 5' or 3' end.

In some embodiments, using sonication techniques, sequence segments of about 100 to 5000 nucleotides are obtained. Alternatively, sequence segments of about 100 to 1000, about 150 to 1000, about 150 to 500, about 200 to 500, or about 200 to 400 nucleotides are obtained. The sample can be prepared for sequencing the cross-linked sequence segments. In some cases, sequence segments that were intramolecularly cross-linked are labeled with a common label. The common label can then be detected and analyzed to determine sequence segments that were intramolecularly cross-linked. The common label can, for example, be a barcode, which can optionally be detected by sequencing methods. In some cases, the reads of sequence segments labeled with a common label are binned into a read-set.

Sequence information is obtained from the sample using any suitable sequencing technique described in further detail elsewhere herein or otherwise known in the art, such as a high throughput sequencing method. In some cases, the sequence segments are subject to a sequencing technique to generate sequence reads, which are used to identify sequence segments that are cross-linked and/or are labeled with a common label. In further cases, two or more sequence segments are represented in the obtained sequence information, associating haplotyping information over a linear distance separating the two sequence segments along the polynucleotide.

In some cases, the methods disclosed herein are used in combination with an existing sequencing technology. In further cases, the methods disclosed herein are used with technologies and approaches derived from any existing sequencing technology. Cases of sequencing technologies that can be used with the methods disclosed herein include, but are not limited to, the Illumina® sequencing-by-synthesis platform (Illumina, San Diego, Calif.), the SOLiD™ system (Applied Biosystems Corp.), pyrosequencing (e.g., 454 Life Sciences, subsidiary of Roche Diagnostics), a sequencing technique based on semiconductor detectors (e.g., the Ion Torrent® platform), nanopore sequencing (e.g., the Oxford Nanopore sequencing platform), DNA nanoball sequencing methods (e.g. Complete Genomics), long-read sequencing such as Pacific Biosciences (PacBio), sequencing by hybridization and any other suitable technology, or any technology that may be derived from any of the above technologies.

In addition to species-specific and cell type-specific chromatin interactions, two canonical interaction patterns have been observed in most chromatin capture techniques. One pattern, distance-dependent decay (DDD), is a general trend of decay in interaction frequency as a function of genomic distance. The second pattern, cis-trans ratio (CTR), is a significantly higher interaction frequency between loci located on the same chromosome, even when separated by tens of megabases of sequence, versus loci on different chromosomes. These patterns may reflect general polymer dynamics, where proximal loci have a higher probability of randomly interacting, as well as specific nuclear organization features such as the formation of chromosome territories, the phenomenon of interphase chromosomes tending to occupy distinct volumes in the nucleus with little mixing. Although the exact details of these two patterns may vary between species, cell types and cellular conditions, they are ubiquitous and prominent. These patterns are so strong and consistent that they are used to assess experiment quality and are usually normalized out of the data in order to reveal detailed interactions. However, in the methods disclosed herein, genome assembly can take advantage of the three-dimensional structure of genomes. In certain cases, the ubiquity, strength and consistency of these features are used as powerful tools for estimating the genomic position of contigs and/or scaffolds.

Figure 3:
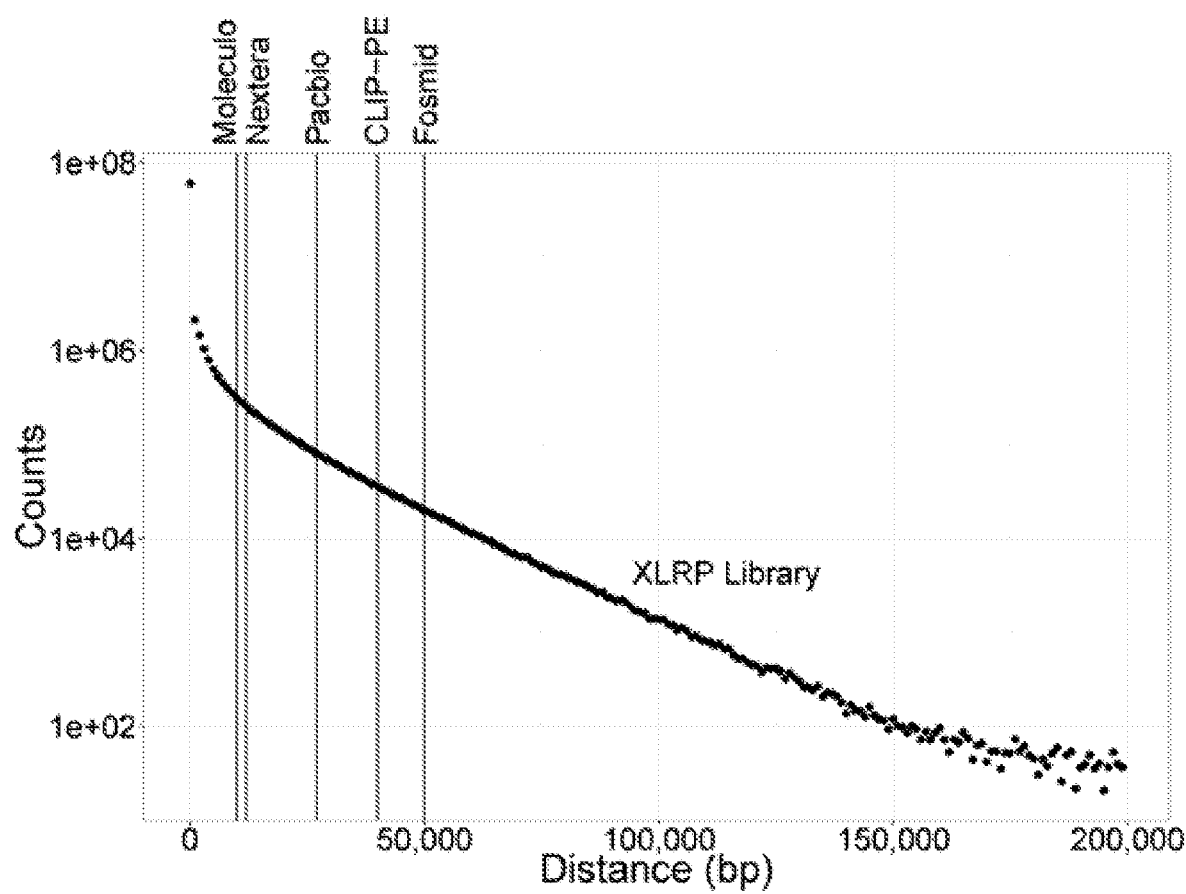
FIG. 3 illustrates the distribution of genomic distances between read pairs from a human XLRP library. Maximum distances achievable with other technologies are indicated for comparison.

In particular cases, examination of the physical distance between intrachromosomal read pairs indicates several useful features of the data with respect to genome assembly. First, shorter range interactions are more common than longer-range interactions (FIG. 3). That is, each read of a read-pair is more likely to be mated with a region close by in the actual genome than it is to be with a region that is far away. Second, there is a long tail of intermediate and long-range interactions. That is, read pairs carry information about intrachromosomal arrangement at kilobase (kb) or even megabase (Mb) distances. In some cases, read pairs provide sequence information over a span of greater than about 10 kb, about 50 kb, about 100 kb, about 200 kb, about 500 kb, about 1 Mb, about 2 Mb, about 5 Mb, about 10 Mb, or about 100 Mb. These features of the data simply indicate that regions of the genome that are nearby on the same chromosome are more likely to be in close physical proximity—an expected result because they are chemically linked to one another through the DNA backbone. It was speculated that genome-wide chromatin interaction data sets, such as those generated by chromatin capture methods, would provide long-range information about the grouping and linear organization of sequences along entire chromosomes.

The present disclosure provides a method to determine haplotype phasing. In some cases, the method comprises a step of identifying one or more sites of heterozygosity in the plurality of read pairs, wherein phasing data for allelic variants are determined by identifying read pairs that comprise a pair of heterozygous sites.

In diploid genomes, it is often important to know which allelic variants are physically linked on the same chromosome rather than mapping to the homologous position on a chromosome pair. Mapping an allele or other sequence to a specific physical chromosome of a diploid chromosome pair is known as the haplotype phasing. Short reads from high-throughput sequence data rarely allow one to directly observe which allelic variants are linked, particularly, as is most often the case, if the allelic variants are separated by a greater distance than the longest single read. Computational inference of haplotype phasing can be unreliable at long distances. Methods disclosed herein allow for preserving or preparing nucleic acids for determining which allelic variants are physically linked using allelic variants on read pairs.

In various cases, the methods and compositions of the disclosure enable the haplotype phasing of diploid or polyploid genomes with regard to a plurality of allelic variants. Methods described herein thus provide for the determination of linked allelic variants based on variant information from labeled sequence segments and/or assembled contigs and/or scaffolds using the same. Cases of allelic variants include, but are not limited to, those that are known from the 1000 genomes, UK10K, HapMap and other projects for discovering genetic variation among humans. In some cases, disease association to a specific gene are revealed more easily by having haplotype phasing data as demonstrated, for example, by the finding of unlinked, inactivating mutations in both copies SH3TC2 leading to Charcot-Marie-Tooth neuropathy (Lupski J R, Reid J G, Gonzaga-Jauregui C, et al. *N. Engl. J. Med.* 362:1181-91, 2010) and unlinked, inactivating mutations in both copies of ABCG5 leading to hypercholesterolemia 9 (Rios J, Stein E, Shendure J, et al. *Hum. Mol. Genet.* 19:4313-18, 2010).

Humans are heterozygous at an average of 1 site in 1,000. In some cases, a single lane of data using high throughput sequencing methods generates at least about 150,000,000 reads. In further cases, individual reads are about 100 base pairs long. If we assume input DNA fragments average 150 kb in size and we get 100 paired-end reads per fragment, then we expect to observe 30 heterozygous sites per set, i.e., per 100 read pairs. Every read-pair containing a heterozygous site within a set is in phase (i.e., molecularly linked) with respect to all other read pairs within the same set. This property enables greater power for phasing with sets as opposed to singular pairs of reads in some cases. With approximately 3 billion bases in the human genome, and one in one-thousand being heterozygous, there are approximately 3 million heterozygous sites in an average human genome. With about 45,000,000 read pairs that contain heterozygous sites, the average coverage of each heterozygous site to be phased using a single lane of a high throughput sequence method is about (15×), using a typical high throughput sequencing machine. A diploid human genome can therefore be reliably and completely phased with one lane of a high-throughput sequence data relating sequence variants from a sample that is prepared using the methods disclosed herein. In some cases, a lane of data is a set of DNA sequence read data. In further cases, a lane of data is a set of DNA sequence read data from a single run of a high throughput sequencing instrument.

As the human genome consists of two homologous sets of chromosomes, understanding the true genetic makeup of an individual requires delineation of the maternal and paternal copies or haplotypes of the genetic material. Obtaining a haplotype in an individual is useful in several ways. For example, haplotypes are useful clinically in predicting outcomes for donor-host matching in organ transplantation. Haplotypes are increasingly used to detect disease associations. In genes that show compound heterozygosity, haplotypes provide information as to whether two deleterious variants are located on the same allele (that is, 'in cis', to use genetics terminology) or on two different alleles ('in trans'), greatly affecting the prediction of whether inheritance of these variants is harmful, and impacting conclusions as to whether an individual carries a functional allele and a single nonfunctional allele having two deleterious variant positions, or whether that individual carries two nonfunctional alleles, each with a different defect. Haplotypes from groups of individuals have provided information on population structure of interest to both epidemiologists and anthropologists and informative of the evolutionary history of the human race. In addition, widespread allelic imbalances in gene expression have been reported, and suggest that genetic or epigenetic differences between allele phases may contribute to quantitative differences in expression. An understanding of haplotype structure will delineate the mechanisms of variants that contribute to allelic imbalances.

In certain embodiments, the methods disclosed herein comprise an in vitro technique to fix and capture associations among distant regions of a genome as needed for long-range linkage and phasing following DNA damage. In some cases, the method comprises constructing and sequencing one or more read-sets to deliver very genomically distant read pairs. In further cases, each read-set comprises two or more reads that are labeled by a common barcode, which may represent two or more sequence segments from a common polynucleotide. In some cases, the interactions primarily arise from the random associations within a single polynucleotide. In some cases, the genomic distance between sequence segments are inferred because sequence segments near to each other in a polynucleotide interact more often and with higher probability, while interactions between distant portions of the molecule are less frequent. Consequently there is a systematic relationship between the number of pairs connecting two loci and their proximity on the input DNA. In some cases, the methods disclosed herein produce read pairs that span the largest DNA fragments in an extraction, as demonstrated in FIG. 1A-AG. The input DNA for this library had a maximum length of 150 kb, which is the longest meaningful read pair we observe from the sequencing data. This suggests that the present method can link still more genomically distant loci if provided larger input DNA fragments. By applying improved assembly software tools that are specifically adapted to handle the type of data produced by the present method, a complete genomic assembly may be possible. Methods disclosed herein are used in some embodiments to label sequence segments and/or to preserve labeled sequence segments that span the largest polynucleotide from an extraction.

In some aspects, the disclosure provides methods and compositions that produce data to achieve extremely high phasing accuracy. In comparison to previous methods, the methods described herein can phase a higher proportion of the variants. In some cases, phasing is achieved while maintaining high levels of accuracy. In further cases, this physical linkage information is extended to longer ranges, for example greater than about 200 kb, about 300 kb, about 400 kb, about 500 kb, about 600 kb, about 700 kb, about 800 kb, about 900 kb, about 1 Mb, about 2 Mb, about 3 Mb, about 4 Mb, about 5 Mb, or about 10 Mb, or longer than about 10 Mb, up to and including the entire length of a chromosome. In some embodiments, more than 90% of the heterozygous SNPs for a human sample is phased at an accuracy greater than 99% using less than about 250 million reads, e.g. by using only 1 lane of Illumina HiSeq data. In other cases, more than about 40%, 50%, 60%, 70%, 80%, 90%, 95% or 99% of the heterozygous SNPs for a human sample is phased at an accuracy greater than about 70%, 80%, 90%, 95%, or 99% using less than about 250 million or about 500 million reads, e.g. by using only 1 or 2 lanes of Illumina HiSeq data. In some cases, more than 95% or 99% of the heterozygous SNPs for a human sample are phased at an accuracy greater than about 95% or 99% using less about 250 million or about 500 million reads. In further cases, additional variants are captured by increasing the read length to about 200 bp, 250 bp, 300 bp, 350 bp, 400 bp, 450 bp, 500 bp, 600 bp, 800 bp, 1000 bp, 1500 bp, 2 kb, 3 kb, 4 kb, 5 kb, 10 kb, 20 kb, 50 kb, or 100 kb.

Accordingly, methods disclosed herein may be applied to intact human genomic DNA samples but may also be applied to a broad diversity of nucleic acid samples, such as reverse-transcribed RNA samples, circulating free DNA samples, cancer tissue samples, crime scene samples, archaeological samples, nonhuman genomic samples, or environmental samples such as environmental samples comprising genetic information from more than one organism, such as an organism that is not easily cultured under laboratory conditions.

In some cases, high degrees of accuracy required by cancer genome sequencing are achieved using the methods and systems described herein. Inaccurate reference genomes make base-calling challenges when sequencing cancer genomes. Heterogeneous samples and small starting materials, for example a sample obtained by biopsy introduce additional challenges. Further, detection of large scale structural variants and/or losses of heterozygosity is often crucial for cancer genome sequencing, as well as the ability to differentiate between somatic variants and errors in base-calling.

The systems and methods described herein may generate accurate long sequences from complex samples containing 2, 3, 4, 5, 6, 7, 8, 9, 10, 12, 15, 20 or more than 20 varying genomes. Mixed samples of normal, benign, and/or tumor origin may be analyzed, optionally without the need for a normal control. In some embodiments, samples comprising less than about 1000 ng, about 500 ng, about 200 ng, about 100 ng, about 50 ng, about 20 ng, about 10 ng, or even as little as hundreds of genome equivalents, are utilized to generate accurate long sequences. Systems and methods described herein may allow for detection of large scale structural variants and rearrangements, Phased variant calls may be obtained over long sequences spanning about 1 kb, about 2 kb, about 5 kb, about 10 kb, 20 kb, about 50 kb, about 100 kb, about 200 kb, about 500 kb, about 1 Mb, about 2 Mb, about 5 Mb, about 10 Mb about 20 Mb, about 50 Mb, or about 100 Mb or more nucleotides. For example, a phase variant call may be obtained over long sequences spanning about 1 Mb or about 2 Mb.

In certain aspects, the methods disclosed herein are used to assemble a plurality of contigs and/or scaffolds originating from a single DNA molecule. In some cases, the method comprises generating a plurality of read pairs from the single DNA molecule that is cross-linked to a plurality of nanoparticles and assembling the contigs and/or scaffolds using the read pairs. In certain cases, single DNA molecule is cross-linked outside of a cell. In some cases, at least 0.1%, 0.2%, 0.3%, 0.4%, 0.5%, 0.6%, 0.7%, 0.8%, 0.9%, 1%, 2%, 3%, 4%, 5%, 6%, 7%, 8%, 9%, 10%, 11%, 12%, 13%, 14%, 15%, 16%, 17%, 18%, 19%, 20%, 25%, 30%, 35%, 40%, 45%, or 50% of the read pairs span a distance greater than 1 kb, 2 kb, 3 kb, 4 kb, 5 kb, 6 kb, 7 kb, 8 kb, 9 kb, 10 kb, 15 kb, 20 kb, 30 kb, 40 kb, 50 kb, 60 kb, 70 kb, 80 kb, 90 kb, 100 kb, 150 kb, 200 kb, 250 kb, 300 kb, 400 kb, 500 kb, 600 kb, 700 kb, 800 kb, 900 kb, or 1 Mb on the single DNA molecule. In certain cases, at least 0.5%, 0.6%, 0.7%, 0.8%, 0.9%, 1%, 2%, 3%, 4%, 5%, 6%, 7%, 8%, 9%, 10%, 11%, 12%, 13%, 14%, 15%, 16%, 17%, 18%, 19%, or 20% of the read pairs span a distance greater than 5 kb, 6 kb, 7 kb, 8 kb, 9 kb, 10 kb, 15 kb, 20 kb, 30 kb, 40 kb, 50 kb, 60 kb, 70 kb, 80 kb, 90 kb, 100 kb, 150 kb, or 200 kb on the single DNA molecule. In further cases, at least 0.5%, 0.6%, 0.7%, 0.8%, 0.9%, 1%, 2%, 3%, 4%, or 5% of the read pairs span a distance greater than 20 kb, 30 kb, 40 kb, 50 kb, 60 kb, 70 kb, 80 kb, 90 kb, or 100 kb on the single DNA molecule. In particular cases, at least 1% or 5% of the read pairs span a distance greater than 50 kb or 100 kb on the single DNA molecule. In some cases, the read pairs are generated within 1, 2, 3, 4, 5, 6, 7, 8, 9, 10, 11, 12, 13, 14, 15, 16, 17, 18, 19, 20, 30, 40, 50 or 60 days. In certain cases, the read pairs are generated within 3, 4, 5, 6, 7, 8, 9, 10, 11, 12, 13, 14, 15, 16, 17 or 18 days. In further cases, the read-pairs are generated within 7, 8, 9, 10, 11, 12, 13, or 14 days. In particular cases, the read pairs are generated within 7 or 14 days.

In other aspects, the methods disclosed herein are used for haplotype phasing. In some cases, the method comprises generating a plurality of read pairs from a single DNA molecule that is bound to a plurality of nanoparticles and cross-linked, and assembling a plurality of contigs and/or scaffolds of the DNA molecule using the read pairs. In certain cases, single DNA molecule is subjected to cross-linking outside of a cell. In some cases, at least 0.1%, 0.2%, 0.3%, 0.4%, 0.5%, 0.6%, 0.7%, 0.8%, 0.9%, 1%, 2%, 3%, 4%, 5%, 6%, 7%, 8%, 9%, 10%, 11%, 12%, 13%, 14%, 15%, 16%, 17%, 18%, 19%, 20%, 25%, 30%, 35%, 40%, 45%, or 50% of the read pairs span a distance greater than 1 kb, 2 kb, 3 kb, 4 kb, 5 kb, 6 kb, 7 kb, 8 kb, 9 kb, 10 kb, 15 kb, 20 kb, 30 kb, 40 kb, 50 kb, 60 kb, 70 kb, 80 kb, 90 kb, 100 kb, 150 kb, 200 kb, 250 kb, 300 kb, 400 kb, 500 kb, 600 kb, 700 kb, 800 kb, 900 kb, or 1 Mb on the single DNA molecule. In certain cases, at least 0.5%, 0.6%, 0.7%, 0.8%, 0.9%, 1%, 2%, 3%, 4%, 5%, 6%, 7%, 8%, 9%, 10%, 11%, 12%, 13%, 14%, 15%, 16%, 17%, 18%, 19%, or 20% of the read pairs span a distance greater than 5 kb, 6 kb, 7 kb, 8 kb, 9 kb, 10 kb, 15 kb, 20 kb, 30 kb, 40 kb, 50 kb, 60 kb, 70 kb, 80 kb, 90 kb, 100 kb, 150 kb, or 200 kb on the single DNA molecule. In further cases, at least 0.5%, 0.6%, 0.7%, 0.8%, 0.9%, 1%, 2%, 3%, 4%, or 5% of the read pairs span a distance greater than 20 kb, 30 kb, 40 kb, 50 kb, 60 kb, 70 kb, 80 kb, 90 kb, or 100 kb on the single DNA molecule. In particular cases, at least 1% or 10% of the read pairs span a distance greater than 30 kb or 50 kb on the single DNA molecule. Often, the haplotype phasing is performed at greater than 70% accuracy. In some embodiments, at least 10% of the read pairs span a distance greater than 50 kb on the single DNA molecule. In other embodiments, wherein at least 1% of the read pairs span a distance greater than 100 kb on the single DNA molecule. In some cases, the haplotype phasing is performed at greater than 50%, 60%, 70%, 75%, 80%, 85%, 90%, 95%, 96%, 97%, 98%, or 99% accuracy. In certain cases, the haplotype phasing is performed at greater than 70%, 75%, 80%, 85%, 90%, or 95% accuracy. In further cases, the haplotype phasing is performed at greater than 70%, or 90% accuracy.

Haplotypes determined using the methods and systems described herein may be assigned to computational resources, for example, computational resources over a network, such as a cloud system. Similarly, in certain cases, contig and/or scaffold information is obtained using computational resources such as cloud system resources. Short variant calls are corrected, if necessary, using relevant information that is stored in the computational resources. In some cases, structural variants are detected based on the combined information from short variant calls and the information stored in the computational resources. In some cases, problematic parts of the genome, such as segmental duplications, regions prone to structural variation, the highly variable and medically relevant MHC region, centromeric and telomeric regions, and other heterochromatic regions including but limited to those with repeat regions, low sequence accuracy, high variant rates, ALU repeats, segmental duplications, or any other relevant problematic parts known in the art, are assembled or reassembled for increased accuracy.

In some cases, a sample type is assigned to the sequence information either locally or in a networked computational resource, such as a cloud. In cases where the source of the information is known, for example, when the source of the information is from a cancer or normal tissue, the source is assigned to the sample as part of a sample type. Other sample type cases generally include, but are not limited to, tissue type, sample collection method, presence of infection, type of infection, processing method, size of the sample, etc. In cases where a complete or partial comparison genome sequence is available, such as a normal genome in comparison to a cancer genome, the differences between the sample data and the comparison genome sequence is determined and optionally output.

In some embodiments, haplotype phasing comprises the steps of associating a first sequence segment and a second sequence segment. In some cases, the methods comprise: a. crosslinking a DNA library comprising a first DNA molecule, wherein the first DNA molecule comprises the first sequence segment and the second sequence segment; b. isolating the first sequence segment and the second sequence segment in a first reaction volume; and c. attaching a first label to the first sequence segment and a second label to the second sequence segment. In some cases, the methods comprise: a. crosslinking a DNA library comprising a first DNA molecule, wherein the first DNA molecule comprises the first sequence segment and the second sequence segment; b. isolating the first sequence segment and the second sequence segment in a first reaction volume; c. releasing the first sequence segment and the second sequence segment from the crosslinking; and d. linking the first sequence segment and the second sequence segment.

In some cases, the methods further comprise severing the first DNA molecule. Methods for severing the first DNA molecule are described elsewhere in the present application. In some cases, the first DNA molecule is severed into the first sequence segment and the second sequence segment, which may have blunt-ends or overhangs. In some cases, the overhangs are filled in by modified nucleotides, such as sulfated or biotinylated nucleotides. In some cases, adaptor oligonucleotides are hybridized and/or ligated to the blunt-ends or overhangs. The adaptor oligonucleotides can be any known adaptor in the art, including but not limited to those disclosed in the present application.

In some cases, the first sequence segment and the second sequence segment are cross-linked to a plurality of association molecules. Examples of association molecules are as described elsewhere in the present application. In some cases, the association molecules comprise amino acids. In further examples, the association molecules comprise peptides or proteins (e.g. histones, or packing proteins such as H1 and protamine).

In some cases, the first reaction volume comprises a single DNA molecule and not any other DNA molecule. In some cases, the DNA library comprises a plurality of DNA molecules that are isolated in a plurality of reaction volumes. In further cases, the DNA molecules are isolated in the reaction volumes under conditions such that a substantial percentage of the reaction volumes comprise a single DNA molecule or no DNA molecules at all. In some cases, more than about 50%, about 60%, about 70%, about 75%, about 80%, about 85%, about 90%, about 91%, about 92%, about 93%, about 94%, about 95%, about 96%, about 97%, about 98%, about 99%, about 99.9%, or more of the reaction volumes comprise 0 or 1 DNA molecules.

In some cases, the first label and the second label are identical. In other cases, the first label and the second label are different. In some cases, the first label and the second label are polynucleotides. In further examples, the first label and the second label each comprise one or more elements selected from the group consisting of a primer, a barcode and a restriction site. In some cases, the first label and the second label each comprise a barcode. In further examples, the labels comprise specific sequences indicating the location of the barcode. In certain cases, the first label and the second label are produced from a template in the first reaction volume. In some cases, the first label and the second label are produced by amplification of a linear template (e.g. PCR). In other cases, the first label and the second label are produced by Rolling Circle Amplification (RCA) of a circular template. In further cases, the RCA product is further digested to yield a plurality of labels. In some cases, the labels are digested or modified (e.g. adenylated), such as to generate complementary overhangs for attachment to the sequence segments. In certain cases, the labels are attached to the sequence segments by ligation or by hybridization and extension with a DNA polymerase. In further cases, the labels are attached directly to the sequence segments, or indirectly to adaptor oligonucleotides that are ligated or hybridized to the sequence segments.

In some cases, the first sequence segment and the second sequence segment are released from the crosslinking using heat or chemical agents. In certain cases, the crosslinks are reversed. In some cases, the first sequence segment and the second sequence segment are further digested to generate new ends (e.g. with a different restriction enzyme). In further cases, the first sequence segment and the second sequence segment are hybridized and/or linked by a ligase. In some cases, the sequence segments within a single reaction volume link to one another and generate many hybrid molecules. In some cases, the linked sequence segments may be previously distant on the original DNA molecule.

In certain cases, sequencing adaptors are further linked to the first sequence segment and/or the second sequence segment. In some cases, the sequence information of the first sequence segment and/or the second sequence segment are obtained by a sequencing method. The sequencing method can be any known sequencing method in the art, including but not limited to the sequencing technologies disclosed in the present application. In some cases, the sequencing method is a microarray analysis (e.g. comparative hybridization) or a high-throughput sequencing technique. Using the sequence information, in some cases, the first sequence segment and the second sequence segment are associated to one another. In some cases, the first sequence segment and the second sequence segment comprise a same barcode and are binned into a read-set. In further examples, the first sequence segment and the second sequence segment are associated based on the first label and the second label. In some cases, the sequence information is also used to assemble a plurality of contigs and/or scaffolds. In certain cases, the sequence information is used to assemble the first DNA molecule. In further cases, the sequence information is used to assemble a genome. In some cases, the genome is assembled by aligning reads to a reference genome, or by de novo assembly.

In some cases, the labeled or linked sequence segments is analyzed and/or characterized. In some cases, the labeled or linked sequence segments are isolated (e.g. by phase separation), filtered and/or washed to retain only the sequence segments of interest. In some cases, the size of the DNA molecules in the DNA library are estimated (e.g. by gel electrophoresis or pulsed field gel electrophoresis (PFGE)) and used to calculate an expected range (in base pairs) of the sequence segments.

In the realm of personalized medicine, the XLRS read-sets generated from the methods disclosed herein represents a meaningful advance toward accurate, low-cost, phased, and rapidly produced personal genomes. Previous methods are insufficient in their ability to phase variants at long distances, thereby preventing the characterization of the phenotypic impact of compound heterozygous genotypes. Additionally, structural variants of substantial interest for genomic diseases are difficult to accurately identify and characterize with previous techniques due to their large size in comparison to the reads and read inserts used to study them. Read-sets spanning tens of kilobases to megabases or longer can help alleviate this difficulty, thereby allowing for highly parallel and personalized analyses of structural variation.

Basic evolutionary and biomedical research can be driven by technological advances in high-throughput sequencing. It is now relatively inexpensive to generate massive quantities of DNA sequence data. However, it is difficult in theory and in practice to produce high-quality, highly contiguous genome sequences with previous technologies. Further, many organisms, including humans, are diploid, wherein each individual has two haploid copies of the genome. At sites of heterozygosity (e.g. where the allele given by the mother differs from the allele given by the father), it is difficult to know which sets of alleles came from which parent (known as haplotype phasing). This information can be critically important for performing a number of evolutionary and biomedical studies such as disease and trait association studies.

The present disclosure provides methods for genome assembly that combine technologies for DNA preparation with tagged sequence reads for high-throughput discovery of short, intermediate and long term connections corresponding to sequence reads from a single physical nucleic acid molecule bound to a complex such as a chromatin complex within a given genome. The disclosure further provides methods using these connections to assist in genome assembly, for haplotype phasing, and/or for metagenomic studies. While the methods presented herein can be used to determine the assembly of a subject's genome, it should also be understood that in certain cases the methods presented herein are used to determine the assembly of portions of the subject's genome such as chromosomes, or the assembly of the subject's chromatin of varying lengths. It should also be understood that, in certain cases, the methods presented herein are used to determine or direct the assembly of non-chromosomal nucleic acid molecules. Indeed, any nucleic acid the sequencing of which is complicated by the presence of repetitive regions separating non-repetitive contigs and/or scaffolds may be facilitated using the methods disclosed herein.

In some cases, the methods disclosed herein comprise the step of generating a plurality of contigs and/or scaffolds from sequencing fragments of target DNA obtained from a subject. In some cases, long stretches of target DNA are fragmented by cutting the DNA with one or more restriction enzymes, incompletely digesting the DNA with one or more nonspecific endonucleases, shearing the DNA, or a combination thereof. The resulting fragments are sequenced using high throughput sequencing methods to obtain a plurality of sequencing reads. Cases of high throughput sequencing methods which are described in U. S. Patent Application Number PCT/US2015/043327, which is hereby incorporated in its entirety, or any techniques known in the art.

Alternately or in combination with the above, in some cases, the methods disclosed herein are used with contig and/or scaffold information previously generated. Contig and/or scaffold information for a vast number of genomes, including the human genome, plant genome, bacteria genome, virus genome, and nematode genome. Rather than generating contig and/or scaffold information de novo, or in combination with de novo generated contig and/or scaffold data, the methods disclosed herein may be used to assist in the chromosomal assembly, ordering and orientation of these previously generated contigs and/or scaffolds.

In some cases, samples comprising target DNA used to generate contigs and/or scaffolds are obtained from a subject by any number of means, including by taking bodily fluids (e.g., blood, urine, serum, lymph, saliva, anal and vaginal secretions, perspiration and semen), taking tissue, biopsy, sewage, water, soil, air, or by collecting cells/organisms. The sample obtained may be comprised of a single type of cell/organism, or may be comprised multiple types of cells/organisms. In some cases, the DNA are extracted and prepared from the subject's sample. For example, the samples are treated to lyse a cell comprising the polynucleotide, using known lysis buffers, sonication techniques, electroporation, and the like. In further cases, the target DNA is further purified to remove contaminants, such as proteins, by using alcohol extractions, cesium gradients, and/or column chromatography.

In further cases, the methods disclosed herein allow for accurate and predictive results for genotype assembly, haplotype phasing, and metagenomics with small amounts of materials. In some cases, less than about 0.1 µg, about 0.2 µg, about 0.3 µg, about 0.4 µg, about 0.5 µg, about 0.6 µg, about 0.7 µg, about 0.8 µg, about 0.9 µg, about 1.0 µg, about 1.2 µg, about 1.4 µg, about 1.6 µg, about 1.8 µg, about 2.0 µg, about 2.5 µg, about 3.0 µg, about 3.5 µg, about 4.0 µg, about 4.5 µg, about 5.0 µg, about 6.0 µg, about 7.0 µg, about 8.0 µg, about 9.0 µg, about 10 µg, about 15 µg, about 20 µg, about 30 µg, about 40 µg, about 50 µg, about 60 µg, about 70 µg, about 80 µg, about 90 µg, about 100 µg, about 150 µg, about 200 µg, about 300 µg, about 400 µg, about 500 µg, about 600 µg, about 700 µg, about 800 µg, about 900 µg, or about 1000 µg of DNA is used with the methods disclosed herein. In some cases, the DNA used in the methods disclosed herein is extracted from less than about 1,000,000, about 500,000, about 200,000, about 100,000, about 50,000, about 20,000, about 10,000, about 5,000, about 2,000, about 1,000, about 500, about 200, about 100, about 50, about 20, or about 10 cells.

Methods to extract very high molecular weight DNA is described in U.S. Patent Application Number PCT/US2015/

043327, which is hereby incorporated in its entirety. In some cases, the read-sets provide sequence information over a span of greater than about 10 kb, about 50 kb, about 100 kb, about 200 kb, about 500 kb, about 1 Mb, about 2 Mb, about 5 Mb, about 10 Mb, or about 100 Mb. In some cases, the read-sets provide sequence information over a span of greater than about 500 kb.

In some cases, the methods disclosed herein are used with chromatin isolated from a cell/organism, or with reconstituted chromatin. Reconstituted chromatin is differentiated from chromatin formed within a cell/organism over various features. First, for many samples, the collection of naked DNA samples can be achieved by using a variety of noninvasive to invasive methods, such as by collecting bodily fluids, swabbing buccal or rectal areas, taking epithelial samples, etc. Second, reconstituting chromatin substantially prevents the formation of inter-chromosomal and other long-range interactions that generate artifacts for genome assembly and haplotype phasing. In some cases, a sample has less than about 20, 15, 12, 11, 10, 9, 8, 7, 6, 5, 4, 3, 2, 1, 0.5, 0.4, 0.3, 0.2, 0.1% or less inter-chromosomal or intermolecular crosslinking according to the methods and compositions of the disclosure. In some cases, the sample has less than about 5% inter-chromosomal or intermolecular crosslinking. In some cases, the sample has less than about 3% inter-chromosomal or intermolecular crosslinking. In further cases, the sample has less than about 1% inter-chromosomal or intermolecular crosslinking. Third, the frequency of sites that are capable of crosslinking and thus the frequency of intramolecular crosslinks within the polynucleotide can be adjusted. For example, the ratio of DNA to histones can be varied, such that the nucleosome density is adjusted to a desired value. In some cases, the nucleosome density is reduced below the physiological level. Accordingly, the distribution of crosslinks can be altered to favor longer-range interactions. In some embodiments, sub-samples with varying cross-linking density may be prepared to cover both short- and long-range associations. In some cases, the crosslinking conditions is adjusted such that at least about 1%, about 2%, about 3%, about 4%, about 5%, about 6%, about 7%, about 8%, about 9%, about 10%, about 11%, about 12%, about 13%, about 14%, about 15%, about 16%, about 17%, about 18%, about 19%, about 20%, about 25%, about 30%, about 40%, about 45%, about 50%, about 60%, about 70%, about 80%, about 90%, about 95%, or about 100% of the crosslinks occur between DNA segments that are at least about 50 kb, about 60 kb, about 70 kb, about 80 kb, about 90 kb, about 100 kb, about 110 kb, about 120 kb, about 130 kb, about 140 kb, about 150 kb, about 160 kb, about 180 kb, about 200 kb, about 250 kb, about 300 kb, about 350 kb, about 400 kb, about 450 kb, or about 500 kb apart on the sample DNA molecule.

The term "about" as used herein in the context of a number refers to a range including that number and all values+/−10% of that number.

The term "double-strand breaks (DSBs)" as used herein, refers to damage on DNA generated when the two complementary stands of the DNA double helix are broken simultaneously at sites that are sufficiently close to one another that base-pairing and chromatin structure are insufficient to keep the two DNA ends juxtaposed. The two DNA ends generated by a DSB are liable to become physically dissociated from one another. DSBs may cause loss of genetic linkage information and physical linkage information.

The term "genetic linkage" or "linkage information" as used herein, refers to the tendency of alleles that are located close together on a chromosome to be inherited together during the meiosis phase of sexual reproduction. In general, genes whose loci are nearer to each other are less likely to be separated onto different chromatids during chromosomal crossover, and are said to be genetically linked. Typically, the nearer two genes are on a chromosome, the lower is the chance of a swap occurring between them, and the more likely they are to be inherited together. Linkage information usually indicates the relative location of two or more alleles on a chromosome.

The term "physical linkage" as used herein, refers to a condition wherein two or more DNA segments are locally or distally positioned on the same DNA molecule, thereby sharing a common phosphodiester backbone.

The term "physical linkage information" as used herein refers to information related to the understanding that a first segment and a second segment are present on a common molecule in a sample. Physical linkage information is useful for a number of downstream analysis approaches. For example, physical linkage information is useful in assembling contigs into scaffolds, as it indicates that contigs, even contigs that are derived from nonadjacent fragments of a nucleic acid molecule, assemble to a common scaffold. Physical linkage information is useful for assigning phasing information to a set of contigs. Physical linkage information in some cases relates to nucleic acid fragment proximity and to long range structure information for longer nucleic acid molecules. Long range structure information includes, for example, information relevant to the structure or the relative position of fragments or features that are separated by, for example, at least 10 kb.

The term "phasing" or "phasing information" or "haplotype phasing" or "haplotype estimate" refers to the process of statistical estimation of haplotypes from genotype data. Typically, the most common situation arises when genotypes are collected at a set of polymorphic sites from a group of individuals. For example, in human genetics genome-wide association studies collect genotypes in thousands of individuals at between 200,000-5,000,000 single nucleotide polymorphisms (SNPs) using microarrays. Haplotype estimation methods are used in the analysis of these datasets and allow genotype imputation of alleles from reference databases known in the art. Haplotype estimation is sometimes referred to as phasing.

The term "crosslinking" refers to when adjacent molecules become covalently bound. Crosslinking is also used informally and occasionally herein to refer to molecules that become bound together as a result of their binding partners becoming covalently bound to one another, such that the molecules are unable to be separated from newly covalently bound binding partners.

The terms "crosslinking agents" refer to molecules that covalently connect components of reconstituted chromatin. Naturally occurring crosslinking agents include, but are not limited to psoralens, mitomycin C, and nitrous acids. Certain metabolites of alcohol, cigarette, and high fat diet, such as acetaldehyde and malondialdehyde, can also act as cross-linkers. A preferred crosslinker or crosslinking agent is formaldehyde.

The term "N50" as used herein refers to the size or other value used to measure the median member of a set of members, such as the median nucleic acid length in a nucleic acid sample, or the median contig length in a set of contigs assembled from a sequenced nucleic acid sample, or the median scaffold length in a set of scaffolds assembled from contigs from a sequenced nucleic acid sample.

As used herein "degradation" refers to nonspecific nucleic acid damage such as that which results from nonenzymatic nucleic acid decay or nucleic acid cleavage due to enzyme or organism contamination. Generally, 'degradation' excludes nucleic acid cleavage or other modification which is intentional, sequence specific or otherwise performed pursuant to nucleic acid manipulation or nucleic acid library formation. DNA degradation can occur by any one or more of hydrolysis, oxidation, damage from enzymes, fragmentation, degradation, decay, mechanical forces, ultraviolet light, and shearing. DNA damage can occur over time, for example during storage. Time can trigger DNA degradation to occur, for example 1, 2, 3, 4, 5, 6, 7, 8, 9, 10, 11, 12, or more than 12 months, or 2, 3, 4, 5, 6, or more than 6 years. Additionally or alternatively, DNA degradation can occur during DNA storage, regardless of storage temperature. Drying a sample, cooling a sample, or freezing a sample, alone or in combination, often delays or reduces the extent of degradation of a nucleic acid sample, but does not prevent it from occurring all together.

In some cases, a sample is "subject to degradation" when the sample is subjected to conditions that result, in the absence of protective approaches such as those disclosed herein, in a reduction in an N50 measurement of the sample being reduced to no more than 50% of its original value. In alternate cases, a sample is "subject to degradation" when the sample is subjected to conditions that result, in the absence of protective approaches such as those disclosed herein, in a reduction in an N50 measurement of the sample being reduced to no more than 90%, 75%, 50%, 25%, 10%, 5%, 1%, 0.1%, 0.01%, or less than 0.01% of its original value.

An N50 of a sample refers, depending upon context, to the median nucleic acid length in a nucleic acid sample, or the median contig length in a set of contigs assembled from a sequenced nucleic acid sample, or the median scaffold length in a set of scaffolds assembled from a set of contigs of a sequenced nucleic acid sample.

The disclosure herein is further delineated in reference to the numbered embodiments recited below. For each embodiment referring to a previous numbered embodiment, it is understood that the reference is to the numbered embodiment recited, and alternatively also to all previous numbered embodiments in the numbered list herein. 1. A method of preserving physical linkage information in an isolated nucleic acid sample subjected to degradation comprising the steps of contacting the nucleic acid sample to a population of nucleic acid binding moieties to form at least one nucleic acid complex; subjecting the sample to degradation; and analyzing the nucleic acid sample; wherein the sample is protected from degradation such that physical linkage information is preserved. 2. The method of embodiment 1, wherein the population of nucleic acid binding moieties comprises polypeptides. 3. The method of embodiment 1, wherein the population of nucleic acid binding moieties comprises nucleic acid binding proteins. 4. The method of embodiment 1, wherein the population of nucleic acid binding moieties comprises histones. 5. The method of embodiment 1, wherein the population of nucleic acid binding moieties comprises nanoparticles. 6. The method of embodiment 1, wherein contacting the nucleic acid sample to a population of nucleic acid binding moieties comprises reconstituting chromatin on the nucleic acid sample. 7. The method of embodiment 1, wherein the at least one nucleic acid complex comprises a single nucleic acid molecule prior to subjecting the sample to degradation. 8. The method of embodiment 1, wherein the nucleic acid sample is contacted to a crosslinking agent following contacting to the population of nucleic acid binding moieties. 9. The method of embodiment 8, wherein the crosslinking agent comprises formaldehyde. 10. The method of embodiment 1, wherein the degradation introduces at least one double-strand break into the sample. 11. The method of embodiment 1, wherein the degradation comprises nonenzymatic degradation. 12. The method of embodiment 1, wherein the degradation comprises sequence-independent nonenzymatic degradation. 13. The method of embodiment 1, wherein the degradation comprises oxidation. 14. The method of embodiment 1, wherein the degradation comprises hydrolysis. 15. The method of embodiment 1, wherein the degradation comprises UV radiation. 16. The method of embodiment 1, wherein the degradation comprises uncooled incubation. 17. The method of embodiment 1, wherein the degradation comprises incubation at room temperature. 18. The method of embodiment 1, wherein the degradation comprises enzymatic degradation. 19. The method of embodiment 1, wherein the degradation comprises sequence-independent enzymatic degradation. 20. The method of embodiment 1, wherein the analyzing comprises amplifying a fragment of the isolated nucleic acid sample. 21. The method of embodiment 1, wherein analyzing comprises probing using a first probe able to anneal to a first DNA segment and a second probe able to anneal to a second DNA segment. 22. The method of embodiment 1, wherein the analyzing comprises binding a fragment of the isolated nucleic acid sample to an array. 23. The method of embodiment 1, wherein the analyzing comprises cloning a fragment of the isolated nucleic acid sample into a host cell. 24. The method of embodiment 1, wherein the analyzing comprises sequencing at least a portion of the isolated nucleic acid sample. 25. The method of embodiment 24, wherein sequencing the sample comprises enzymatic cleavage to expose internal segment ends for labeling. 26. The method of embodiment 25, wherein the labeling comprises tagging internal segment ends. 27. The method of embodiment 26, wherein the tagging comprises attaching oligos such that exposed ends of a DNA complex are commonly tagged, and such that different complexes are differentially tagged relative to one another. 28. The method of embodiment 25, wherein the labeling comprises ligating a first exposed end of a nucleic acid in a complex to a second exposed end of the nucleic acid in the complex. 29. The method of embodiment 24, wherein sequencing the sample comprises labeling internal segment ends. 30. The method of embodiment 29, wherein the labeling comprises tagging internal segment ends. 31. The method of embodiment 30, wherein the tagging comprises attaching oligos such that exposed ends of a DNA complex are commonly tagged, and such that different complexes are differentially tagged relative to one another. 32. The method of embodiment 29, wherein the labeling comprises ligating a first exposed end of a nucleic acid in a complex to a second exposed end of the nucleic acid in the complex. 33. The method of embodiment 24, wherein sequencing the sample comprises contacting the population of nucleic acid binding moieties to a protease. 34. The method of embodiment 33, wherein the protease comprises proteinase K. 35. The method of embodiment 1, wherein the protection comprises an increase in nucleic acid fragment size N50 of at least 2× relative to an unprotected sample subjected to the degradation. 36. The method of embodiment 1, wherein the protection comprises an increase in nucleic acid fragment size N50 of at least 5× relative to an unprotected sample subjected to the degradation. 37. The method of embodiment 1, wherein the protection comprises an increase in nucleic acid fragment size N50 of at least 50× relative to an unprotected sample subjected to the degradation. 38. The method of embodiment 1, wherein the protection comprises an increase in assembled contig sequence N50 of at least 2× relative to an unprotected sample subjected to the degradation. 39. The method of embodiment 1, wherein the protection comprises an increase in assembled contig sequence of at least 5× relative to an unprotected sample subjected to the degradation. 40. The method of embodiment 1, wherein the protection comprises an increase in assembled contig sequence N50 of at least 50× relative to an unprotected sample subjected to the degradation. 41. The method of embodiment 1, wherein the protection comprises an increase in assembled scaffold sequence N50 of at least 2× relative to an unprotected sample subjected to the degradation. 42. The method of embodiment 1, wherein the protection comprises an increase in assembled scaffold sequence N50 of at least 5× relative to an unprotected sample subjected to the degradation. 43. The method of embodiment 1, wherein the protection comprises an increase in assembled scaffold sequence N50 of at least 50× relative to an unprotected sample subjected to the degradation. 44. The method of embodiment 1, wherein the complex is dried down during said subjecting. 45. The method of embodiment 1, wherein the complex is refrigerated during said subjecting. 46. The method of embodiment 1, wherein the complex is frozen during said subjecting. 47. A method for preserving physical linkage information of isolated DNA comprising the steps of a) contacting the isolated DNA to a DNA binding agent to form at least one DNA complex comprising a single DNA molecule and at least one DNA binding agent, b) contacting the DNA complex to a cross-linking agent, c) subjecting the DNA complex to degradation, d) cleaving the single DNA molecule into a first segment having a first exposed DNA end and a second segment having a second exposed DNA end, e) adding label information to the first exposed DNA end and the second exposed DNA end, such that the label information identifies the first segment and the second segment as arising from the single DNA molecule, and f) analyzing at least a portion of the labeled first segment and the labeled second segment, such that label information relevant to physical linkage information is obtained; wherein the DNA complex is subjected to DNA damage prior to said analyzing. 48. The method of embodiment 47, wherein analyzing is performed at least 6 months after contacting the DNA complex to the cross-linking agent. 49. The method of embodiment 47, wherein non-complexed DNA molecules are removed prior to analyzing. 50. The method of embodiment 47, wherein the DNA damage results from contact to an enzyme. 51. The method of embodiment 50, wherein the enzyme is a restriction endonuclease. 52. The method of embodiment 47, wherein the DNA damage results from contact to a nonenzymatic agent. 53. The method of embodiment 52, wherein the DNA damage results from a DNA damaging agent comprising hydrolysis, oxidation, damage from enzymes, fragmentation, degradation, decay, mechanical forces, ultraviolet light and/or shearing. 54. The method of embodiment 47, wherein the DNA damage results from degradation over time. 55. The method of embodiment 47, wherein the DNA damaging results from storage of the DNA complex. 56. The method of embodiment 55, wherein the storage comprises room-temperature storage. 57. The method of embodiment 55, wherein the storage comprises cold storage. 58. The method of embodiment 57, wherein the cold storage comprises freezing. 59. The method of embodiment 57, wherein the cold storage comprises cryopreservation. 60. The method of embodiment 47, wherein the DNA binding agent is a protein. 61. The method of embodiment 60, wherein the protein is a nuclear protein. 62. The method of embodiment 61, wherein the nuclear protein is a histone. 63. The method of embodiment 47, wherein the DNA binding agent is a nanoparticle. 64. The method of embodiment 47, comprising discarding DNA not bound to a DNA binding agent prior to adding tag information. 65. The method of embodiment 47, wherein analyzing comprises sequencing. 66. The method of embodiment 65, wherein sequencing comprises sequencing at least a portion of the tagged first segment and the tagged second segment, such that sequencing reads comprising the tagging information are obtained. 67. The method of embodiment 47, wherein analyzing comprises probing using a first probe able to anneal to a first DNA segment and a second probe able to anneal to a second DNA segment. 68. The method of embodiment 47, wherein analyzing comprises binding to an array. 69. The method of embodiment 47, wherein analyzing comprises amplification of a larger fragment. 70. The method of embodiment 47, wherein analyzing comprises cloning into a plasmid or library. 71. The method of embodiment 47, comprising sequencing a first junction formed by the first exposed DNA end and the label information and sequencing a second junction formed by the second exposed DNA end and the label information. 72. The method of embodiment 47, comprising sequencing a portion of a first labeled fragment and a portion of a second labeled fragment. 73. The method of embodiment 71, comprising discarding DNA not bound in a DNA complex prior to sequencing the first junction. 74. The method of embodiment 71, comprising assigning the first segment and the second segment to a common phase or common molecule. 75. The method of embodiment 47, wherein the label information comprises oligonucleotide sequence information that is common to the DNA complex. 76. The method of embodiment 47, wherein the label information added to the first exposed DNA end comprises sequence of the single DNA molecule that is distal to the first segment. 77. The method of embodiment 76, wherein the label information added to the second exposed DNA end comprises sequence of the single DNA molecule that is distal to the second segment. 78. The method of embodiment 47, wherein the analyzing is performed at least 12 months after contacting the DNA complex to the cross-linking agent. 79. The method of embodiment 47, wherein the analyzing is performed at least 24 months after contacting the DNA complex to the cross-linking agent. 80. A method of identifying a nucleic acid preservative comprising the steps of a) separating a nucleic acid sample into a first portion and a second portion; b) contacting the first portion and the second portion to a DNA binding agent having a first binding agent parameter set; c) contacting the first portion and the second portion to a crosslinking agent having a first crosslinking parameter set; d) contacting the first portion to a DNA degrading agent; e) contacting the first portion and the second portion to dsDNA cleaving agent to generate a first exposed end and a second exposed end in each portion; f) labeling exposed ends of the first portion and the second portion; g) sequencing tagged exposed ends of the first portion and the second portion to generate a first portion sequence and a second portion sequence; h) evaluating relative quality of the first portion sequence assembly and the second portion sequence assembly; i) changing at least one of the first binding agent parameter set and the first crosslinking parameter set; j) repeating steps a) through h), replacing at least one of the first binding agent parameter set and the first crosslinking parameter set with a second binding agent parameter set and a second crosslinking parameter set; and k) selecting the parameter set yielding a greater relative quality of a sequence assembly. 81. The method of embodiment 80, wherein the DNA binding agent is a protein. 82. The method of embodiment 81, wherein the protein is a nuclear protein. 83. The method of embodiment 82, wherein the nuclear protein is a histone. 84. The method of embodiment 80, wherein the DNA binding agent is a nanoparticle. 85. The method of embodiment 80, wherein the DNA degrading agent is an enzyme. 86. The method of embodiment 85, wherein the enzyme is a restriction endonuclease. 87. The method of embodiment 80, wherein the DNA degrading agent is a nonenzymatic agent. 88. The method of embodiment 80, wherein DNA degrading agent is a DNA damaging agent selected from the list consisting of hydrolysis, oxidation, damage from enzymes, fragmentation, degradation, decay, mechanical forces, ultraviolet light, and/or shearing. 89. The method of embodiment 80, wherein the DNA degrading agent comprises degradation over time. 90. The method of embodiment 80, comprising discarding DNA not bound to a DNA binding agent prior to adding tag information. 91. The method of embodiment 80, comprising sequencing a first junction formed by the first exposed DNA end and its label and sequencing a second junction formed by the second exposed DNA end and its label. 92. The method of embodiment 80, comprising sequencing a portion of a first segment and sequencing a portion of a second segment. 93. The method of embodiment 91, comprising discarding DNA not bound in a DNA complex prior to analyzing. 94. The method of embodiment 91, comprising assigning the first segment and the second segment to a common phase or common molecule. 95. The method of embodiment 80, wherein the label information comprises oligonucleotide sequence information that is common to the DNA complex. 96. The method of embodiment 80, wherein the label information added to the first exposed DNA end comprises sequence of the single DNA molecule that is distal to the first segment. 97. The method of embodiment 80, wherein the label information added to the second exposed DNA end comprises sequence of the single DNA molecule that is distal to the second segment. 98. The method of embodiment 80, wherein the label information is added at least 12 months after contacting the DNA complex to the cross-linking agent. 99. The method of embodiment 80, wherein the label information is added at least 24 months after contacting the DNA complex to the cross-linking agent. 100. A method of isolating a size-threshold selected fraction of a fragmented nucleic acid sample, comprising the steps of contacting the sample to a population of nucleic acid binding moieties to form at least one nucleic acid complex, wherein the nucleic acid binding moieties bind to nucleic acid fragments over a threshold size; removing unbound nucleic acid fragments; and analyzing a portion of said nucleic acid fragments over a size-threshold. 101. The method of embodiment 100, wherein analyzing comprises probing using a first probe able to anneal to a first DNA segment and a second probe able to anneal to a second DNA segment. 102. The method of embodiment 100, wherein analyzing comprises binding to an array. 103. The method of embodiment 100, wherein analyzing comprises amplification of a larger fragment. 104. The method of embodiment 100, wherein analyzing comprises cloning into a plasmid or library. 105. The method of embodiment 100, wherein analyzing a portion of said at least one nucleic acid complex comprises cleaving at least one size-selected fragment to form a first segment and a second segment, tagging an end of said first fragment and tagging an end of said second fragment such that said tagging conveys physical linkage information, sequencing across a first fragment tagged end and a second fragment tagged end, and assigning sequence reads having common tagging physical linkage information to a common phase of a sequence assembly. 106. The method of embodiment 100, wherein said threshold size is at least 140 bp. 107. The method of embodiment 100, wherein said threshold size is at least 200 bp. 108. The method of embodiment 100, wherein said threshold size is at least 500 bp. 109. The method of embodiment 100, wherein said threshold size is at least 1000 bp. 110. The method of embodiment 100, wherein said threshold size is a minimum size necessary for a nucleic acid to bind to a nucleosome. 111. The method of embodiment 100, wherein said fragmented nucleic acid sample is age-degraded. 112. The method of embodiment 106, wherein said age-degraded sample is stored for at least 1 year prior to said sequencing. 113. The method of embodiment 100, wherein said fragmented nucleic acid sample is temperature-degraded. 114. The method of embodiment 113, wherein said temperature-degraded sample is held at room-temperature for at least 3 days. 115. The method of embodiment 100, wherein said fragmented nucleic acid sample is chemically degraded. 116. The method of embodiment 115, wherein the fragmented nucleic acid sample is chemically degraded by a reagent having endonuclease activity. 117. The method of embodiment 115, wherein the fragmented nucleic acid sample is chemically degraded by a reagent that catalyzes phosphodiester backbone breakage. 118. The method of embodiment 100, wherein said fragmented nucleic acid sample is degraded by contact to UV radiation. 119. A method of preserving physical linkage information in a nucleic acid sample likely to undergo double-strand breakage comprising the steps of cleaving the nucleic acid sample so as to expose at least one internal double-strand end; labeling the at least one internal double-strand end so as to preserve physical linkage information; and subjecting the nucleic acid sample to conditions likely to comprise double-strand breakage. 120. The method of embodiment 119, wherein cleaving the nucleic acid so as to expose at least one internal double strand end comprises contacting the nucleic acid sample to a plurality of DNA binding moieties such that an individual nucleic acid of said sample comprising a first segment and a second segment is bound such that the first segment and the second segment are held together independent of their common phosphodiester backbone; and cleaving the individual nucleic acid between the first segment and the second segment. 121. The method of embodiment 119, wherein labeling the at least one internal double-strand end so as to preserve physical linkage information comprises ligating a first nonadjacent exposed end of the individual nucleic acid to the first segment, and ligating a second nonadjacent exposed end of the individual nucleic acid end to the second segment. 122. The method of embodiment 119, wherein labeling the at least one internal double-strand end so as to preserve physical linkage information comprises attaching oligonucleotides having a common sequence to the first segment and the second segment. 123. The method of embodiment 119, wherein the likely double-strand breakage comprises age-degradation. 124. The method of embodiment 123, wherein the likely double-strand breakage comprises age-degradation for at least 1 year prior to said sequencing. 125. The method of embodiment 119, wherein the likely double-strand breakage comprises temperature-degradation. 126. The method of embodiment 125, wherein the likely double-strand breakage comprises temperature-degradation at room-temperature for at least 3 days. 127. The method of embodiment 119, wherein the likely double-strand breakage comprises chemical degradation. 128. The method of embodiment 127, wherein the likely double-strand breakage comprises chemical degradation by a reagent having endonuclease activity. 129. The method of embodiment 127, wherein the likely double-strand breakage comprises chemical degradation by a reagent that catalyzes phosphodiester backbone breakage. 130. The method of embodiment 119, wherein the likely double-strand breakage comprises degradation by contact to UV radiation. 131. A method of preserving physical linkage information in a nucleic acid sample likely to undergo double-strand breakage comprising the steps of contacting the nucleic acid sample to a plurality of DNA binding moieties such that an individual nucleic acid of said sample comprising a first segment and a second segment is bound such that the first segment and the second segment are held together independent of their common phosphodiester backbone; and subjecting the nucleic acid sample to conditions likely to comprise double-strand breakage. 132. The method of embodiment 131, comprising analyzing the nucleic acid sample. 133. The method of embodiment 131, wherein the analyzing comprises amplifying a fragment of the isolated nucleic acid sample. 134. The method of embodiment 131, wherein the analyzing comprises binding a fragment of the isolated nucleic acid sample to an array. 135. The method of embodiment 131, wherein the analyzing comprises cloning a fragment of the isolated nucleic acid sample into a host cell. 136. The method of embodiment 131, wherein the analyzing comprises sequencing at least a portion of the isolated nucleic acid sample. 137. The method of embodiment 132, wherein the analyzing comprises sequencing the nucleic acid sample. 138. The method of embodiment 137, wherein sequencing the nucleic acid sample comprises cleaving the individual nucleic acid between the first segment and the second segment to expose at least one internal double-strand end, and labeling the at least one internal double-strand end so as to preserve physical linkage information. 139. The method of embodiment 138, wherein labeling the at least one internal double-strand end so as to preserve physical linkage information comprises ligating a first nonadjacent exposed end of the individual nucleic acid to the first segment, and ligating a second nonadjacent exposed end of the individual nucleic acid end to the second segment. 140. The method of embodiment 138, wherein labeling the at least one internal double-strand end so as to preserve physical linkage information comprises attaching oligonucleotides having a common sequence to the first segment and the second segment. 141. The method of embodiment 131, wherein the likely double-strand breakage comprises age-degradation. 142. The method of embodiment 141, wherein the likely double-strand breakage comprises age-degradation for at least 1 year prior to said sequencing. 143. The method of embodiment 131, wherein the likely double-strand breakage comprises temperature-degradation. 144. The method of embodiment 143, wherein the likely double-strand breakage comprises temperature-degradation at room-temperature for at least 3 days. 145. The method of embodiment 131, wherein the likely double-strand breakage comprises chemical degradation. 146. The method of embodiment 145, wherein the likely double-strand breakage comprises chemical degradation by a reagent having endonuclease activity. 147. The method of embodiment 145, wherein the likely double-strand breakage comprises chemical degradation by a reagent that catalyzes phosphodiester backbone breakage. 148. The method of embodiment 131, wherein the likely double-strand breakage comprises degradation by contact to UV radiation. 149. A kit for preserving physical linkage information of isolated DNA comprising reagents for DNA extraction, at least one DNA binding agent, and at least one DNA cross-linker, wherein the kit reagents do not require refirgeration. 150. The kit of embodiment 149, wherein the DNA extraction reagents are for high molecular weight DNA extraction. 151. The kit of embodiment 149, wherein the DNA binding agent is a protein. 152. The kit of embodiment 151, wherein the protein is a nuclear protein. 153. The kit of embodiment 152, wherein the nuclear protein is a histone. 154. The kit of embodiment 149, wherein the DNA binding agent is a nanoparticle. 155. The kit of embodiment 149, wherein the DNA cross-linker is formaldehyde. 156. The kit of embodiment 149, wherein the reagents are stable at room temperature for a least 1 month. 157. The kit of embodiment 156, wherein the reagents are stable at room temperature for at least 6 months. 158. The kit of embodiment 157, wherein the reagents are stable at room temperature for at least 12 months. 159. A method of identifying a nucleic acid preservative comprising the steps of a) contacting a nucleic acid sample to a DNA binding agent having a first binding agent parameter set; b) contacting the nucleic acid sample to a crosslinking agent having a first crosslinking parameter set; c) contacting the nucleic acid sample to a DNA degrading agent; d) contacting the nucleic acid sample to dsDNA cleaving agent to generate a first exposed end and a second exposed end; e) labeling exposed ends of the nucleic acid sample; f) sequencing labeled exposed ends of the nucleic acid sample to generate a the nucleic acid sample sequence assembly; g) evaluating relative quality of the nucleic acid sample sequence assembly; h) changing at least one of the first binding agent parameter set and the first crosslinking parameter set; i) repeating steps a) through h), replacing at least one of the first binding agent parameter set and the first crosslinking parameter set with a second binding agent parameter set and a second crosslinking parameter set; and j) selecting the parameter set yielding a greater relative quality of a sequence assembly. 160. The method of embodiment 159, wherein the DNA binding agent is a protein. 161. The method of embodiment 160, wherein the protein is a nuclear protein. 162. The method of embodiment 161, wherein the nuclear protein is a histone. 163. The method of embodiment 159, wherein the DNA binding agent is a nanoparticle. 164. The method of embodiment 159, wherein the DNA degrading agent is an enzyme. 165. The method of embodiment 164, wherein the enzyme is a restriction endonuclease. 166. The method of embodiment 159, wherein the DNA degrading agent is a nonenzymatic agent. 167. The method of embodiment 159, wherein DNA degrading agent is a DNA damaging agent comprising: hydrolysis, oxidation, damage from enzymes, fragmentation, degradation, decay, mechanical forces, ultraviolet light, and/or shearing. 168. The method of embodiment 159, wherein the DNA degrading agent comprises degradation over time. 169. The method of embodiment 159, comprising discarding DNA not bound to a DNA binding agent prior to adding tag information. 170. The method of embodiment 159, comprising sequencing a first junction formed by the first exposed DNA end and the label information and sequencing a second junction formed by the second exposed DNA end and the label information. 171. The method of embodiment 170, comprising discarding DNA not bound in a DNA complex prior to sequencing the first junction. 172. The method of embodiment 170, comprising assigning the first segment and the second segment to a common phase or common molecule. 173. The method of embodiment 159, wherein the label information comprises oligonucleotide sequence information that is common to the DNA complex. 174. The method of embodiment 159, wherein the label information added to the first exposed DNA end comprises sequence of the single DNA molecule that is distal to the first segment. 175. The method of embodiment 159, wherein the label information added to the second exposed DNA end comprises sequence of the single DNA molecule that is distal to the second segment. 176. The method of embodiment 159, wherein the label information is added at least 12 months after contacting the DNA complex to the cross-linking agent. 177. The method of embodiment 159, wherein the label information is added at least 24 months after contacting the DNA complex to the cross-linking agent.

The following examples are intended to illustrate but not limit the disclosure. While they are typical of those that might be used, other procedures known to those skilled in the art may alternatively be used.

EXAMPLES

Example 1. Identification of Collection Methods

Multiple prospective collection methods suitable for both clinical and research sample collection were identified. The two best were commercially available saliva collection kits (Oragene DNA Genotek Inc.) and a Blood and Cell Culture DNA midi BMW DNA extraction kit (Qiagen). The former is non-invasive while the latter can be used on almost any tissue sample, including blood.

HMW DNA was easily collected for CSDS storage, chromatin was reconstituted with such DNA, and long-range information was retrieved directly from the storage substrate. This demonstrated long-range information storage and retrieval.

Example 2. Reconstituted Chromatin Protects DNA from Fragmentation and Damage This experiment is directed at determining whether and to what extent both fixed and unfixed chromatin prevent the occurrence of DNA fragmentation under conditions such as those experienced during long-term storage and shipment. Reconstituted chromatin in both forms (fixed and unfixed) protects DNA from various sources of damage via sequestration. While the primary benefit of this preservation method is the retention of long-range information in spite of fragmentation, the prevention of fragmentation to begin with is a secondary and complementary goal.

The following experiments are performed to demonstrate that chromatin protects DNA from damage and determine whether crosslinked chromatin enhances the protection. Human NA12878 DNA with a mean fragment size of 150 kb is prepared in one of the following three ways: 1) untreated (naked DNA), 2) reconstituted into chromatin with an in vitro assembly kit (Active Motif), and 3) reconstituted into chromatin and then fixed with formaldehyde. Each of the three treatments is subjected to four experiments: 1) exposure to 37° C. for 2 weeks, 2) vortexing vigorously on a standard benchtop vortexer for 1 minute to simulate shear stresses 3) treatment with radiant flux of 15 Gy/min of ionizing radiation for 40 seconds, and 4) incubation with limiting amounts of DNase for 10 minutes. For chromatin treatments, protein is removed with protease treatment and DNA gently purified prior to measurement.

DNA fragment size distributions for each of the 3 treatments are compared for each experimental condition. These size distributions are determined using pulse-field gel electrophoresis of the DNA to look for signs of low molecular weight DNA. DNA fragment distributions is compared within experiments and examined for shifts between treatments. Treatments that are protective against fragmentation have greater proportions of their fragment mass at higher molecular weights.

Experiments utilizing radiation are prohibitive due to the difficulty and associated safety risks. In this case, alternative chemical sources of free-radical damage to induce fragmentation, for example hydrogen peroxide, are used. Additionally, some experimental conditions as specified do not adequately damage even naked DNA, in which case the experimental parameters are tuned until the control (naked DNA) treatment realizes damage. At 25° C. and moderate pH, naked DNA is estimated to experience 1-4 breaks per megabase per year. Our simulated damage experiments achieve a similar breakage rate.

Unprotected (naked) DNA demonstrates the most fragmentation in all experiments while DNA assembled into chromatin and fixed demonstrates the least, with unfixed chromatin being intermediate between the two. The resulting data are used to make quantitative measurement of the rates of fragmentation under the specified conditions.

Example 3. Preservation of Long-Range Genomic Information with CMDS Despite Fragmentation This example is meant to demonstrate the retention of long-range contiguity information in DNA under adverse conditions, testing how our chromatin assembly and cross-linking method protects DNA from stresses in the long term. This enables developing methods for the collection and storage of crosslinked chromatin for later analysis (e.g. Chicago library analysis).

Aging of DNA is simulated by exposure to sustained raised temperatures which accelerates the chemical processes that occur slowly under normal conditions over time. The same three treatments and four experimental conditions as in Example 2 are replicated here. The parameters of the experiments are tuned to ensure fragmentation/degradation of all treatments in light of Example 2. Retention of long-range information is measured with the generation and sequencing of Chicago libraries and presence of fragmentation is measured by gel electrophoresis comparisons against intact, control input DNA.

Figure 2:
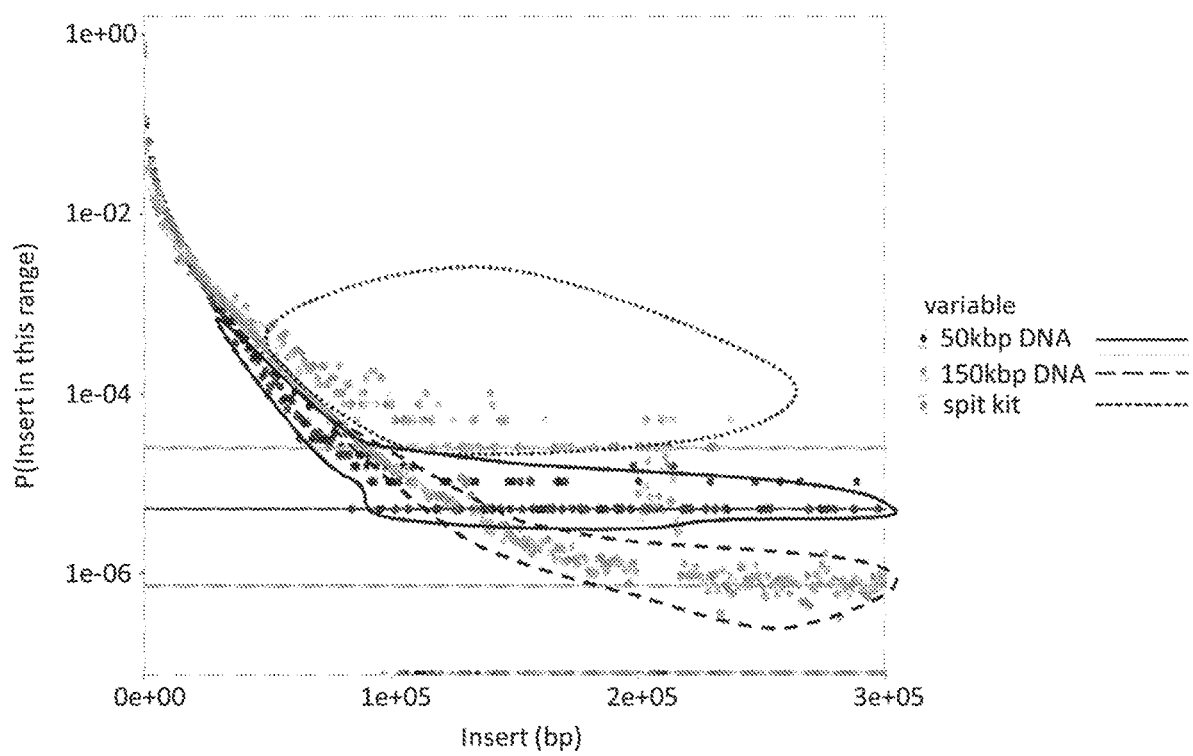
FIG. 2 illustrates insert distribution ranges for several libraries. Colored horizontal lines indicate noise level for color-matched library. Points enclosed by solid line are 50 kb DNA input (that is, having a mean 50 kb fragment size). Points enclosed by dashed line are 150 kb DNA input (that is, having a 150 kb fragment size). Points enclosed by dotted line are DNA from Oragene spit kit and extends to ~100 kb.

Retention of long-range information is quantified by examination of the insert distributions of the Chicago library sequence data. These libraries' insert distributions have been demonstrated to reflect the input DNA fragment size distribution (see FIG. 2), with the largest pairs spanning up to the maximum input fragments size. In practice this has produced read pairs spanning up to 200 kb from a DNA extraction kit advertising a mean fragment size of 150 kb, well within the range needed for this analysis. Insert distributions for each treatment are compared in size bins of 10 kb, with treatments embodying better long-range information retention having more mass in the larger insert-size bins than poorly retaining treatments.

Some treatments are fragmented that very few large fragments remain, making control comparisons difficult. In this case additional Chicago libraries are generated for the problematic treatments under more lenient conditions until a partial fragmentation treatment can be identified as compared with a whole, untreated control.

DNA that has been reconstituted into chromatin and fixed demonstrates the greatest retention of long-range information. DNA reconstituted into chromatin but not fixed has slightly better protection against damage than naked DNA, and does not display any better retention of long-range information. This is due to the necessity of redundant crosslinking to retain contiguity in the presence of fragmentation. Consequently, the reconstituted but unfixed chromatin retains no more long-range information than the naked DNA treatment. More than 25% of well-mapping read pairs span distances greater than 5 kb in the fixed chromatin treatment while read pairs from the other two treatments do not.

Example 4. High Quality of Sequence Information from Degraded, Fixed Chromatin Through De Novo Assembly of a Human Genome This example demonstrates that DNA preserved with the described method is completely sufficient for the generation of a high quality genome reconstruction, demonstrating the importance of long-range information for genomic studies and the sufficiency of the disclosed methods for producing it. Short insert read pair data is also required for the initial assembly generation, and therefore must be produced from the same preserved sample as the long-range information to demonstrate the all-in-one nature of this preservation method.

A single fixed chromatin treatment from Examples 2 and 3 are chosen as the input for this experiment. That treatment demonstrates 1) the presence of fragmentation and 2) the retention of long-range information in spite of fragmentation. A portion of the fragmented but preserved DNA is converted into a Chicago library. The other portion has protein removed, DNA purified, and a conventional shotgun library is generated. Both of these libraries are paired-end sequenced to sufficient depth on an Illumina HiSeq 2500.

The short-insert data is used to generate an initial assembly using Meraculous (Chapman et al. 2011 PMID: 21876754). This assembly is scaffolded using an internal scaffolding pipeline ("HiRise") and the Chicago sequence data. Contiguity and accuracy of the generated assembly is ascertained by comparison to the human reference and previous assemblies of the same individual that have not undergone degradation treatment. Various error modes (e.g., methylC→T transitions, apurinic bases) are quantified relative to reference.

When the input DNA is too fragmented to retain contiguity information sufficient for de novo assembly, more lenient, i.e. less fragmented, input treatment is chosen and additional libraries generated. The approach delimits conditions under which CMDS material preserves accurate sequence information.

The short-insert data produced is comparable to non-degraded preparations due to the nature of that library preparation, which shears the DNA as a first step, (median assembled fragment size around 100 kb). Chicago data is capable of increasing assembly contiguity 100×, and this degraded sample is capable of the same despite the presence of fragmentation. Consequently, this assembly is produced with a scaffold N50 greater than 10 Mb.

Example 5. Loss of Physical Linkage Information in Stored DNA Sample

A tissue sample is collected from a human subject. DNA in the tissue sample is extracted with phenol-chloroform. The isolated DNA is stored at room temperature. During storage double strand breaks occur over time. As a result, physical linkage information is lost. The stored DNA is subsequently shipped to a remote DNA analytical center, where the isolated DNA is converted into a sequencing library and sequenced.

A technician observes a collection of sequenced short reads. Although all nucleotides are sequenced, the technician is unable to assign physical linkage information of the DNA fragments and fails to assemble the DNA short reads into associated contigs and/or scaffolds to assemble a genome.

This example demonstrates that DNA physical linkage information is lost due to double strand breaks over the course of storage.

Example 6. Preservation of Physical Linkage Information in Stored DNA Sample

The tissue sample in Example 5 is treated to extract DNA as in Example 5. Protein histones are added to the isolated DNA to create formation of DNA complexes. The DNA complexes are fixed with formaldehyde before storing at room temperature. During storage, double strand breaks occur over time. The stored DNA complexes are then shipped to a remote DNA analytical center, where the DNA complexes are converted into a sequencing library and sequenced. Prior to sequencing, the DNA complexes are cleaved to form a plurality of short fragments. The ends of each fragment of a DNA complex are tagged such that each complex has a unique tag. The tagged fragments are allowed to ligate randomly.

A technician reports all nucleotides are sequenced. Although some double strand breaks occur during storage, the technician is able to obtain read pair junctions and to assign sequences on either side of junctions to a common phase. The technician successfully assigns physical linkage information of the DNA short reads, and is able to assemble the DNA short reads into associated contigs and/or scaffolds to assemble a genome. This experiment indicates that adding histone creates formation of DNA complexes and adding formaldehyde creates DNA crosslinking preserve long-range information and physical linkage information of DNA molecules. Additionally, tagging and ligating the DNA ends bring DNA fragments of a DNA molecule that have been cleaved and separated into proximity such that adjacent fragments that share the same phase are assigned to the same contig.

This example demonstrates that DNA physical linkage information is preserved by treating the DNA sample with a DNA binding agent and crosslinking to prevent DNA degradation over the course of storage.

Example 7. Preservation of Physical Linkage Information in Damaged DNA Sample

The tissue sample in Example 5 is treated to extract DNA as described in Example 5. The isolated DNA is treated the same as described in Example 6. Prior to storage, the DNA complexes are subjected to four treatments: (1) ultraviolet light, (2) hydrolysis, (3) oxidation, and (4) shaking and shearing. Each treatment is split into two portions such that one portion is crosslinked by treating with formaldehyde, and one portion is not crosslinked. In each case, the treatment causes double strand breaks. The stored DNA complexes are subsequently shipped to a remote DNA analytical center, where the DNA complexes are converted into a sequencing library and sequenced. Prior to sequencing, the DNA complexes are treated the same as described in Example 6.

A technician reports all nucleotides are sequenced. In samples that are crosslinked, the technician is able to obtain read pair junctions to assign the sequence of junctions to a common phase. The technician also successfully assigns physical linkage information of the DNA short reads, and is able to assemble the DNA short reads into associated contigs and/or scaffolds to assemble a genome. In samples that are not crosslinked, the technician is unable to obtain physical linkage information and fails to assemble the contigs and/or scaffolds. This experiment indicates that adding histone creates formation of DNA complexes and adding formaldehyde creates DNA crosslinking prevent DNA degradation in the presence of DNA damaging agents. As a result, the physical linkage information and long-range information of stored DNA are preserved and allow the technician to assign physical linkage information to DNA fragments, and to assign adjacent fragments of a DNA molecule to the same contig, subsequently to assemble a genome.

This example demonstrates that DNA physical linkage information is preserved by treating the DNA sample with a DNA binding agent and crosslinking to prevent DNA degradation in the presence of a DNA damaging agent during long term storage.

Example 8. Preservation of Physical Linkage Information from Stored DNA Sample for De Novo Assembly of a Genome A sample is collected from an unknown plant in a forest. DNA is extracted from the sample using simple techniques. Briefly, the sample is diced into fine pieces, followed by adding a pinch of salt and a household detergent, e.g. shampoo, to the bits of plant sample. DNA is isolated using phenol-chloroform. Protein histones are added to the isolated DNA to form DNA complexes and formaldehyde is added to create crosslinking. The DNA complexes are stored at room temperature. Six months later, the stored DNA complexes are shipped to a remote analytical center, where the DNA complexes are converted into a sequencing library and treated the same as described in Example 6 prior to sequencing.

A technician reports all nucleotides are sequenced. Although some double strand breaks occur during storage, the technician obtains read pair junction and assigns sequences on either side of the junction to a common phase. The technician successfully assigns physical linkage information to the short reads, and is able to assemble the DNA short reads into associated contigs and/or scaffolds to assemble a genome.

Example 9. High Quality of Sequence Information from DNA Sample for De Novo Assembly of a Genome to Identify a Human Subject A blood sample is collected from a crime scene. DNA is isolated from the sample, and histones are added to the isolated DNA to form DNA complexes. The resulted DNA complexes are treated with formaldehyde prior to storage at room temperature. Two years later, the stored DNA complexes are retrieved and sent for analysis. At the analytical center, a technician treated the DNA complexes as described in Example 6. Briefly, the DNA complexes are cleaved into a plurality of short fragments by treating the DNA complexes with an enzyme. The fragment ends are then tagged and randomly ligated as described in Example 6. The DNA complexes are subsequently sequenced.

A technician used the sequenced data to generate and assemble a genome. The technician assigns phase of the short fragments and assembles the reads to associated contigs and/or scaffolds. The assembled genome is ascertained by comparison to existing references and previous assemblies of human genomes. The sequence data of the blood sample is used to compare with sequence data collected from a suspect, and to sequence data collected from the victim of the crime.

Example 10. High Quality of Sequence Information from DNA Sample for De Novo Assembly of a Genome to Identify an Infectious Organism A biological sample from a patient is collected from an area experiencing a flu epidemic. DNA is isolated from the biological sample and is reconstituted with a DNA binding agent, e.g. histone, to create DNA complexes. The resulted DNA complexes are treated with formaldehyde prior to storage and transportation at room temperature. The stored DNA complexes are retrieved at an analytical center and are treated prior to sequencing as described in Example 6. The DNA complexes are pared-end sequenced to sufficient depth on an Illumina HiSeq 2500.

A technician used the sequenced data to generate and assemble a genome. The generated genome is ascertained by comparison to existing references and previous assemblies of viral genomes. The technician assigns phase of the short fragments and assembles the reads to associated contigs and/or scaffolds. The assembly is used to blast against a database of existing viral genomes to identify the infectious virus.

Example 11. High Quality of Sequence Information from DNA Sample for Genome Sequencing to Identify Disease Infected Tissues A biopsy is obtained from a tumor of a patient during a doctor's visit. A specimen from a non-tumor area of the same patient is also collected. DNA is isolated from each of the specimens, and protein histones are added to each of the isolated DNA to create DNA complexes. The resulted DNA complexes are treated with formaldehyde prior to storage at room temperature and transportation to an analytical center. The stored DNA complexes are retrieved at an analytical center and treated, subsequently converted into a sequencing library and sequenced as described in Example 6.

A technician used the sequenced data to generate and assemble a genome. The technician assigns phase of the short fragments and assembles the reads to associated contigs and/or scaffolds. The generated genome is ascertained by comparison to existing references human genomes. Additionally, the technician is able to obtain haplotype phase, and to determine whether two mutations occur on the same chromosome.

Example 12. Mutation-Baring Nucleic Acid with Indistinguishable Phase

A diploid organism, such as humans, contains two copies of each chromosome of genetic material. A human patient in a remote location has contracted malaria. A treatment exists to kill the malaria-causing parasite *Plasmodium falciparum*, though in order for the treatment to not be toxic to the patient, the patient must have at least one wild-type copy of a gene involved in red blood cell differentiation. DNA is extracted from the patient and shipped to a sequencing facility in a different country. The DNA sample is not able to be refrigerated during transit, and therefore DNA damage ensues over the weeks it takes for the sample to reach the sequencing facility. This DNA damage leads to many double strand breaks, which causes DNA fragmentation and loss of phasing and/or physical linkage information. Sequencing results in low quality short reads that indicate the patient has two point mutations at the gene locus, though because physical linkage information was lost during transit, it cannot be determined if the patient has one wild type allele and one allele harboring the two mutations versus the patient having a point mutation in both alleles. As a result, the patient is not able to receive the anti-malarial treatment.

Example 13. Determining Physical Linkage Information after DNA Damage

DNA is extracted from the patient of Example 12. DNA is assembled in vitro with DNA-binding proteins to generate reconstituted chromatin and then cross-linked. The DNA sample is then shipped to a sequencing center in another country. As DNA damage breaks the phosphodiester bond of a DNA molecule, the DNA molecule is still linked within the cross-linked chromatin complex. Therefore, physical linkage information is maintained despite DNA damage. Upon reaching the sequencing center, the reconstituted chromatin is digested with a restriction endonuclease. Exposed ends are ligated to tagged oligonucleotides which identify the tagged exposed ends as originating from the same DNA molecule. The DNA sample is sequenced and physical linkage information is determined. Because the phasing information was maintained and able to be determined, it is determined that the patient has one wild type allele and one mutant allele harboring two point mutations in the red blood cell differentiation gene. Since the patient has at least one wild type allele, she is able to receive the life-saving anti-malarial treatment.

Example 14. Linkage-Determining Tagging Information: Punctuated Long Read

DNA is extracted from the patient of Example 12. DNA is assembled in vitro with DNA-binding proteins to generate reconstituted chromatin. The reconstituted chromatin is cleaved to produce sticky ends, which are partially filled in to prevent religation. Punctuation oligonucleotides with ends compatible with the partially filled-in sticky ends are added to the chromatin sample along with a DNA ligase. In some instances, the punctuation oligonucleotides are dephosphorylated in order to avoid contatemerization of the oligonucleotides. The DNA segments of the religated chromatin sample are rearranged compared to the starting DNA sample, though physical linkage information is maintained since the molecule is bound to chromatin proteins through the punctuation process. When the rearranged DNA sample is released from the chromatin proteins and sequenced, physical linkage information is determined.

Example 15. Linkage-Determining Tagging Information: Transposon Punctuated Long Read The DNA sample of Example 12 is extracted and reassembled with DNA-binding proteins in vitro to generate reconstituted chromatin. Transposase bound to two unlinked punctuation oligonucleotides is added to the DNA sample. The transposase cleaves exposed DNA segments and inserts the two punctuation oligonucleotides into the DNA. Because the punctuation oligonucleotides in a given transposase are unlinked, the insertion results in two free DNA ends, each terminated by one of the two punctuation oligonucleotides and each tethered to the reconstituted chromatin to preserve physical linkage information. DNA ligase is added to the sample to ligate blunt DNA ends together, resulting in a rearrangement of DNA segments, though physical linkage information is maintained since the DNA molecule is bound to the chromatin proteins throughout this process. The rearranged DNA sample is released from the chromatin proteins and sequenced to determine physical linkage information.

Example 16. Linkage-Determining Tagging Information—Short Read Paired Ends

DNA is extracted from the patient of Example 12. DNA is assembled in vitro with DNA-binding proteins to generate reconstituted chromatin. The reconstituted chromatin is biotinylated, fixed with formaldehyde, and immobilized onto streptavidin beads. The sample is split and each portion of the DNA fragments is digested with a different restriction enzyme and incubated overnight. The resulting sticky ends are filled-in with an alpha-thio-dGTP and a biotinylated dCTP to generate blunt ends. The blunt ends are ligated with T4 ligase to generate paired-ends. The reconstituted chromatin is digested with a proteinase to recover the ligated paired-ends, which are then extracted from the beads and subject to an exonuclease digestion to remove biotin from unligated ends. The recovered paired-ends are sheared and the ends are filled-in with dNTPs. The biotinylated paired-ends are purified by a pull-down with streptavidin beads. In some cases, adaptors are ligated and the fragments are amplified for high-throughput sequencing. In this case, after being read on a short-read sequencer, phasing information is determined.

Example 17. Linkage-Determining Tagging Information—Short Read Tagged Ends

DNA is extracted from the organism of Example 12. DNA is assembled in vitro with DNA-binding proteins and then cleaved with a restriction endonuclease to generate exposed sticky ends. Barcoded and biotinylated oligonucleotides having ends compatible with the exposed sticky ends of the cleaved chromatin complex are added along with DNA ligase. Prior to sequencing, the tagged exposed ends are separated from the chromatin complex by shearing and purified with streptavidin beads. Sequencing reads having the same barcode are determined to be in phase.

Example 18. Determining Physical Linkage Information after DNA Damage Pre-Tagging DNA is extracted from the patient of Example 12. DNA is assembled in vitro with DNA-binding proteins to generate reconstituted chromatin and then cross-linked. The DNA sample is then shipped to a sequencing center in another country. As DNA damage breaks the phosphodiester bond of a DNA molecule, the DNA molecule is still linked within the cross-linked chromatin complex. Therefore, physical linkage information is maintained despite DNA damage. Upon reaching the sequencing center, the reconstituted chromatin is processed and sequenced as described in any of Examples 14-17 and physical linkage information is determined. In some cases, the processing includes removing non-complexed DNA prior to adding tagging information.

Example 19. Determining Physical Linkage Information after DNA Damage Post-Tagging DNA is extracted from the organism of Example 12. DNA is assembled in vitro with DNA-binding proteins to generate reconstituted chromatin and then cross-linked. The chromatin is then cleaved and tagged as described in any of Examples 14-17 in order to add tagging information. The sample is then shipped to a sequencing center in another country. As DNA damage breaks the phosphodiester bond of a DNA molecule, the DNA molecule is still linked within the cross-linked chromatin complex. As further DNA damage causes fragments of the DNA molecule to dissociate from the reconstituted chromatin complex, the tagging information of the DNA molecule is maintained. Therefore, physical linkage information is preserved despite DNA damage. Upon reaching the sequencing center, the sample is sequenced and physical linkage information is determined.

Example 20. Isolation of Phase-Informative or Physical Linkage-Informative Nucleic Acid Molecules DNA is isolated from the organism of Example 12. Following DNA damage, the DNA sample consists of DNA molecules of varying lengths. Long DNA molecules are needed to determine physical linkage information. The DNA sample is assembled in vitro into reconstituted chromatin. Only the DNA molecules long enough to wrap about the DNA binding proteins will be incorporated into the chromatin complex. The sample is washed to remove non-complexed DNA molecules, leaving only the reconstituted chromatin complexes. The complexed DNA molecules which contain important phasing information, are processed as described in any of Examples 13-16 in order to add tagging information and subsequently sequenced, resulting in determination of physical linkage information.

Example 21. Isolation of Phase-Informative or Physical Linkage-Informative Nucleic Acid Molecules Following DNA Damage New evidence is uncovered for an unsolved case, prompting detectives to request sequencing of DNA samples previously obtained from the crime scene. Two of the lead suspects are identical twin brothers with nearly identical DNA sequences, though it is know from previous testing that DNA from the twin can be distinguished from each other at a specific locus. Twin #1 has a wild type locus and a mutant locus harboring two mutations specifically T48A and G5079A, while Twin #2 has two mutant alleles, one having the T48A mutation and the second having the G5079A mutation. To determine which twin committed the crime, the stored DNA sample from the crime scene must be sequenced such that physical linkage information is generated which can distinguish between the two twins. Unfortunately, the DNA sample has been stored at room temperature for multiple years and is highly degraded and fragmented. Only the long DNA fragments will contain the needed physical linkage information. Due to sequencing costs, the forensic lab does not have the budget to sequence the entire sample, nor do they want to PCR-amplify the sample due to the likely incorporation of errors that would convolute the data. In order to isolate only the phase-informative or physical linkage-informative nucleic acid molecules, the highly damaged DNA sample is assembled in vitro with DNA-binding proteins in order to generate reconstituted chromatin. Only DNA fragments long enough to wrap around the DNA-binding proteins will be incorporated into the chromatin, which is ideal since these long fragments will contain the needed physical linkage information. Following chromatin reconstitution, the sample is washed to remove all of the non-bound DNA molecules. This process enriches the phase containing DNA molecules while not losing yield. The enriched DNA sample is then sequenced and physical linkage information is generated such that Twin #2 is identified as the criminal and subsequently arrested.

Example 22. Identifying a Nucleic Acid Preservative

Isolated DNA is separated into two portions. Each portion is assembled in vitro into reconstituted chromatin and cross-linked. The first portion is then treated with a DNA oxidizing agent. Both portions are then process to add tagging information as described in any of Examples 14-17. After sequencing, the relative quality of the sample from the first and second portion is evaluated to determine how much damage was caused by the DNA oxidizing agent. The experiment is repeated, though this time the concentration of the cross-linking agent is increased. Following sequencing, it is determined that the sample with increased cross-linking is of a higher quality than that with less cross-linking and it is determined that increasing DNA cross-linking is an effective DNA preservative.

Example 23. Methods to Generate Chromatin In Vitro

Two approaches to reconstitute chromatin, narrowly defined, are of particular attention: one approach is to use ATP-independent random deposition of histones onto DNA, while the other approach uses ATP-dependent assembly of periodic nucleosomes. The disclosure allows the use of either approach with one or more methods disclosed herein. Examples of both approaches to generate chromatin can be found in Lusser et al. ("Strategies for the reconstitution of chromatin," Nature Methods (2004), 1(1):19-26), which is incorporated herein by reference in its entirety, including the references cited therein. Additional methods are available for the assembly of reconstituted more broadly defined, such as reconstituted chromatin comprising nanoparticles.

What is claimed is:

1. A method of analyzing a nucleic acid sample comprising:
    obtaining a nucleic acid sample comprising DNA molecules;
    forming at least one DNA complex by contacting the sample to a population of DNA binding moieties;
    reacting the at least one DNA complex to a cross-linking agent such that a physical linkage information of the DNA molecules from the sample is preserved and a cross-linked DNA complex is formed;
    obtaining the physical linkage information of the DNA molecules from the sample by sequencing the DNA molecules of the cross-linked DNA complex; and
    assigning the physical linkage information to an assembled contig sequence, wherein the assembled contig sequence has an N50 at least two times greater than the N50 of an assembled contig sequence of a control DNA molecule subjected to a DNA damage prior to the sequencing step, wherein the control DNA molecule does not contact with the population of DNA binding moieties, wherein the sequencing step is performed at least 6 months after said reacting the at least one DNA complex to a cross-linking agent, and wherein the cross-linked DNA complex is subjected to the DNA damage prior to the sequencing step.

2. The method of claim 1, wherein the DNA damage comprises non-enzymatic degradation of the DNA molecules of the cross-linked DNA complex and the control DNA molecule.

3. The method of claim 1, wherein the DNA damage comprises oxidation of the DNA molecules of the cross-linked DNA complex and the control DNA molecule.

4. The method of claim 1, wherein the DNA damage comprises hydrolysis of the DNA molecules of the cross-linked DNA complex and the control DNA molecule.

5. The method of claim 1, wherein the DNA damage comprises fragmentation of the DNA molecules of the cross-linked DNA complex and the control DNA molecule.

6. The method of claim 1, wherein the DNA damage comprises mechanical degradation of the DNA molecules of the cross-linked DNA complex and the control DNA molecule.

7. The method of claim 1, further comprising, prior to the sequencing step, ligating exposed ends of the DNA molecules in the cross-linked DNA complex to one another.

8. The method of claim 7, wherein the at least 6 months are at least 12 months and the exposed ends of the DNA molecules are ligated at least 12 months after the at least one DNA complex is formed.

9. The method of claim 1, wherein said sequencing the DNA molecules of the cross-linked DNA complex generates read pair data that spans a distance of at least 100 kilobases (kb).

10. The method of claim 1, further comprising, prior to the sequencing step, contacting a protease to the DNA binding moieties of the cross-linked DNA complex wherein the DNA binding moieties comprise nucleic acid binding proteins.

11. The method of claim 10, wherein the protease is proteinase K.

12. The method of claim 1, wherein the DNA molecules in the sample are bound with a reconstituted chromatin.

13. The method of claim 1, wherein the cross-linking agent is formaldehyde.

14. The method of claim 1, wherein the sample is a tissue sample.

15. The method of claim 14, wherein the tissue sample is a cancer tissue sample.

16. The method of claim 1, further comprising obtaining contig information of the DNA molecules, and assembling the contig information into one or more scaffolds using the physical linkage information.

17. The method of claim 1, wherein the physical linkage information comprises a long-range structure information relevant to the structure or relative position of DNA fragments that are separated by at least 10 kilobases (kb).

18. The method of claim 1, wherein the physical linkage information comprises phasing information.

* * * * *